(12) United States Patent
Yu et al.

(10) Patent No.: US 6,852,528 B2
(45) Date of Patent: *Feb. 8, 2005

(54) HUMAN AND MOUSE UROPLAKIN II GENE TRANSCRIPTIONAL REGULATORY ELEMENTS

(75) Inventors: De-Chao Yu, Foster City, CA (US); Hong Zhang, Cupertino, CA (US); Daniel R. Henderson, Palo Alto, CA (US)

(73) Assignee: Cell Genesys, Inc., San Francisco, CA (US)

(*) Notice: Subject to any disclaimer, the term of this patent is extended or adjusted under 35 U.S.C. 154(b) by 115 days.

This patent is subject to a terminal disclaimer.

(21) Appl. No.: 09/814,292

(22) Filed: Mar. 21, 2001

(65) Prior Publication Data

US 2002/0120117 A1 Aug. 29, 2002

Related U.S. Application Data

(60) Provisional application No. 60/191,861, filed on Mar. 24, 2000.

(51) Int. Cl.$^7$ .................. C12N 15/861; C12N 15/00; C12N 7/00; A61K 35/76; C07H 21/04
(52) U.S. Cl. .................. 435/320.1; 435/235.1; 435/6; 435/69.1; 435/69.7; 435/455; 514/44; 536/23.1; 536/23.4; 536/24.1
(58) Field of Search .................. 435/235.1, 320.1, 435/6, 69.1–69.7, 455; 514/44; 536/23.1, 23.4, 24.1

(56) References Cited

U.S. PATENT DOCUMENTS

| | | | |
|---|---|---|---|
| 5,670,367 A | 9/1997 | Dorner et al. | |
| 5,698,443 A | 12/1997 | Henderson et al. | |
| 5,824,543 A | 10/1998 | Sun | |
| 5,994,128 A | 11/1999 | Fallaux et al. | |
| 5,998,205 A | 12/1999 | Hallenbeck et al. | |
| 6,001,646 A | 12/1999 | Sun | |
| 6,692,736 B2 * | 2/2004 | Yu et al. | 424/93.2 |

FOREIGN PATENT DOCUMENTS

| | | |
|---|---|---|
| WO | WO 95/19434 | 7/1995 |
| WO | WO 96/39494 | 12/1996 |
| WO | WO 97/01358 | 1/1997 |
| WO | WO 98/39465 | 9/1998 |
| WO | WO 98/39466 | 9/1998 |
| WO | WO 98/39467 | 9/1998 |
| WO | WO 99/06576 | 2/1999 |
| WO | WO 99/25810 | 5/1999 |
| WO | WO 99/25860 | 5/1999 |

OTHER PUBLICATIONS

Lin, Jun–Hsiang et al., "A tissue–specific promoter that can drive a foreign gene to express in the suprabasal urothelial cells of transgenic mice," *Proc. Natnl. Acad. Sci. USA*, vol. 92, pp. 679–683, Jan. 1995.

* cited by examiner

*Primary Examiner*—Gerry Leffers
(74) *Attorney, Agent, or Firm*—Linda R. Judge; Pamela J. Sherwood; Bozicevic, Field & Francis LLP

(57) ABSTRACT

The invention provides new urothelial cell specific transcriptional regulatory sequences derived from human uroplakin II (hUPII), as well as polynucleotide constructs such as adenoviral vectors and methods of using hUPII-derived TREs. Additionally, the invention provides adenoviral vectors comprising a gene, preferably an adenovirus gene, under transcriptional control of a urothelial cell-specific transcriptional regulatory element (TRE). These vectors display urothelial cell-specific cytotoxicity, which is especially useful in the context of bladder cancer, in which destruction of these cells is desirable. The invention further provides compositions and host cells comprising the vectors, as well as method of using the adenoviral vectors.

27 Claims, 27 Drawing Sheets

FIG. 1A

```
TCGATAGGTA  CCCACTATAG  GGCACGCGTG  GTCGACGGCC  CGGGCTGGTC
1                                                        50

TGGCAACTTC  AAGTGTGGGC  CTTTCAGACC  GGCATCATCA  GTGTTACGGG
51                                                      100

GAAGTCACTA  GGAATGCAGA  ATTGATTGAG  CACGGTGGCT  CACACCTGTA
101                                                     150

ATCCCAACAC  TCTGGGAGGC  CAAGGCAGGT  GGATCACTTG  TGGTCAGGAG
151                                                     200

TTTGAGACCA  GCCTGGCCAA  CATGGTGAAA  CCTCATCTCT  ACTAAAAATA
201                                                     250

CAAAAATTAG  CTGGGAATGG  TGGCACATGC  CTATAATCCC  AGTTACTCAG
251                                                     300

GAGGCTGAGG  CAGGAGAATC  ATTTGAACCT  GGGAGGCAGA  GGTTGCAGTG
301                                                     350

AGCCGAGATC  ACGCCACTGC  ACTCCAGCCT  GGGTGACACA  GCGAGACTCT
351                                                     400

GTCTCAAAAA  AAAAAAAATG  CAGAATTTCA  GGCTTCACCC  CAGACCCACT
401                                                     450

GCATGACTGC  ATGAGAAGCT  GCATCTTAAC  AAGATCCCTG  GTAATTCATA
451                                                     500

CGCATATTAA  ATTTGGAGAT  GCACTGGCGT  AAGACCCTCC  TACTCTCTGC
501                                                     550

TTAGGCCCAT  GAGTTCTTCC  TTTACTGTCA  TTCTCCACTC  ACCCCAAACT
551                                                     600

TTGAGCCTAC  CCTTCCCACC  TTGGCGGTAA  GGACACAACC  TCCCTCACAT
601                                                     650

TCCTACCAGG  ACCCTAAGCT  TCCCTGGGAC  TGAGGAAGAT  AGAATAGTTC
651                                                     700

GTGGAGCAAA  CAGATATACA  GCAACAGTCT  CTGTACAGCT  CTCAGGCTTC
701                                                     750
```

FIG. 1B

```
     TGGAAGTTCT  ACAGCCTCTC  CCGACAAAGT  ATTCCACTTT  CCACAAGTAA
751                                                           800

CTCTATGTGT  CTGAGTCTCA  GTTTCCACTT  TTCTCTCTCT  CTCTCTCTCT
801                                                           850

CAACTTTCTG  AGACAGAGTT  TCACTTAGTC  GCCCAGGCTG  GAGTGCAGGG
851                                                           900

GCACAATCTC  GGCTCACTGC  AACCTCCACC  TCCTGGGTTC  AAGTGTTTCT
901                                                           950

CCTGTCTCAG  CCTCCCGAGT  AGCTGGGATT  ACAGGCACAC  ACCACCGCGT
951                                                          1000

TAGTTTTTGT  ATTTTTGGTA  GAGATGGTGT  TTCGCCATAT  TGGCCAGGCT
1001                                                         1050

GATCTCGAAC  TCCTGACCTC  AGGTGATCCG  CCCACCTCGG  CCTCCCAAAG
1051                                                         1100

TGCTGGGATT  ACAGGCATGA  GCCACCACGC  CCGGCTGATC  TCTTTTCTAT
1101                                                         1150

TTTAATAGAG  ATCAAACTCT  CTGTGTTGCC  TAGGCTGGTC  TTGAACTCCT
1151                                                         1200

GGCCTCGAGT  GATCCTCCCA  CCTTGGCCTC  CCAAAGTGTT  GAGATTACAG
1201                                                         1250

GCATGAGCCA  CTGTGCCTGG  CCTCAGTTCT  ACTACAAAAG  GAAGCCAGTA
1251                                                         1300

CCAGCTACCA  CCCAGGGTGG  CTGTAGGGCT  ACAATGGAGC  ACACAGAACC
1301                                                         1350

CCTACCCAGG  GCCCGGAAGA  AGCCCCGACT  CCTCTCCCCT  CCCTCTGCCC
1351                                                         1400

AGAACTCCTC  CGCTTCTTTC  TGATGTAGCC  CAGGGCCGGA  GGAGGCAGTC
1401                                                         1450

AGGGAAGTTC  TGTCTCTTTT  TCATGTTATC  TTACGAGGTC  TCTTTTCTCC
1451                                                         1500
```

FIG. 1C

```
ATTCTCAGTC  CAACAAATGG  TTGCTGCCCA  AGGCTGACTG  TGCCCACCCC
1501                                                      1550

CAACCCCTGC  TGGCCAGGGT  CAATGTCTGT  CTCTCTGGTC  TCTCCAGAAG
1551                                                      1600

TCTTCCATGG  CCACCTTCGT  CCCCACCCTC  CAGAGGAATC  TGAAACCGCA
1601                                                      1650

TGTGCTCCCT  GGCCCCACA   GCCCCTGCCT  CTCCCAGAGC  AGCAGTACCT
1651                                                      1700

AAGCCTCAGT  GCACTCCAAG  AATTGAAACC  CTCAGTCTGC  TGCCCCTCCC
1701                                                      1750

CACCAGAATG  TTTCTCTCCC  ATTCTTACCC  ACTCAAGGCC  CTTTCAGTAG
1751                                                      1800

CCCCTTGGAG  TATTCTCTTC  CTACATATCA  GGGCAACTTC  CAAACTCATC
1801                                                      1850

ACCCTTCTGA  GGGGTGGGGG  AAAGACCCCC  ACCACATCGG  GGGAGCAGTC
1851                                                      1900

CTCCAAGGAC  TGGCCAGTCT  CCAGATGCCC  GTGCACACAG  GAACACTGCC
1901                                                      1950

TTATGCACGG  GAGTCCAGA   AGAAGGGGTG  ATTTCTTTCC  CCACCTTAGT
1951                                                      2000

TACACCATCA  AGACCCAGCC  AGGGCATCCC  CCCTCCTGGC  CTGAGGGCCA
2001                                                      2050

GCTCCCCATC  CTGAAAAACC  TGTCTGCTCT  CCCCACCCCT  TTGAGGCTAT
2051                                                      2100

AGGGCCCAAG  GGGCAGGTTG  GACTGGATTC  CCCTCCAGCC  CCTCCCGCCC
2101                                                      2150

CCAGGACAAA  ATCAGCCACC  CCAGGGGCAG  GGCCTCACTT  GCCTCAGGAA
2151                                                      2200

CCCCAGCCTG  CCAGCACCTA  TTCCACCTCC  CAGCCCAGCA
2201                                            2239
```

FIG. 2A

```
    CTCGAGGATCTCGGCCCTCTTTCTGCATCCTTGTCCTAAATCATTTTCAT
1                                                  50

ATCTTGCTAGACCTCAGTTTGAGAGAAACGAACCTTCTCATTTTCAAGTT
51                                                100

GAAAAAAAAAAGAGGTTCAAAGTGGCTCACTCAAAGTTACAAGCCAACAC
101                                               150

TCACCACTACGAGTACAATGGCCACCATTAGTGCTGGCATGCCCCAGGAG
151                                               200

ACAGGCATGCATATTATTCTAGATGACTGGGAGGCAGAGGGTGGCCTAG
201                                               250

TGAGGTCAGACTGTGGACAGATCAGGCAGATGTGGGTTCTGATCCCAATT
251                                               300

CCTCAGGCCGCAGAACTACTGTGGTTCAAGAAGGGGACAAAAGGACTGCA
301                                               350

GTCCGGAACAGGAGGTCCATTTGAGAGCTGACTGAGCAGAAGAGGAAAGT
351                                               400

GAAGAACTTCTGGGGCAAGAGCTTACCCTACTTTACAGCTTTGTTGTCTT
401                                               450

CTTTACTCCAGGGGCGTCCCTGGTACTCAGTAAATGTCTGTTGGCTTGAG
451                                               500

GAACATATGTGTAAGGAGGAAGGAGAGGGAACTTGAGGGAGTTAAGACTC
501                                               550

AAGAATCAATCAAGGAGAGGACAGCAGAGAAGACAGGGTTTGGGAGAGAG
551                                               600

ACTCCAGACATTGGCCCTGGTTCCCTTCTTGGCCACTGTGAAACCCTCCA
601                                               650

GAGGAACTGAGTGCTGTGGCTTTAAATGATCTCAGCACTGTCAGTGAAGC
651                                               700

GCTCTGCTCAAAGAGTTATCCTCTTGCTCCTGTGCCGGGGCCTCCCCCTC
701                                               750

CTCTCAGCTCCCAAACCCTTCTCAGCCACTGTGATGGCATAATTAGATGC
751                                               800

GAGAGCTCAGACCGTCAGGTCTGCTCCAGGAACCACCCATTTTCCCCAAC
801                                               850
```

FIG. 2B

```
     CCCAGAGAAAGGTCCTAGTGGAAAAGTGGGGGCCACTGAAGGGCTGATGG
851                                                900

GGTTCTGTCCTTTCCCCCATGCTGGGTGGACTTAAAGTCTGCGATGTGTG
900                                                950

TAGGGGGTAGAAGACAACAGAACCTGGGGGCTCCGGCTGGGAGCAGGAGG
951                                               1000

AACTCTCACCAGACGATCTCCAAATTTACTGTGCAATGGACGATCAGGAA
1001                                              1050

ACTGGTTCAGATGTAGCTTCTGATACAGTGGGTCTGAGGTAAAACCCGAA
1051                                              1100

ACTTAATTTCTTTCAAAAATTTAAAGTTGCATTTATTATTTTATATGTGT
1101                                              1150

GCCCATATGTGTGCCACAGTGTCTATGTGGAGGTCAGAGGGCAAGTTGTG
1151                                              1200

GGCATTGGCTCTCTCCTTTCATAATGTGGCTTCTGGGGACCAAAATGTCA
1201                                              1250

GGCATGGTGGCAAGAGCTTTTACCTGTTGAGCCATCTCATGGTTTCGTAA
1251                                              1300

AACTTCCTATGACGCTTACAGGTAACGCAGAGACACAGACTCACATTTGG
1301                                              1350

AGTTAGCAGATGCTGTATTGGTGTAAACACTCATACACAGACACACACAC
1351                                              1400

ATACTCATACACACACACACACTTATCACATGCACACACATACTCGTA
1401                                              1450

TACACACAGACACACACACATGCACTCTCACATTCACATATTCATACACA
1451                                              1500

TCCACACACACACTCATCCACACACACAGACACACATACTCATCCACACA
1501                                              1550

CACACACACACATACTCATACACACACACAGACACACATACTCATACACA
1551                                              1600

CACACAGACACACACATATAATCATACATACACAGACACACTCATACATG
1601                                              1650

TGCACACACACACTCATCCACACACACACACTCATACACACACACACTCA
1651                                              1700
```

FIG. 2C

```
TACACACACACACTCATACACACACACACGAGGTTTTTCTCAGGCTGCCT
1701                                              1750

TTGGGTGGAGACTGGAACTGATTTCTGTTTTTCAGCTCCTTGGCTTTTTG
1751                                              1800

TCCCTTTAGATGAGATCTCCTCCTCACTTTACACACAGAAAGATCACACA
1801                                              1850

CGAGGGAGAACTGGCGGTGCGGAAGAGGGCTACACGGTAGGGTGTCAGGG
1851                                              1900

TCAGGAGATCTTCCTGGCAAGTCTCAAACCTCCACATAGCACAGTGTTTA
1901                                              1950

CGTGAGGATTTAGGAGGAATCAGGAAGAGGATTGGTTTACTGCAGAGCAG
1951                                              2000

ACCATATAGGTCCACTCCTAAGCCCCATTTGAAATTAGAAGTGAGACAGT
2001                                              2050

GTGGGATAAAAAGAGCAGATCTCTGGTCACATTTTTAAAGGGATATGAGG
2051                                              3000

GTCCTGTGCCTTTAAGCCTTCCCATCTCCCTCCAATCCCCCCTCACCTTC
2101                                              2150

CCCACCCTAACCCTCCCCAGGTTTCTGGAGGAGCAGAGTTGCGTCTTCTC
2151                                              2200

CCTGCCCTGCCGAGCTGCTCACTGGCTGCTCTAGAGGCTGTGCTTTGCGG
2201                                              2250

TCTCCATGGAAACCATTAGTTGCTAAGCAACTGGAGCATCATCTGTGCTG
2251                                              2300

AGCTCAGGTCCTATCGAGTTCACCTAGCTGAGACACCCACGCCCCTGCAG
2301                                              2350

CCACTTTGCAGTGACAAGCCTGAGTCTCAGGTTCTGCATCTATAAAAACG
2351                                              2400

AGTAGCCTTTCAGGAGGGCATGCAGAGCCCCTGGCCAGCGTCTAGAGGA
2401                                              2450

GAGGTGACTGAGTGGGGCCATGTCACTCGTCCATGGCTGGAGAACCTCCA
2451                                              2500

TCAGTCTCCCAGTTAGCCTGGGGCAGGAGAGAACCAGAGGAGCTGTGGCT
2501                                              2550
```

FIG. 2D

```
GCTGATTGGATGATTTACGTACCCAATCTGTTGTCCCAGGCATCGAACCC
2551                                              2600

CAGAGCGACCTGCACACATGCCACCGCTGCCCCGCCCTCCACCTCCTCTG
2601                                              2650

CTCCTGGTTACAGGATTGTTTGTCTTGAAGGGTTTTGTTGTTGCTACTT
2651                                              2700

TTTGCTTTGTTTTTTCTTTTTTAACATAAGGTTTCTCTGTGTAGCCCTAG
2701                                              2750

CTGTCCTGGAACTCACTCTGTAGACCAGGCTGGCCTCAAACTCAGAAATC
2751                                              2800

CACCTTCCTCCCAAGTGCTGGGATTAAAGGCATTCGCACCATCGCCCAGC
2801                                              2850

CCCCGGTCTTGTTTCCTAAGGTTTTCCTGCTTTACTCGCTACCCGTTGCA
2851                                              2900

CAACCGCTTGCTGTCCAAGTCTGTTTGTATCTACTCCACCGCCCACTAGC
2901                                              2950

CTTGCTGGACTGGACCTACGTTTACCTGGAAGCCTTCACTAACTTCCCTT
2951                                              3000

GTCTCCACCTTCTGGAGAAATCTGAAGGCTCACACTGATACCCTCCGCTT
3001                                              3050

CTCCCAGAGTCGCAGTTTCTTAGGCCTCAGTTAAATACCAGAATTGGATC
3051                                              3100

TCAGGCTCTGCTATCCCCACCCTACCTAACCAACCCCCTCCTCTCCCATC
3101                                              3150

CTTACTAGCCAAAGCCCTTTCAACCCTTGGGGCTTTTCCTACACCTACAC
3151                                              3200

ACCAGGGCAATTTTAGAACTCATGGCTCTCCTAGAAAACGCCTACCTCCT
3201                                              3250

TGGAGACTGACCCTCTACAGTCCAGGAGGCAGACACTCAGACAGAGGAAC
3251                                              3300

TCTGTCCTTCAGTCGCGGGAGTTCCAGAAAGAGCCATACTCCCCTGCAGA
3301                                              3350

GCTAACTAAGCTGCCAGGACCCAGCCAGAGCATCCCCCTTTAGCCGAGGG
3351                                              3400
```

FIG. 2E

```
CCAGCTCCCCAGAATGAAAAACCTGTCTGGGGCCCCTCCCTGAGGCTACA
3401                                             3450

GTCGCCAAGGGGCAAGTTGGACTGGATTCCCAGCAGCCCCTCCCACTCCG
3451                                             3500

AGACAAAATCAGCTACCCTGGGGCAGGCCTCATTGGCCCCAGGAAACCCC
3501                                             3550

AGCCTGTCAGCACCTGTTCCAGGATCCAGTCCCAGCGCAGTA
3551                                   3592
```

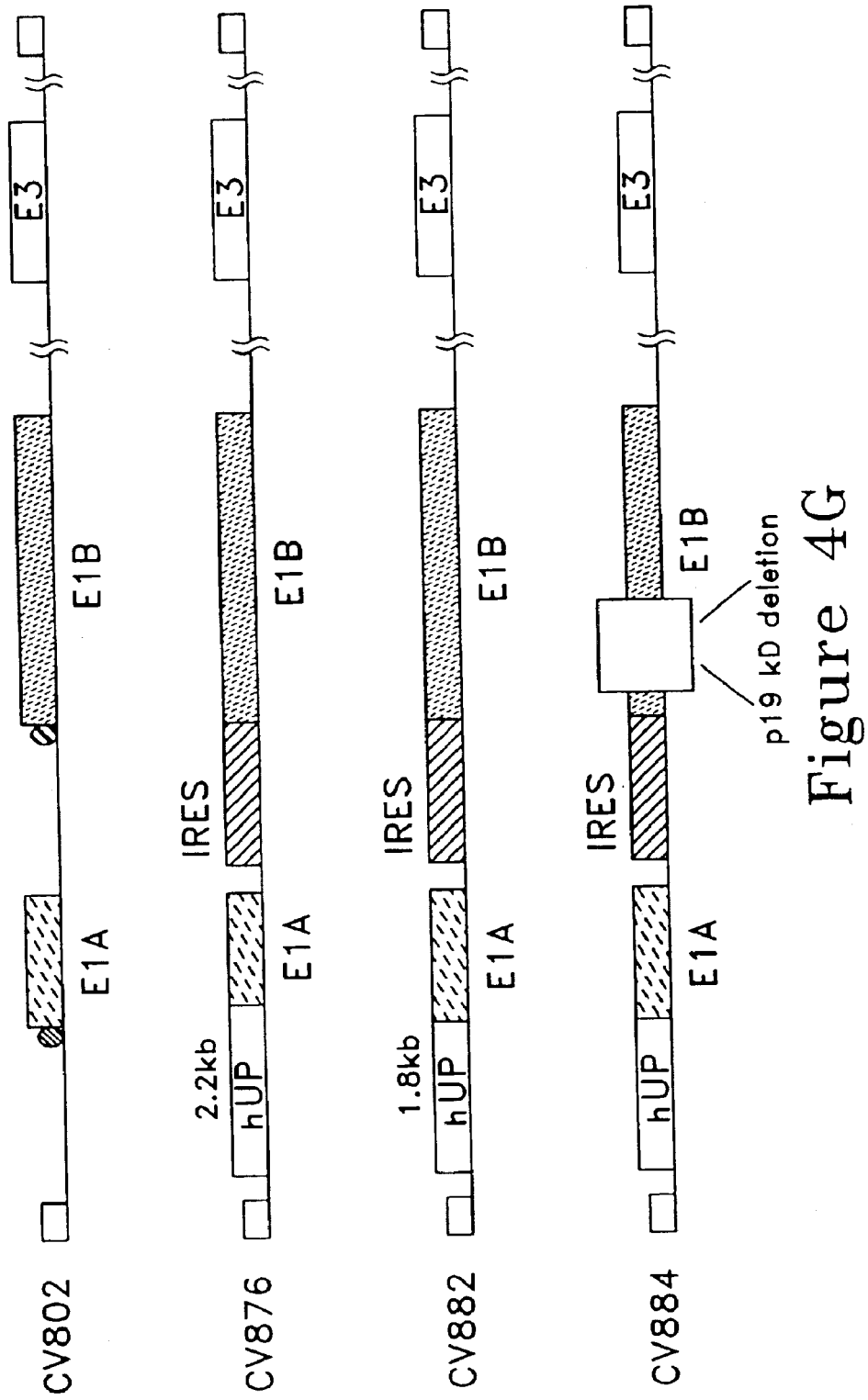

FIG. 12

```
G ATG ACC GGC TCA ACC ATC GCG CCC ACA ACG GAC TAT CGC AAC ACC
46
  Met Thr Gly Ser Thr Ile Ala Pro Thr Thr Asp Tyr Arg Asn Thr
   1           5              10                    15

ACT GCT ACC GGA CTA ACA TCT GCC CTA AAT TTA CCC CAA GTT CAT GCC
94
Thr Ala Thr Gly Leu Thr Ser Ala Leu Asn Leu Pro Gln Val His Ala
              20               25                    30

TTT GTC AAT GAC TGG GCG AGC TTG GAC ATG TGG TGG TTT TCC ATA GCG
142
Phe Val Asn Asp Trp Ala Ser Leu Asp Met Trp Trp Phe Ser Ile Ala
             35              40                 45

CTT ATG TTT GTT TGC CTT ATT ATT ATG TGG CTT ATT TGT TGC CTA AAG
190
Leu Met Phe Val Cys Leu Ile Ile Met Trp Leu Ile Cys Cys Leu Lys
         50              55              60

CGC AGA CGC GCC AGA CCC CCC ATC TAT AGG CCT ATC ATT GTG CTC AAC
238
Arg Arg Arg Ala Arg Pro Pro Ile Tyr Arg Pro Ile Ile Val Leu Asn
         65              70              75

CCA CAC AAT GAA AAA ATT CAT AGA TTG GAC GGT CTG AAA CCA TGT TCT
286
Pro His Asn Glu Lys Ile His Arg Leu Asp Gly Leu Lys Pro Cys Ser
 80              85              90                      95

CTT CTT TTA CAG TAT GAT TAA
307
Leu Leu Leu Gln Tyr Asp
            100
```

HUMAN AND MOUSE UROPLAKIN II GENE TRANSCRIPTIONAL REGULATORY ELEMENTS

The above-identified application claims priority to U.S. Provisional application 60/191,861 filed Mar. 24, 2000, which provisional application is hereby incorporated herein in its entirety.

TECHNICAL FIELD

The invention provides new human DNA sequences which confer urothelial-cell specific expression on heterologous genes. Additionally, the invention relates to cell transduction using adenoviral vectors, and more particularly to adenoviral vectors which replicate preferentially in urothelial cells.

BACKGROUND

Approximately 51,200 new cases of bladder cancer are diagnosed each year in the United States. Of these, approximately 38,000 cases are in men and 13,200 in women. Of the 51,200 new cases, approximately 80 percent will be classified at diagnosis as superficial, i.e., the cell have not invaded the muscularis propria. Of these, approximately 10 to 15 percent will eventually progress to invasive disease. The estimated number of deaths from bladder cancer in the United States in 1994 was 7,000 in men and 3,600 in women.

In the United States, transitional cell carcinoma (TCC) accounts for 90 to 95 percent of all tumors of the bladder. Squamous cell carcinoma (SCC) represents 5 to 10 percent, and adenocarcinoma approximately 1 to 2 percent. Squamous cell and adenomatous elements are often found in association with transitional cell tumors, especially with high grade tumors.

Bladder cancer is generally divided into superficial and invasive disease. A critical factor is the distinction between those tumors that are confined to the mucosa and those that have penetrated the basement membrane and extended into the lamina propria. The term "superficial bladder tumor" is generally used to represent a tumor that has not invaded the muscularis. Invasive tumors are described as those that have invaded the muscularis propria, the perivesical fibroadipose tissue, or adjacent structures. Carcinoma in situ (CIS) is a high grade and aggressive manifestation of TCC of the bladder that has a highly variable course.

Management of bladder cancer depends on whether the cancer is superficial or invasive. Most patients with superficial bladder cancer can be adequately treated with transurethral resection or fulguration of the tumor. However, with superficial bladder cancer, recurrence is the rule, and about 71 percent of patients develop tumor recurrences after endoscopic resection, and of these, about half experience recurrence within one year after the original resection. Agents used to treat CIS include bacille Calmette-Guérin (BCG) and chemotherapeutic agents, including doxorubicin. Response rates of up to 70 percent have been reported with BCG. However, treatment is not successful in all CIS patients, and some have progression to invasive or metastatic disease. Treatment of muscle-invasive bladder cancer includes radical cystectomy. Combination chemotherapy is generally used to treat metastatic bladder cancer, but success rates are dismal. Approximately 50 percent of patients with high-grade bladder cancer and deep muscle invasion die of disseminated disease within two years of presentation.

A number of urothelial cell-specific proteins have been described, among which are the uroplakins. Uroplakins (UP), including UPIa and UPIb (27 and 28 kDa, respectively), UPII (15 kDa), and UPIII (47 kDa), are members of a group of integral membrane proteins that are major proteins of urothelial plaques. These plaques cover a large portion of the apical surface of mammalian urothelium and may play a role as a permeability barrier and/or as a physical stabilizer of the urothelial apical surface. Wu et al. (1994) *J. Biol. Chem.* 269:13716–13724. UPs are bladder-specific proteins, and are expressed on a significant proportion of urothelial-derived tumors, including about 88% of transitional cell carcinomas. Moll et al. (1995) *Am. J. Pathol.* 147:1383–1397; and Wu et al. (1998) *Cancer Res.* 58:1291–1297. The control of the expression of the human UPII has been studied, and a 3.6-kb region upstream of the mouse UPII gene has been identified which can confer urothelial-specific transcription on heterologous genes (Lin et al. (1995)*Proc. Natl. Acad. Sci. USA* 92:679–683). See also, U.S. Pat. Nos. 5,824,543 and 6,001,646.

Of particular interest is development of more specific, targeted forms of cancer therapy, especially in cancers that are difficult to treat successfully, such as bladder cancer. In contrast to conventional cancer therapies, which result in relatively non-specific and often serious toxicity, more specific treatment modalities attempt to inhibit or kill malignant cells selectively while leaving healthy cells intact.

One possible treatment approach for cancers such as bladder cancer is gene therapy, whereby a gene of interest is introduced into the malignant cell. A variety of viral and non-viral (e.g., liposomes) vehicles, or vectors, have been developed to transfer these genes. Of the viruses, retroviruses, herpes simplex virus, adeno-associated virus, Sindbis virus, poxvirus, and adenoviruses have been proposed for gene transfer with retrovirus vectors or adenovirus vectors being the focus of much current research. Adenoviruses are among the most easily produced and purified, whereas retroviruses are unstable, difficult to produce and to purify, and may integrate into the host genome, raising the possibility of dangerous mutations. Moreover, adenovirus has the advantage of effecting high efficiency of transduction and does not require cell proliferation for efficient transduction of cell. For general background references regarding adenovirus and development of adenoviral vector systems, see Graham et al. (1973) *Virology* 52:456–467; Takiff et al. (1981) *Lancet* 11:832–834; Berkner et al. (1983) *Nucleic Acid Research* 11: 6003–6020; Graham (1984) *EMBO J* 3:2917–2922; Bett et al. (1993) *J. Virology* 67:5911–5921; and Bett et al. (1994) *Proc. Natl. Acad. Sci. USA* 91:8802–8806.

When used as gene transfer vehicles, adenovirus vectors are often designed to be replication-defective and are thus deliberately engineered to fail to replicate in the target cells of interest. In these vehicles, the early adenovirus gene products E1A and/or E1B are deleted and provided in trans by the packaging cell line 293. Graham et al. (1987) *J. Gen. Virol* 36:59–72; Graham (1977) *J. Genetic Virology* 68:937–940. The gene to be transduced is commonly inserted into adenovirus in the E1A and E1B region of the virus genome. Bett et al. (1994). Replication-defective adenovirus vectors as vehicles for efficient transduction of genes have been described by, inter alia, Stratford-Perricaudet (1990) *Human Gene Therapy* 1:241–256; Rosenfeld (1991) *Science* 252:431–434; Wang et al. (1991) *Adv. Exp. Med. Biol.* 309:61–66; Jaffe et al. (1992) *Nat. Gen.* 1:372–378; Quantin et al. (1992) *Proc. Natl. Acad. Sci. USA* 89:2581–2584; Rosenfeld et al. (1992) *Cell* 68:143–155; Stratford-Perricaudet et al. (1992) *J. Clin. Invest.* 90:626–630; Le Gal Le Salle et al. (1993) *Science*

259:988–990 Mastrangeli et al. (1993) *J. Clin. Invest.* 91:225–234; Ragot et al. (1993) *Nature* 361:647–650; Hayaski et al. (1994) *J. Biol. Chem.* 269:23872–23875; Bett et al. (1994). Adenovirus E1A and E1B genes are disclosed in Rao et al. (1992, *Proc. Natl. Acad. Sci.* USA vol. 89: 7742–7746).

Until recently, the virtually exclusive focus in development of adenoviral vectors for gene therapy has been use of adenovirus merely as a vehicle for introducing the gene of interest, not as an effector in itself. Replication of adenovirus had previously been viewed as an undesirable result, largely due to the host immune response. More recently, however, the use of adenovirus vectors as effectors has been described. International Patent Application Nos. PCT/US98/04084, PCT/US98/04133, PCT/US98/04132, PCT/US98/16312, PCT/US95/00845, PCT/US96/10838, PCT/EP98/07380, U.S. Pat. Nos. 5,998,205, and 5,698,443.

In the treatment of cancer by replication-defective adenoviruses, the host immune response limits the duration of repeat doses at two levels. First, the capsid proteins of the adenovirus delivery vehicle itself are immunogenic. Second, viral late genes are frequently expressed in transduced cells, eliciting cellular immunity. Thus, the ability to repeatedly administer cytokines, tumor suppressor genes, ribozymes, suicide genes, or genes which convert prodrug to an active drug has been limited by the immunogenicity of both the gene transfer vehicle and the viral gene products of the transfer vehicle as well as the transient nature of gene expression.

There is a need for vector constructs that are capable of eliminating essentially all cancerous cells in a minimum number of administrations before specific immunological response against the vector prevents further treatment.

All publications cited herein are hereby incorporated by reference in their entirety.

SUMMARY OF THE INVENTION

The present invention provides urothelial cell specific transcriptional regulatory sequences which regulate expression of the human uroplakin II (hUPII) gene, which can form part of an hUPII transcriptional regulatory element (hUPII-TRE). An hUPII-TRE in turn can be operably linked to a heterologous polynucleotide to effect transcriptional control of the linked gene.

The present invention provides vectors comprising an hUPII-TRE operably linked to a heterologous polypeptide which can be used to effect transcriptional control of the linked polypeptide in cells that respond to the hUPII-TRE. In particular, replication-competent adenoviral vectors specific for urothelial cells and methods for their use are also provided. In these replication-competent adenovirus vectors, one or more genes, preferably adenoviral genes, is under transcriptional control of a urothelial cell-specific transcriptional response element (TRE). Preferably, the adenoviral gene under transcriptional control of a urothelial cell-specific TRE is one that is essential for adenoviral propagation. A transgene under control of the urothelial cell-specific TRE may also be present.

Accordingly, the invention provides an isolated polynucleotide comprising 200 contiguous nucleotides of nucleotides 1 to 2239 of SEQ ID NO:1, preferably comprising bases about 2023 to about 2239 of SEQ ID NO:1 (but not depicted in SEQ ID NO:2), and having urothelial cell-specific TRE activity. The present invention also provides an isolated polynucleotide comprising 200 contiguous nucleotides of nucleotides 430 to 2239 of SEQ ID NO:1, preferably comprising bases about 2023 to about 2239 of SEQ ID NO:1 (but not depicted in SEQ ID NO:2), and having urothelial cell-specific TRE activity. In another aspect, the invention provides an isolated polynucleotide comprising 200 contiguous nucleotides having at least about 70%, more preferably at least about 75%, 80%, 85%, 90%, 95%, 98% or 99%, sequence identity to a sequence within nucleotides 1 to 2239 of SEQ ID NO:2 (but not depicted in SEQ ID NO:1), with the polynucleotide having urothelial cell-specific TRE activity. In another aspect, the invention provides an isolated polynucleotide comprising a region of at least 20 contiguous nucleotides, with the region able to hybridize under stringent conditions to a polynucleotide comprising nucleotides about 1 to about 2239, about 430 to about 2239, about 2038 to about 2239, and/or about 1647 to about 2239 of SEQ ID NO:1, with the polynucleotide having urothelial cell-specific TRE activity (and not depicted in SEQ ID NO:2).

In another aspect, the invention provides an isolated polynucleotide comprising at least about 20 nucleotides which hybridize under stringent conditions to a region of SEQ ID NO:1, wherein the region is nucleotides about 1 to about 2239 of SEQ ID NO:1 or a complementary sequence thereof, wherein the at least about 20 nucleotides are not depicted in SEQ ID NO:2. In another aspect, the invention provides an isolated polynucleotide comprising at least about 20 nucleotides which hybridize under stringent conditions to a region of SEQ ID NO:1, wherein the region is nucleotides about 430 to about 2239 of SEQ ID NO:1 or a complementary sequence thereof, wherein the at least about 20 nucleotides are not depicted in SEQ ID NO:2. In various embodiments, the regions are nucleotides about 2028 to about 2239, about 430 to about 2239, about 1647 to about 2239, or about 1223 to about 2239 of SEQ ID NO:1.

In another aspect, the invention provides isolated polynucleotides of at least 20 contiguous nucleotides of SEQ ID NO:1.

In another aspect, the invention provides isolated polynucleotides comprising a transcriptional regulatory element which comprises a hUPII 5'-flanking polynucleotide sequence which confers urothelial cell-specific transcription on heterologous polynucleotide sequences.

The invention also provides vectors and/or delivery vehicles containing these hUPII urothelial cell-specific TRE polynucleotide(s). Such vectors and/or delivery vehicles can be introduced into cells both in vivo and in vitro.

In another aspect, the invention provides adenovirus vectors comprising co-transcribed first and second genes under control of a urothelial cell-specific TRE, wherein the second gene is under translational control of an internal ribosome entry site (IRES).

The invention also provides methods for introducing into a cell a vector and/or a delivery vehicle containing hUPII urothelial cell-specific TRE polynucleotide(s). The invention further provides host cells containing hUPII urothelial cell-specific TRE polynucleotide(s).

In other aspects, the invention provides methods of creating constructs comprising hUPII urothelial cell-specific TRE polynucleotide(s) operably linked to a heterologous polynucleotide and further provides methods for increasing the transcription and/or expression of the linked heterologous polynucleotide generally involving introducing the constructs into suitable cells.

Accordingly, the invention provides methods for increasing transcription of polynucleotide sequence in a cell comprising introducing a construct comprising hUPII urothelial cell-specific TRE polynucleotide(s) operably linked to said polynucleotide into a cell in which said hUPII urothelial cell-specific TRE polynucleotide(s) is functional.

In another aspect, the invention provides an adenovirus vector comprising an adenovirus gene under transcriptional control of a urothelial cell-specific TRE. In another embodiment, a urothelial cell-specific TRE is human. In another embodiment, a urothelial cell-specific TRE comprises a urothelial cell-specific promoter and a heterologous enhancer. In other embodiments, a urothelial cell-specific TRE comprises a urothelial cell-specific promoter. In other embodiments, a urothelial cell-specific TRE comprises a urothelial cell-specific enhancer and a heterologous promoter. In other embodiments, a urothelial cell-specific TRE comprises a urothelial cell-specific promoter and a urothelial cell-specific enhancer.

In some embodiments, the adenovirus gene under transcriptional control of a urothelial cell-specific TRE is an adenovirus gene essential for replication. In some embodiments, the adenoviral gene essential for replication is an early gene. In another embodiment, the early gene is E1A. In another embodiment, the early gene is E1B. In yet another embodiment, both E1A and E1B are under transcriptional control of a urothelial cell-specific TRE. In other embodiments, the adenovirus gene essential for replication is a late gene.

In some embodiments, the urothelial cell-specific TRE is derived from the 5' flanking region of a uroplakin gene. In some of these embodiments, the urothelial cell-specific TRE is derived from the 5' flanking region of a UPIa gene. In other embodiments, the urothelial cell-specific TRE is derived from the 5'-flanking region of a UPIb gene. In yet other embodiments, the urothelial cell-specific TRE is derived from the 5'-flanking region of a UPII gene. In yet other embodiments, the urothelial cell-specific TRE is derived from the 5'-flanking region of a UPIII gene.

In other embodiments, the invention provides an adenovirus vector comprising (a) an adenovirus gene under transcriptional control of a urothelial cell-specific TRE; and (b) an E3 region. In some of these embodiments the E3 region is under transcriptional control of a urothelial cell-specific TRE.

In another aspect, the invention provides a host cell comprising the adenovirus vector(s) described herein.

In another aspect, the invention provides pharmaceutical compositions comprising an adenovirus vector(s) described herein.

In another aspect, the invention provides kits which contain an adenoviral vector(s) described herein.

In another aspect, methods are provided for conferring selective cytotoxicity in target cells (i.e., cells which permit or induce a urothelial cell-specific TRE to function), comprising contacting the cells with an adenovirus vector(s) described herein, whereby the vector enters the cell.

In another aspect, methods are provided for propagating an adenovirus specific for urothelial cells, said method comprising combining an adenovirus vector(s) described herein with urothelial cells, whereby said adenovirus is propagated.

The invention further provides methods of suppressing bladder cancer cell growth, comprising contacting a bladder cancer cell with an adenoviral vector of the invention such that the adenoviral vector enters the bladder cancer cell and exhibits selective cytotoxicity for the bladder cancer cell.

In another aspect, methods are provided for detecting bladder cancer cells in a biological sample, comprising contacting cells of a biological sample with an adenovirus vector(s) described herein, and detecting replication of the adenovirus vector, if any.

BRIEF DESCRIPTION OF THE DRAWINGS

FIGS. 1A–1C (SEQ ID NO:1) depicts a nucleotide sequence of a human uroplakin II 5' flanking region. Position +1 (the translational start site) is denoted with an asterisk (in FIG. 1A, nucleotide number 1 represents nucleotide −2239; nucleotide number 430 represents nucleotide −1809).

FIGS. 2A–2E depicts a nucleotide sequence of a mouse uroplakin II 5' flanking region. With respect to the translational start site, nucleotide number 1 represents nucleotide −3592).

FIGS. 4A–4G are a series of schematic depictions of various adenoviral constructs described herein.

FIG. 12 provides a nucleic acid and amino acid sequence for ADP (SEQ ID NOs:3 and 4).

MODES FOR CARRYING OUT THE INVENTION

Figure 3A:
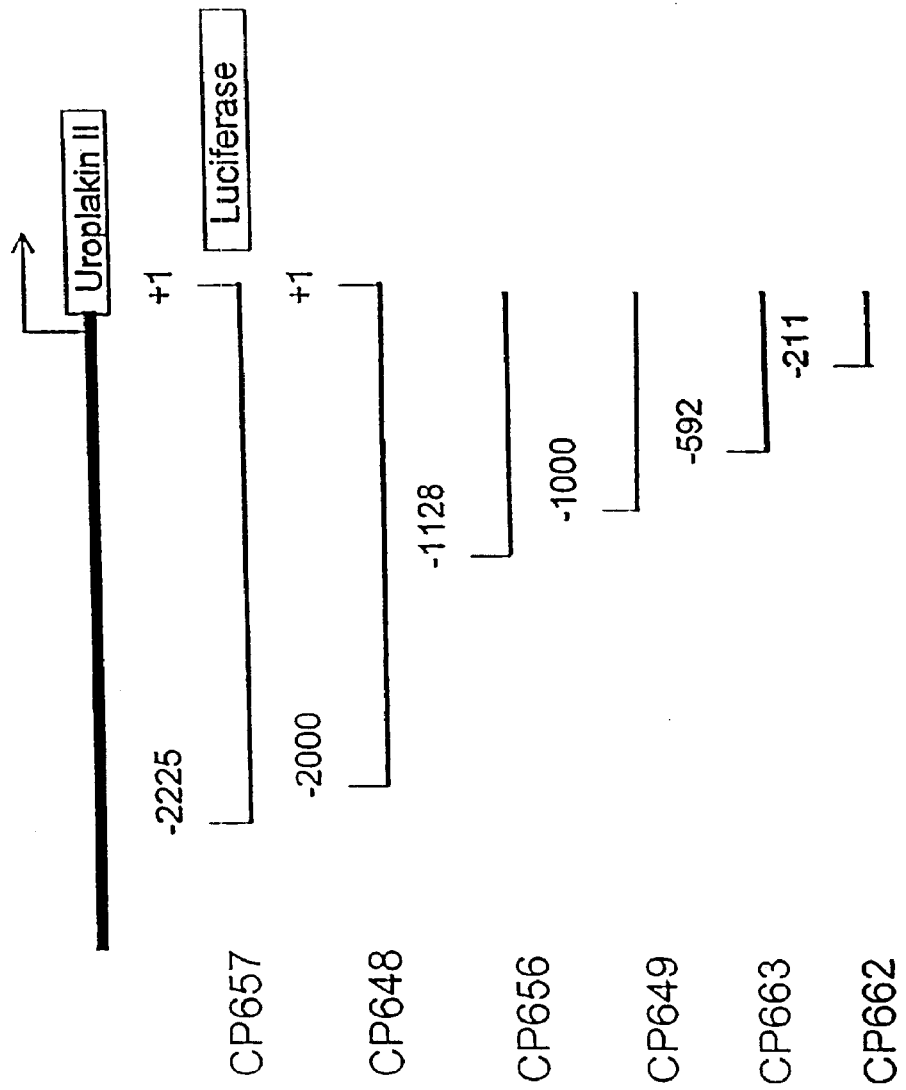
FIGS. 3A–3B are a series of schematic depictions of various plasmid constructs described herein.

We have isolated and characterized a 2.2 kb 5'-flanking DNA sequence of the human uroplakin gene and a 1.8 kb 5'-flanking DNA sequence of the human uroplakin gene both of which regulate, in a tissue-specific manner, transcription of human uroplakin II (hUPII; FIG. 1 (SEQ ID NO:1)). The hUPII 5'-flanking DNA of the invention confers urothelial cell-specific expression on heterologous DNA sequences. Additionally, we have found fragments of hUPII 5'-flanking DNA (comprising bases about 2028 to about 2239 shown in FIG. 1 (SEQ ID NO:1)) that also confer urothelial cell-specific expression on heterologous DNA sequences. The hUPII 5'-flanking DNA and fragments thereof disclosed herein can act as a urothelial cell-specific TREs and/or can be included in a urothelial cell-specific TRE. Fragments of hUPII 5'-flanking DNA disclosed herein are particularly advantageous for use in vector systems where insert size is limited, such as most viral vector systems.

An urothelial cell-specific TRE, such as one comprising the hUPII 5'-flanking DNA sequence or fragment thereof disclosed herein is useful for effecting cell-specific expression, for example, in urothelial cells of urinary tract, thus enabling the directed expression of a desired gene in these cells. For example, vector constructs comprising a heterologous polynucleotide under the transcriptional control of an urothelial cell-specific TRE comprising hUPII 5'-flanking DNA can be introduced into bladder cancer cells (particularly transitional cell carcinoma cells) wherein the heterologous polynucleotide encodes a product which is inhibitory to cell growth, thus controlling the growth of the cancerous cells.

We have also discovered and constructed replication-competent adenovirus vectors which contain an adenovirus gene under transcriptional control of a urothelial cell-specific TRE such that the adenovirus gene is transcribed preferentially in urothelial cells, and have developed methods using these adenovirus vectors. In some preferred embodiments, the adenovirus vectors of this invention comprise at least one adenovirus gene necessary for adenoviral replication, preferably at least one early gene, under the transcriptional control of a TRE. In other preferred embodiments, the adenovirus vectors of this invention comprise co-transcribed first and second genes under control of a urothelial cell-specific TRE, wherein the second gene is under translational control of an internal ribosome entry site (IRES). For adenovirus vectors comprising a second gene under control of an IRES, it is preferred that the endogenous promoter of a gene under translational control of an IRES be deleted so that the endogenous promoter does not interfere with transcription of the second gene. It is preferred that the second gene be in frame with the IRES if the IRES contains an initiation codon. If an initiation codon, such as ATG, is present in the IRES, it is preferred that the initiation codon of the second gene be removed so that the IRES and second gene are in frame. Alternatively, if the IRES does not contain an initiation codon or if the initiation codon is removed from the IRES, the initiation codon of the second gene is used. By providing for urothelial cell-specific transcription of at least one adenovirus gene required for replication, the invention provides adenovirus vectors that can be used for specific cytotoxic effects due to selective replication and/or selective transcription. This is especially useful in the cancer context, in which targeted cell killing is desirable. This is also useful for targeted cytotoxic effects in other, non-tumor cells, when selective destruction and/or suppression of these cells is desirable. The vectors can also be useful for detecting the presence of cells which permits function of a urothelial cell-specific TRE in, for example, an appropriate biological (such as clinical) sample. Further, the adenovirus vector(s) can optionally selectively produce one or more proteins of interest in a target urothelial cell by using a urothelial cells-specific TRE.

Adenovirus vectors of the invention replicate and/or express an adenoviral gene operably linked to a urothelial cell-specific TRE preferentially in cells which permits the function of a urothelial cell-specific TRE.

The adenovirus vectors of the present invention comprise a urothelial cell-specific TRE which is functional in a target urothelial cell. The replication preference of these vectors is indicated by comparing the level of replication (i.e., titer) in another, non-urothelial cell type(s). Thus, the invention also uses and takes advantage of what has been considered an undesirable aspect of adenoviral vectors, namely, their replication and possibly concomitant immunogenicity. The probability of runaway infection is significantly reduced due to the urothelial cell-specific requirements for viral replication. Without wishing to be bound by any particular theory, the inventors note that production of adenovirus proteins can serve to activate and/or stimulate the immune system, generally and/or specifically toward target cells producing adenoviral proteins, which can be an important consideration in the cancer context, where patients are often moderately to severely immunocompromised.

The adenovirus vectors of the present invention find particular utility in inter alia specific treatment regimens, in which the treatment is highly focused toward bladder cancer which might otherwise be inoperable or untreatable. They are also useful for conferring selective cytotoxicity as well as detection.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (J. M. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodic updates); "PCR: The Polymerase Chain Reaction", (Mullis et al., eds., 1994); "Current Protocols in Immunology" (J. E. Coligan et al., eds., 1991).

For techniques related to adenovirus, see, inter alia, Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Definitions

As used herein, a "transcription response element" or "transcriptional regulatory element", or "TRE" is a polynucleotide sequence, preferably a DNA sequence, which increases transcription of an operably linked polynucleotide sequence in a host cell that allows that TRE to function. A TRE can comprise an enhancer and/or a promoter. A "transcriptional regulatory sequence" is a TRE.

As used herein, a "urothelial cell-specific transcriptional response element", or "urothelial cell-specific TRE" is polynucleotide sequence, preferably a DNA sequence, which increases transcription of an operably linked polynucleotide sequence in a host cell that allows a urothelial-specific TRE to function, i.e., a target cell. A variety of urothelial cell-specific TREs are known, are responsive to cellular proteins (transcription factors and/or co-factor(s)) associated with urothelial cells, and comprise at least a portion of a urothelial-specific promoter and/or a urothelial-specific enhancer. Methods are described herein for measuring the activity of a urothelial cell-specific TRE and thus for determining whether a given cell allows a urothelial cell-specific TRE to function.

As described in more detail herein, a urothelial cell-specific TRE can comprise any number of configurations, including, but not limited to, a urothelial cell-specific promoter; a urothelial cell-specific enhancer; a urothelial cell-specific promoter and a urothelial cell-specific enhancer; a urothelial cell-specific promoter and a heterologous enhancer; a heterologous promoter and a urothelial cell-specific enhancer; and multimers of the foregoing. The promoter and enhancer components of a urothelial cell-specific TRE may be in any orientation and/or distance from the coding sequence of interest, as long as the desired urothelial cell-specific transcriptional activity is obtained. Transcriptional activation can be measured in a number of ways known in the art (and described in more detail below), but is generally measured by detection and/or quantitation of mRNA or the protein product of the coding sequence under control of (i.e., operably linked to) the urothelial cell-specific TRE. As discussed herein, a urothelial cell-specific TRE can be of varying lengths, and of varying sequence composition.

A "functional portion" of a urothelial cell-specific TRE is one which confers urothelial cell-specific transcription on an operably linked gene or coding region, such that the operably linked gene or coding region is preferentially expressed in urothelial cells.

A polynucleotide which has or exhibits "urothelial cell-specific activity" increases transcription of an operably linked polynucleotide in a suitable host cell, such as a urothelial cell, preferably a human urothelial cell.

By "transcriptional activation" or an "increase in transcription," it is intended that transcription is increased above basal levels in the target cell (i.e., urothelial cell) by at least about 2 fold, preferably at least about 5 fold, preferably at least about 10 fold, more preferably at least about 20 fold, more preferably at least about 50 fold, more preferably at least about 100 fold, more preferably at least about 200 fold, even more preferably at least about 400 fold to about 500 fold, even more preferably at least about 1000 fold. Basal levels are generally the level of activity (if any) in a non-urothelial cell (i.e., a different cell type), or the level of activity (if any) of a reporter construct lacking a urothelial cell-specific TRE as tested in a urothelial, e.g., a bladder carcinoma cell line.

"Replicating preferentially", as used herein, means that the virus of interest, e.g., an adenovirus adenovirus replicates more in a urothelial cell than a non-urothelial cell. Preferably, the virus replicates at a significantly higher rate in urothelial cells than non urothelial cells; preferably, at least about 2-fold higher, preferably, at least about 5-fold higher, more preferably, at least about 10-fold higher, still more preferably at least about 50-fold higher, even more preferably at least about 100-fold higher, still more preferably at least about 400- to 500-fold higher, still more preferably at least about 1000-fold higher, most preferably at least about $1 \times 10^6$ higher. Most preferably, the vector replicates solely in urothelial cells (that is, does not replicate or replicates at a very low levels in non-urothelial cells).

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

An "adenovirus vector" or "adenoviral vector" (used interchangeably) comprises a polynucleotide construct of the invention. A polynucleotide construct of this invention may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a nonviral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1 996) *Nucleic Acids Res.* 24: 2966–73. A phosphorothioate linkage can be used in place of a phosphodiester linkage. Braun et al. (1988) *J. Immunol.* 141: 2084–9; Latimer et al. (1995) *Molec. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence. As used herein, an "isolated polynucleotide" means that the polynucleotide is removed from at least one component with which it is naturally associated.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18, Table 7.7.1. A preferred alignment program is ALIGN Plus (Scientific and Educational Software, Pennsylvania), preferably using default parameters, which are as follows: mismatch=2; open gap=0; extend gap=2.

"Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

An "E3 region" (used interchangeably with "E3") is a term well understood in the art and means the region of the adenoviral genome that encodes the E3 products (discussed herein). Generally, the E3 region is located between about 28583 and 30470 of the adenoviral genome. The E3 region has been described in various publications, including, for example, Wold et al. (1995) *Curr. Topics Microbiol. Immunol.* 199:237–274.

A "portion" of the E3 region means less than the entire E3 region, and as such includes polynucleotide deletions as well as polynucleotides encoding one or more polypeptide products of the E3 region.

An "E1B 19-kDa region" (used interchangeably with "E1B 19-kDa genomic region") refers to the genomic region of the adenovirus E1B gene encoding the E1B 19-kDa product. According to wild-type Ad5, the E1B 19-kDa region is a 261 bp region located between nucleotide 1714 and nucleotide 2244. The E1B 19-kDa region has been described in, for example, Rao et al., *Proc. Natl. Acad. Sci. USA*, 89:7742–7746. The present invention encompasses deletion of part or all of the E1B 19-kDa region as well as embodiments wherein the E1B 19-kDa region is mutated, as long as the deletion or mutation lessens or eliminates the inhibition of apoptosis associated with E1B-19kDa.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. Jackson R J, Howell M T, Kaminski A (1990) *Trends Biochem Sci* 15(12):477–83) and Jackson R J and Kaminski, A. (1995) *RNA* 1(10):985–1000). The present invention encompasses the use of any IRES element which is able to promote direct internal ribosome entry to the initiation codon of a cistron. "Under translational control of an IRES" as used herein means that translation is associated with the IRES and proceeds in a cap-independent manner. Examples of "IRES" known in the art include, but are not limited to IRES obtainable from picornavirus (Jackson et al., 1990, *Trends Biochem Sci* 15(12):477–483); and IRES obtainable from viral or cellular mRNA sources, such as for example, immunogloublin heavy-chain binding protein (BiP), the vascular endothelial growth factor (VEGF) (Huez et al. (1998) *Mol. Cell. Biol.* 18(11):6178–6190), the fibroblast growth factor 2, and insulin-like growth factor, the translational initiation factor eIF4G, yeast transcription factors TFIID and HAP4. IRES have also been reported in different viruses such as cardiovirus, rhinovirus, aphthovirus, HCV, Friend murine leukemia virus (FrMLV) and Moloney murine leukemia virus (MoMLV). As used herein, "IRES" encompasses functional variations of IRES sequences as long as the variation is able to promote direct internal ribosome entry to the initiation codon of a cistron. In preferred embodiments, the IRES is mammalian. In other embodiments, the IRES is viral or protozoan. In one illustrative embodiment disclosed herein, the IRES is obtainable from encephelomycarditis virus (ECMV) (commercially available from Novogen, Duke et al. (1992) *J. Virol* 66(3):1602–1609). In another illustrative embodiment disclosed herein, the IRES is from VEGF. Table 6 and Table 7 disclose a variety of IRES sequences useful in the present invention.

In some embodiments, an adenovirus vector comprising co-transcribed first and second genes under transcriptional control of a urothelial-TRE wherein an IRES controls translation of the second gene may exhibit greater specificity for the target cell, ie, bladder cell, than an adenovirus vector comprising a urothelial TRE operably linked to a gene and lacking an IRES. In some embodiments, specificity is conferred by preferential transcription and/or translation of the first and second genes due to the presence of a urothelial TRE. In other embodiments, specificity is conferred by preferential replication of the adenovirus vectors in target cells due to the urothelial TRE driving transcription of a gene essential for replication.

A "multicistronic transcript" refers to an mRNA molecule which contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the MRNA. The terms "5'-distal" and "downstream" are used synonymously to refer to coding regions that are not adjacent to the 5' end of a mRNA molecule.

As used herein, "co-transcribed" means that two (or more) coding regions of polynucleotides are under transcriptional control of single transcriptional control element.

A "gene" refers to a coding region of a polynucleotide. A "gene" may or may not include non-coding sequences and/or regulatory elements.

"Replication" and "propagation" are used interchangeably and refer to the ability of a polynucleotide construct of the invention to reproduce, or proliferate. This term is well understood in the art. For purposes of this invention, replication involves production of adenovirus proteins and is generally directed to reproduction of adenovirus. Replication can be measured using assays standard in the art and described herein, such as a burst assay, plaque assay, or a one-step growth curve assay.

As used herein, "cytotoxicity" is a term well understood in the art and refers to a state in which a cell's usual biochemical or biological activities are compromised (i.e., inhibited). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, $^3$H-thymidine uptake, and plaque assays.

The term "selective cytotoxicity", as used herein, refers to the cytotoxicity conferred by an adenovirus vector of the present invention on a cell which allows or induces a urothelial cell-specific TRE to function (a target cell) when compared to the cytotoxicity conferred by an adenoviral vector of the present invention on a cell which does not allow a urothelial cell-specific TRE to function (a non-target cell). Such cytotoxicity may be measured, for example, by plaque assays, by reduction or stabilization in size of a tumor comprising target cells, or the reduction or stabilization of serum levels of a marker characteristic of the tumor cells, or a tissue-specific marker, e.g., a cancer marker.

In the context of adenovirus, a "heterologous polynucleotide" or "heterologous gene" or "transgene" is any polynucleotide or gene that is not present in wild-type adenovirus. Preferably, the transgene will also not be expressed or present in the target cell prior to introduction by the adenovirus vector. Examples of preferred transgenes are provided below.

In the context of adenovirus, a "heterologous" promoter or enhancer is one which is not associated with or derived from an adenovirus gene.

In the context of adenovirus, an "endogenous" promoter, enhancer, or TRE is native to or derived from adenovirus. In the context of promoter, an "inactivation" means that there is a mutation of or deletion in part or all of the of the endogenous promoter, ie, a modification or alteration of the endogenous promoter, such as, for example, a point mutation or insertion, which disables the function of the promoter.

In the context of a urothelial cell-specific TRE, a "heterologous" promoter or enhancer is one which is derived from a gene other than the gene from which a reference urothelial cell-specific TRE is derived. Examples of a heterologous promoter with respect to the reference mouse UPII promoter include a viral promoter, an enhancer from a uroplakin gene other than mouse UPII, and a hypoxia-responsive element. "Suppressing" tumor growth indicates a growth state that is curtailed when compared to growth without contact with, i.e., transfection by, an adenoviral vector described herein. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation (i.e., de-regulated cell division). Neoplastic cells can be malignant or benign.

A "host cell" includes an individual cell or cell culture which can be or has been a recipient of an adenoviral vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

"Replication" and "propagation" are used interchangeably and refer to the ability of an adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

An "ADP coding sequence" is a polynucleotide that encodes ADP or a functional fragment thereof. In the context of ADP, a "functional fragment" of ADP is one that exhibits cytotoxic activity, especially cell lysis, with respect to adenoviral replication. Ways to measure cytotoxic activity are known in the art and are described herein.

A polynucleotide that "encodes" an ADP polypeptide is one that can be transcribed and/or translated to produce an ADP polypeptide or a fragment thereof. The anti-sense strand of such a polynucleotide is also said to encode the sequence.

An "ADP polypeptide" is a polypeptide containing at least a portion, or region, of the amino acid sequence of an ADP (see, for example, SEQ ID NO:4), and which displays a function associated with ADP, particularly cytotoxicity, more particularly, cell lysis. As discussed herein, these functions can be measured using techniques known in the art. It is understood that certain sequence variations may be used, due to, for example, conservative amino acid substitutions, which may provide ADP polypeptides.

A polynucleotide sequence that is "depicted in" a SEQ ID NO means that the sequence is present as an identical contiguous sequence in the SEQ ID NO. The term encompasses portions, or regions, of the SEQ ID NO as well as the entire sequence contained within the SEQ ID NO.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, rodents, primates, and pets.

An "effective amount" is an amount sufficient to effect beneficial or desired results, including clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

A given TRE is "derived from" a given gene if it is associated with that gene in nature.

"Expression" includes transcription and/or translation.

As used herein, the term "comprising" and its cognates are used in their inclusive sense; that is, equivalent to the term "including" and its corresponding cognates.

"A," "an" and "the" include plural references unless the context clearly dictates otherwise.

Human Uroplakin Transcriptional Regulatory Sequences

The present invention provides isolated polynucleotide sequences, derived from the hUPII gene, that act to increase the transcription of operably linked polynucleotides in a cell-specific manner. These sequences are of use in controlling the transcription of polynucleotide sequences to which they are operably linked, and thus they may also lend a level of control to the expression of heterologous polynucleotides. These sequences, or a transcriptional regulatory element which they form, can be characterized, in part, by being linked to a polynucleotide sequence, the expression of which they regulate.

Accordingly, the present invention encompasses hUPII transcriptional control polynucleotides, vectors containing these polynucleotides, host cells containing these polynucleotides, and compositions comprising these polynucleotides. These polynucleotides are isolated and/or produced by chemical and/or recombinant methods, or a combination of these methods. Unless specifically stated otherwise, "polynucleotides" shall include all embodiments of the polynucleotide of this invention. These polynucleotides are useful as probes, primers, in expression systems, and in screening methods as described herein.

It is understood that all polynucleotide embodiments described in this section ("Human uroplakin transcriptional regulatory sequences") are not depicted in SEQ ID NO:2 (i.e., in any and all of these embodiments, the contiguous nucleotides are not depicted in SEQ ID NO:2 (FIG. 2)). A BLAST search of nucleotides 1 to 2239 (match 1; mismatch −2; gap open 5; gap extension 2) revealed that the sequence spanning from 1 to 2239 of SEQ ID NO:1 shares approximately 81% nucleotide sequence identity over nucleotides 2012 to 2225 of SEQ ID NO:1 with mouse uroplakin II transcriptional regulatory sequences. The longest contiguous identical nucleotide sequence was 16 nucleotides.

We have identified fragments of the human UPII (hUPII) 5′ untranslated region (UTR) which confer urothelial cell-specific expression on heterologous genes. An approximately 2.2 kb fragment has been isolated (FIG. 1, SEQ ID NO:1) from the 5′ UTR of the hUPII gene which confers high level, urothelial cell-specific expression on heterologous genes. Additionally, we have shown that a 1.0 kb fragment (nucleotides 1223 to 2239 of SEQ ID NO:1) of the 5′ UTR sequence of the hUPII gene, a 200 bp fragment (nucleotides 2028–2239 of SEQ ID NO:1), a 600 bp fragment (nucleotides 1647–2239 of SEQ ID NO:1), and a 1809 bp fragment (nucleotides 430–2239 of SEQ ID NO:1) confer urothelial cell-specific expression on heterologous genes.

Accordingly, the invention includes an isolated polynucleotide comprising nucleotides about 2028 to about 2239 of SEQ ID NO:1), wherein the polynucleotide exhibits urothelial cell-specific TRE activity (i.e., increases transcription of an operably linked polynucleotide in a suitable host cell, such as a urothelial cells, preferably a human urothelial cell). In other embodiments, the isolated polynucleotide comprises nucleotides about 1223 to about 2239, about 1647 to about 2239, about 430 to about 2239, or about 1 to about 2239 of SEQ IDf NO:1, wherein the polynucleotide exhibits urothelial cell specific TRE activity.

In other embodiments, the invention provides an isolated polynucleotide comprising 200 contiguous nucleotides of SEQ ID NO:1 (FIG. 1), wherein the polynucleotide exhibits urothelial cell specific TRE activity. In some embodiments, the contiguous nucleotides are within nucleotides about 2028 to about 2239 of SEQ ID NO:1 (but not depicted in SEQ ID NO:2). In other embodiments, the at least 200 contiguous nucleotides are nucleotides within about 1647 to about 2239, about 1223 to about 2239, about 430 to about 2239, or about 1 to about 2239 of SEQ ID NO:1.

In another embodiment, the invention provides an isolated polynucleotide comprising 200 contiguous nucleotides having at least about 70%, more preferably at least about 75%, 80%, 85%, 90%, 95%, 98% or 99%, sequence identity to a sequence within nucleotides 1 to 2239 of SEQ ID NO:1, with the polynucleotide having urothelial cell-specific TRE activity. In other embodiments, the invention provides an isolated polynucleotide comprising 200 contiguous nucleotides having at least about 70%, more preferably at least about 75%, 80%, 85%, 90%, 95%, 98% or 99%, sequence identity to a sequence within nucleotides 430 to 2239 of SEQ ID NO:1, with the polynucleotide having urothelial cell-specific TRE activity. Various contiguous nucleotides have been provided above, and are included in these embodiments. As noted above, such activity may be found in various lengths of SEQ ID NO:1 (as well as in various regions of SEQ ID NO:1), and may thus also have a longer contiguous nucleotide sequence. In any and all of these embodiments, it is understood that the contiguous nucleotides are not depicted in SEQ ID NO:2. A preferred alignment program (with parameters) is ALIGN Plus (Scientific and Educational Software, Pennsylvania), preferably using efault parameters, which are as follows: mismatch=2; open gap=0; extend gap=2.

An hUPII transcriptional regulatory sequence of the invention may be about 100 contiguous nucleotides, about 150, 200, 250, 300, 350, 400, 450, 500, 550, 600, 700, 800, 900, 1000, 1200, 1500, 1700, 2000 contiguous nucleotides or larger of the sequence depicted in nucleotides 1 to 2239 of SEQ ID NO:1. Methods for identifying an hUPII transcriptional control sequence are routine and well known in the art. For example, overlapping sequences of an hUPII transcriptional control sequence can be synthesized and cloned into the vector described in Example 1 to determine hUPII transcriptional control activity. Similarly, point mutations can be introduced into the disclosed hUPII enhancer sequences using, for example, site-directed mutagenesis or by synthesizing sequences having random nucleotides at one or more predetermined positions and hUPII transcriptional control sequence activity determined.

As an example of how hUPII transcriptional control activity can be determined, a polynucleotide sequence or set of such sequences can be generated using methods known in the art, such as chemical synthesis, site-directed mutagenesis, PCR, and/or recombinant methods. The sequence(s) to be tested can be inserted into a vector containing a promoter and an appropriate reporter gene encoding a reporter protein, including, but not limited to, chloramphenicol acetyl transferase (CAT), β-galactosidase (encoded by the lacZ gene), luciferase, (encoded by the luc gene), alkaline phosphatase, green fluorescent protein, and horse radish peroxidase. Such vectors and assays are readily available, from, inter alia, commercial sources. Plasmids thus constructed are transfected into a suitable host cell to test for expression of the reporter gene as controlled by the putative hUPII transcriptional regulatory sequence using transfection methods known in the art, such as calcium phosphate precipitation, electroporation, liposomes (lipofection), and DEAE dextran.

In other embodiments, the isolated polynucleotide (of at least any of the lengths specified above) comprises a region of at least 20 contiguous nucleotides, wherein said region hybridizes under stringent conditions to any of the following regions (i.e., contiguous nucleotides) of SEQ ID NO:1: about 2028 to about 2239; about 1647 to about 2239; about 1223 to about 2239; about 430 to about 2239, about 1 to about 2239, wherein the polynucleotide has urothelial cell specific TRE activity. It is understood that these embodiments also include a polynucleotide (whether single or double stranded) which hybridizes (under stringent conditions) to the corresponding complementary sequence and/or regions of SEQ ID NO:1 as indicated above. In other embodiments, region of the isolated polynucleotide which hybridizes to a sequence of SEQ ID NO:1 is at least any of the following, in terms of contiguous nucleotides: about 25, 30, 50, 75, 100, 150, 250, 300, 350, 400, 450, 500, 750, 1000, 1500. It is understood that a polynucleotide which "hybridizes" to a sequence (region) of SEQ ID NO:1 contains one or more regions of at least 20 contiguous nucleotides which hybridize to a region of SEQ ID NO:1, and that the entire sequence of the polynucleotide which hybridizes to a region of SEQ ID NO:1 need not form a duplex.

In terms of hybridization conditions, the higher the sequence identity required, the more stringent are the hybridization conditions if such sequences are determined by their ability to hybridize to a sequence of SEQ ID NO:1. Accordingly, the invention also includes polynucleotides that are able to hybridize to a sequence comprising at least about 15 contiguous nucleotides (or more, such as about 25, 35, 50, 75 or 100 contiguous nucleotides) of SEQ ID NO:1. The hybridization conditions would be stringent, i.e., 80° C. (or higher temperature) and 6M SSC (or less concentrated SSC). Another set of stringent hybridization conditions is 68° C. and 0.1×SSC. For discussion regarding hybridization reactions, see below.

Hybridization reactions can be performed under conditions of different "stringency". Conditions that increase stringency of a hybridization reaction of widely known and published in the art. See, for example, Sambrook et al. (1989) at page 7.52. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. An exemplary set of stringent hybridization conditions is 68° C. and 0.1×SSC.

"$T_m$" is the temperature in degrees Celcius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log[X^+] + 0.41(\%G/C) - 0.61 (\%F) - 600/L$$

where [$X^+$] is the cation concentration (usually sodium ion, $Na^+$) in mol/L; (%G/C) is the number of G and C residues as a percentage of total residues in the duplex; (%F) is the percent formamide in solution (wt/vol); and L is the number of nucleotides in each strand of the duplex.

Also within the invention are isolated polynucleotides of at least about any of the following lengths, in terms of contiguous nucleotides of SEQ ID NO:1: 15, 20, 30, 100, 150, 200, 250, 300, 400, 450. These polynucleotides may be used, for example, as probes and/or primers.

An hUPII transcriptional regulatory sequence may be, or may form part of, an hUPII transcriptional regulatory element, or hUPII-TRE, which may in turn be operably linked to a heterologous polynucleotide, i.e., a gene not naturally operably linked to an hUPII-TRE. An hUPII-TRE would increase expression of an operably linked gene preferentially in those cells which allow an hUPII-TRE to function.

Examples of heterologous polynucleotides which may be operably linked to an hUPII-TRE include, but are not limited to, reporter genes, genes encoding compounds toxic to mammalian cells, genes encoding biological response modifiers, lymphokines, cytokines, cell surface antigens, synthetic genes which direct the synthesis of ribozymes or anti-sense ribonucleotides and genes encoding transcription factors.

Marker genes, or reporter genes, which may be employed are known to those skilled in the art and include, but are not limited to, luciferase; aequorian (i.e., green fluorescent protein from *Aequorea Victoria*); β-galactosidase, cthloramphenicol acetyl transferase; immunologically detectable protein "tags" such as human growth hormone; and the like. See, for example, Current Protocols in Molecular Biology (F. M. Ausubel et al., eds., 1987) and periodic updates. Any assay which detects a product of the reporter gene, either by directly detecting the protein encoded by the reporter gene or by detecting an enzymatic product of a reporter gene-encoded enzyme, is suitable for use in the present invention. Assays include colorimetric, fluorimetric, or luminescent assays or even, in the case of protein tags, radioimmunoassays or other immunological assays.

Toxin genes may include the diphtheria toxin A-chain gene, ricin A-chain gene, *Pseudomonas* exotoxin gene, etc. Maxwell et al. (1987) *Mol. Cell. Biol.* 7:1576; Frankel et al. (1989) *Mol Cell. Biol.* 9:415; Chaudhary et al. (1990) *Proc. Natl. Acad. Sci. U.S.A.* 87:4574. Such toxins are known to those skilled in the art. Other toxin genes may include mutated or truncated forms of naturally-occurring proteins which competitively or non-competitively inhibit the correct functioning of the naturally-occurring forms and which thereby may kill the cell. Alternatively, a toxin gene may comprise a gene that, when expressed, causes apoptosis.

Lymphokines and cytokines are known in the art and include, but are not limited to, interleukins, interferons, colony-stimulating factors, etc.

Cell surface antigens include those which are not normally expressed on the surface of a given cell, and result in enhance immunocytotoxicity or immune reactivity toward the cell.

Synthetic genes which direct the synthesis of ribozymes or anti-sense ribonucleotides may also be operably linked to an hUPII transcriptional regulatory, sequence. Antisense RNA and DNA molecules and ribozymes may function to inhibit translation of a protein. S. T. Crooke and B. Lebleu, eds. *Antisense Research and Applications* (1993) CRC Press; and *Antisense RNA and DNA* (1988) D. A. Melton, Ed. Cold Spring Harbor Laboratory Cold Spring Harbor, N.Y. Anti-sense RNA and DNA molecules act to directly block the translation of mRNA by binding to targeted mRNA and preventing protein translation. Ribozymes are enzymatic RNA molecules capable of catalyzing the specific cleavage of RNA. The mechanism of ribozyme action involves sequence specific interaction of the ribozyme molecule to complementary target RNA, followed by an endonucleolytic cleavage. Within the scope of the invention are engineered hammerhead or other motif ribozyme molecules that specifically and efficiently catalyze endonucleolytic cleavage of RNA sequences.

Compositions comprising an hUPII transcriptional regulatory polynucleotide as well as compositions comprising an hUPII-TRE operably linked to a heterologous polynucleotide are encompassed by this invention. When these compositions are to be used pharmaceutically, they are combined with a pharmaceutically acceptable excipient. Accordingly, the invention also provides compositions of these polynucleotides, including compositions comprising these polynucleotides and a pharmaceutical excipient, as well pharmaceutical compositions comprising these vectors. Pharmaceutical excipients are well known in the art and need not be described in detail herein. See, for example, *Remington: The Science and Practice of Pharmacy* (19$^{th}$ edition, 1995), Gennaro, ed. When these compositions are used for other purposes, such as detection (i.e., hybridization, amplification (i.e., PCR), and testing for function (i.e., transcription assay), these compositions may comprise suitable agents such as a buffer or a physiologically acceptable excipient.

Also included in the invention are kits comprising any one or more of the polynucleotides described herein in suitable packaging. These kits can be used, for example, for detection. The kits may optionally also contain additional components, such as buffers, capture reagents, developing reagents, labels, reacting surfaces, means for detection, control samples, instructions, and interpretive information.
Preparation of hUPII Transcriptional Regulatory Polynucleotides of the Invention The hUPII transcriptional regulatory polynucleotides of this invention can be obtained using chemical synthesis, recombinant methods, or PCR.

Methods of chemical polynucleotide synthesis are well known in the art and need not be described in detail herein. One of skill in the art can use the sequences provided herein and a commercial DNA synthesizer to produce a desired DNA sequence.

For preparing hUPII transcriptional regulatory polynucleotides using recombinant methods, a polynucleotide comprising a desired sequence can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Samnbrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as *PCR: The Polymerase Chain Reaction*, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example. RNA can also be obtained through in vitro reactions. An hUPII transcriptional regulatory polynucleotide can be inserted into a vector that contains appropriate transcription promoter sequences. Commercially available RNA polyrnerases will specifically initiate transcription at their promoter sites and continue the transcription process through the adjoining DNA polynucleotides. Placing hUPII transcriptional regulatory polynucleotides between two such promoters allows the generation of sense or antisense strands of hUPII transcriptional regulatory RNA sequence.

Cloning and Expression Vectors Comprising an hUPII Transcriptional Regulatory Polynucleotide The present invention further includes a variety of vectors (i.e., cloning and expression vectors) having cloned therein hUPII transcriptional regulatory polynucleotide(s). These vectors can be used for expression of recombinant polypeptides as well as a source of hUPII transcriptional regulatory polynucleotides. Cloning vectors can be used to obtain replicate copies of the hUPII transcriptional regulatory polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express polypeptides, encoded by an operably linked polynucleotide, in an individual, such as for eliciting an immune response via the polypeptide(s) encoded in the expression vector(s). Suitable cloning and expression vectors include any known in the art, e.g., those for use in bacterial, mammalian, yeast and insect expression systems. Specific vectors and suitable host cells are known in the art and need not be described in detail herein. For example, see Gacesa and Ramji, *Vectors*, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins substances, e.g., ampicillin, neomycyin, methotrexate, etc.; (b) complement auxotrophic deficiencies; or (c) supply critical nutrients not available from complex media. The choice of the proper marker gene will depend on the host cell, and appropriate genes for different hosts are known in the art. Cloning and expression vectors also typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen. The Examples provided herein also provide examples of cloning vectors.

Expression vectors generally are replicable polynucleotide constructs that contain a polynucleotide encoding a polypeptide of interest. The polynucleotide encoding the polypeptide of interest is operably linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from hUPII polynucleotides (e.g., the hUPII gene), or they may be heterologous (i.e., derived from other genes and/or other organisms). A polynucleotide sequence encoding a signal peptide can also be included to allow a polypeptide, encoded by an operably linked polynucleotide, to cross and/or lodge in cell membranes or be secreted from the cell. A number of expression vectors suitable for expression in eukaryotic cells including yeast, avian, and mammalian cells are known in the art. Examples of mammalian expression vectors contain both prokaryotic sequence to facilitate the propagation of the vector in bacteria, and one or more eukaryotic transcription units that are expressed in eukaryotic cells. Examples of mammalian expression vectors suitable for transfection of eukaryotic cells include the pcDNAI/amp, pcDNAI/neo, pRc/CMV, pSV2gpt, pSV2neo, pRSVneo, and pHyg derived vectors. Alternatively, derivatives of viruses such as the bovine papilloma virus (BPV-1), or Epstein-Barr virus (PHEB, pREP derived vectors) can be used for expression in mammalian cells. Examples of expression vectors for yeast systems, include YEP24, YIP5, YEP51, YEP52, YES2 and YRP17, which are cloning and expression vehicles useful for introduction of constructs into S. cerevisiae. Broach et al. (1983) Experimental Manipulation of Gene Expression, ed. M. Inouye, Academic Press. p. 83. Other common vectors, such as YEP13 and the Sikorski series pRS303–306, 313–316, 423–426 can also be used. Vectors pDBV52 and pDBV53 are suitable for expression in C. albicans. Baculovirus expression vectors for expression in insect cells include pVL-derived vectors (such as pVL1392, pVL1393 and pVL941), pAcUW-derived vectors and pBlueBac-derived vectors.

A vector comprising an hUPII transcriptional regulatory polynucleotide can be introduced into a host cell and/or a target cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus). The choice of means of introducing vectors or hUPII transcriptional regulatory polynucleotides will often depend on the host cell or target cell. A vector comprising an hUPII transcriptional regulatory polynucleotide can also be delivered to a host cell and/or a target cell in the form of a delivery vehicle, described below.

Delivery Vehicles Containing an hUPII Transcriptional Regulatory Polynucleotide

The present invention also provides delivery vehicles suitable for delivery of an hUPII transcriptional regulatory polynucleotide into cells (whether in vivo, ex vivo, or in vitro). Generally, an hUPII transcriptional regulatory sequence will be operably linked to a heterologous polynucleotide. An hUPII transcriptional regulatory polynucleotide can be contained within a cloning or expression vector, as described above, or within a viral vector. These vectors (especially expression vectors) can in turn be manipulated to assume any of a number of forms which may, for example, facilitate delivery to and/or entry into a target cell. Delivery of the polynucleotide constructs of the invention to eukaryotic cells, particularly to mammalian cells, more particularly to bladder cells, can be accomplished by any suitable art-known method. Delivery can be accomplished in vivo, ex vivo, or in vitro.

The invention provides methods and compositions for transferring such expression constructs into cells, especially in vivo for treatment of bladder tumors.

Delivery vehicles suitable for incorporation of an hUPII transcriptional regulatory sequence of the present invention for introduction into a host cell include non-viral vehicles and viral vectors. Verma and Somia (1997) Nature 389:239–242.

Non-viral Vehicles

A wide variety of non-viral vehicles for delivery of hUPII transcriptional regulatory polynucleotides of the present invention are known in the art and are encompassed in the present invention. An hUPII transcriptional regulatory polynucleotide can be delivered to a cell as naked DNA (U.S. Pat. No. 5,692,622; WO 97/40163). Alternatively, an hUPII transcriptional regulatory polynucleotide can be delivered to a cell associated in a variety of ways with a variety of substances (forms of delivery) including, but not limited to cationic lipids; biocompatible polymers, including natural polymers and synthetic polymers; lipoproteins; polypeptides; polysaccharides; lipopolysaccharides; artificial viral envelopes; metal particles; and bacteria. A delivery vehicle may take the form of a microparticle. Mixtures or conjugates of these various substances can also be used as delivery vehicles. An hUPII transcriptional regulatory polynucleotide can be associated with these various forms of delivery non-covalently or covalently.

One non-viral gene transfer vehicle suitable for use in the present invention is physical transfer of a polynucleotide in cationic lipids, which can take the form of liposomes. Reviewed in Mahato et al. (1997) Pharm. Res. 14:853–859. Liposomal preparations include, but are not limited to, cytofectins, multilamellar vesicles and unilamellar vesicles. Several commercial liposomal preparations are available for the delivery of DNA and RNA to cells, including but not limited to, Lipofectin™, Lipofectamine™, and DOTAP™.

Derivatized liposomes can be used as carriers of hUPII transcriptional regulatory polynucleotides. Immunoliposomes are derivatized liposomes which contain on their surface specific antibodies which bind to surface antigens on specific cell types, thus targeting these liposomes to particular cell types. Wang and Huang (1987) Proc. Natl. Acad. Sci. (U.S.A.) 84:7851; and Trubetskoy et al. (1992) Biochem. Biophys. Acta 1131:311. Other types of derivatization include modification of the liposomes to include ligands which bind to receptors on particular cell types, or receptors which bind specifically to cell surface molecules.

Lipopolyarnine can be used as a reagent to mediate transfection itself, without the necessity of any additional phospholipid to form liposomes. Behr et al. (1989) Proc. Natl. Acad. Sci. (U.S.A.) 86:6982.

Other lipid-based delivery vehicles are known and have been described, and can be used in the present invention. For example, U.S. Pat. No. 5,705,385 discloses lipid-nucleic acid particles for gene delivery via formation of hydrophobic lipid-nucleic acid complexes. The complexes are charge-neutralized. Formation of these complexes in either detergent-based or organic solvent-based systems, followed by removal of the detergent or organic solvent, leads to particle formation.

Polypeptide gene delivery vehicles include polyamino acids such as polylysine, and various naturally occurring polypeptides such as gelatin, and conjugates of these with other macromolecules.

Low molecular weight polylysine (PL) and other polycations can be used as carriers to promote DNA-mediated transfection into cultured mammalian cells. Zhou et al. (1991) *Biochem. Biophys. Acta* 1065:1068 reports synthesis of a polylysine-phospholipid conjugate, a lipopolylysine comprising PL linked to N-glutarylphosphatidylethanolamine, which reportedly increases the transfection efficiency of DNA.

Polylysine molecules conjugated to asialoorosomucoid ("ASOR") or transferrin can be used for target-specific delivery of associated polynucleotides to cells which express the appropriate receptor (i.e., asialoglycoprotein receptor or transferrin receptor, respectively). Such conjugates have been described. Wilson et al. (1992) *J. Biol. Chem.* 267:963; WO92/06180; WO92/05250; WO91/17761; Wagner et al. (1990) *Proc. Natl. Acad. Sci. U.S.A.* 87:3410; Zenke et al. (1990) *Proc. Natl. Acad. Sci. U.S.A.* 87:3655; and WO92/13570.

Polypeptide delivery vehicles include those which form microspheres, as described. WO 96/00295. Polypeptide microspheres can comprise polypeptide alone or mixtures of polypeptides with other macromolecules, for example chondroitin sulfate. The polypeptides may be crosslinked, as described. WO 96/40829. In addition, a targeting moiety can be incorporated into such polypeptide delivery vehicles.

Microparticles for delivery of polynucleotides into cells are known and can be used to deliver hUPII transcriptional regulatory polynucleotides to a cell. Microparticles generally comprise a polynucleotide and a substance which facilitates entry into a cell. These include, for example, polymeric cations, complexes of hydrophobized, positively charged biocompatible polymer and a lipoprotein (U.S. Pat. No. 5,679,559); complexes of a receptor ligand and a polycation (U.S. Pat. No. 5,635,383); polycation conjugated with poly-alkylene glycol or a polysaccharide (WO 96/21036); a complex between a fusion protein comprising a domain which specifically binds an hUPII transcriptional regulatory polynucleotide and a domain which targets a particular cell type (EP 753,069); chylomicrons (Hara et al. (1997) *Proc. Natl. Acad. Sci. USA* 94:14547–14552); metal particles such as tungsten and gold (Zelenin et al. (1997) *FEBS Letters* 414:319–322; and chitosan-based compounds (WO 97/42975).

Other types of carriers include covalently bound conjugates consisting of oligonucleotides in disulfide linkage to a targeting agent that promotes transport across cell membranes (WO 91/14696); artificial viral envelopes (Schreier et al. (1995) *J. Molec. Recognition* 8:59–62; and Chander and Schreier (1992) *Life Sci.* 50:481–489; and bacteria, for example Salmonella (Pawelek et al. (1997) *Cancer Res.* 57:4537–4544); and *Listeria monocytogenes* (Dietrich et al. (1998) *Nature Biotech.* 16:181–185.

The delivery vehicles of the present invention can include one or more targeting molecules incorporated into or attached to the vehicle. Targeting molecules include any molecule that binds specifically to a target cell type. This can be any type of molecule for which a specific binding partner exists. The term "specific binding partner" as used herein intends a member of a pair of molecules that interact by means of specific non-covalent interactions that depend on the three-dimensional structures of the molecules involved. Preferably, the specific binding partner is expressed only on the target cell type. Examples of targeting molecules which may be used are hormones, antibodies, cell adhesion molecules, saccharides, drugs, and neurotransmitters.

Compositions comprising an hUPII transcriptional regulatory polynucleotide in a delivery vehicle are encompassed by this invention. When these compositions are to be used pharmaceutically, they are combined with a pharmaceutically acceptable excipient. Accordingly, the invention also provides compositions of these vectors, including compositions comprising these vectors and a pharmaceutical excipient, as well pharmaceutical compositions comprising these vectors. Pharmaceutical excipients are well known in the art and need not be described in detail herein. See, for example, *Remington: The Science and Practice of Pharmacy* (19$^{th}$ edition, 1995), Gennaro, ed.

An hUPII transcriptional regulatory polynucleotide can be inserted into a non-viral vector for delivery into a cell, as described above. Included in the non-viral vector category are prokaryotic plasmids and eukaryotic plasmids, as described above. One skilled in the art will appreciate that a wide variety of such vectors are known, are readily available, and can be used in the present invention. An hUPII transcriptional regulatory polynucleotide inserted into a non-viral vector can be delivered to a cell with the help of any of the above-described vehicles, as well as direct injection of the polynucleotide, or other types of delivery methods. The above-described delivery vehicles can also be used to delivery an hUPII transcriptional regulatory polynucleotide inserted into a viral vector.

Preparation of Non-viral Vehicles Comprising an hUPII Transcriptional Regulatory Polynucleotide Preparation of liposomes for transfer of polynucleotides can be carried out as described by various investigators (Wang and Huang (1987) *Biochem. Biophys. Res. Commun.* 147:980; Wang and Huang (1989) *Biochemistry* 28:9508; Litzinger and Huang (1992) *Biochem. Biophys. Acta* 1113 201; Gao and Huang (1991) *Biochem. Biophys. Res. Commun.* 179:280; Felgner WO91/17424; WO91/16024).

The preparation of other types of non-viral vehicles is known in the art and has been described. For example, preparation of polylysine delivery vehicles has been described by Zhou et al. (1991) *Biochem. Biophys. Acta* 1065:1068. Methods for preparation of microparticles of various compositions have also been described (see publications cited above) and are known in the art.

Introduction of targeting molecules into the non-viral vehicles of the present invention can be carried out by any known means, including incorporation into a cationic lipid vehicle or a microsphere or a microparticle; by direct chemical conjugation with a macromolecule of which the delivery vehicle is comprised, or any other known methods.

Viral Vectors

An hUPII transcriptional regulatory polynucleotide can be inserted into a viral vector. Viral vectors include, but are not limited to, DNA viral vectors such as those based on adenoviruses, herpes simplex virus, poxviruses such as vaccinia virus, and parvoviruses, including adeno-associated virus; and RNA viral vectors, including, but not limited to, the retroviral vectors. Retroviral vectors include murine leukemia virus, and lentiviruses such as human immunodeficiency virus. Naldini et al. (1996) *Science* 272:263–267.

Replication-defective retroviral vectors harboring an hUPII polynucleotide sequence as part of the retroviral genome can be used. Such vectors have been described in detail. (Miller et al. (1990) *Mol. Cell Biol.* 10:4239; Kolberg, R. (1992) *J. NIH Res.* 4:43; Cometta et al. (1991) *Hum. Gene Ther* 2:215). The major advantages of retroviral vectors for gene therapy are: the high efficiency of gene transfer into replicating cells, the precise integration of the transferred genes into cellular DNA, and the lack of further spread of the sequences after gene transduction.

Representative examples of retroviral gene delivery vehicles that may be utilized within the context of the present invention include, for example, those described in EP 415,731; WO 90/07936; WO 94/03622; WO 93/25698; WO 93/25234; U.S. Pat. No. 5,219,740; WO 93/11230; WO 93/10218; Vile and Hart, *Cancer Res.* 53:83–88, 1993; Vile and Hart, *Cancer Res.* 53:962–967, 1993; Ram et al., *Cancer Res.* 53:83–88, 1993; Takamiya et al., *J. Neurosci. Res.* 33: 493–503, 1992; Baba et al., *J. Neurosurg* 79:729–735, 1993 (U.S. Pat. No. 4,777,127, GB 2,200,651, EP 0,345,242 and WO 91/02805).

Examples of suitable retroviruses include pLJ, pZIP, pWE and pEM which are well known to those skilled in the art. Examples of suitable packaging virus lines for preparing both ecotropic and amphotropic retroviral systems include psi Crip, psi cre, psi 2 and psi Am. Retroviruses have been used to delivery a variety of polynucleotides into many different cell types. See, for example, Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115.

Adenoviral vectors can also be used for delivery of hUPII transcriptional regulatory polynucleotides. Rosenfeld et al. (1992) *Cell* 68:143. Accordingly, the invention provides an adenovirus vector comprising any human uroplakin II transcriptional regulatory sequence described herein. The sequence may be operably linked to an adenovirus gene and/or a transgene. Certain adenoviral vector embodiments of the invention are further discussed in a separate section. It is understood that, with respect to the hUPII transcriptional regulatory polynucleotides described herein, any adenoviral vector containing any of these sequences is encompassed by the invention. Major advantages of adenovirus vectors are their potential to carry large insert polynucleotide sequences, very high viral titres, ability to infect non-replicating cells, and suitability for infecting tissues in situ.

For the purposes of this invention, the adenoviral vectors can be replication competent or replication defective, depending on the desired outcome of infection with virus.

In general, replication-defective adenovirus gene transfer systems are based upon recombinant, engineered adenovirus which is rendered replication-incompetent by deletion of a portion of its genome, such as E1 or E3, and yet still retains its competency for infection. Berkner et al. (1988) *BioTechniques* 6:616; Rosenfeld et al. (1991) *Science* 252:431–434; Rosenfeld et al. (1992) *Cell* 68:143–155. Relatively large foreign proteins can be expressed when additional deletions are made in the adenovirus genome. For example, adenoviruses deleted in both E1 and E3 regions are capable of carrying up to 10 kb of foreign DNA and can be grown to high titers in 293 cells. Suitable adenoviral vectors derived from the adenovirus strain Ad type 5 or other strains of adenovirus (e.g., Ad2, Ad3, Ad7, etc.) are well known to those skilled in the art.

Another viral vector system useful for delivery of an hUPII transcriptional regulatory polynucleotide is the adeno-associated virus (AAV). Adeno-associated virus is a naturally occurring defective virus that requires another virus, such as an adenovirus or a herpes virus, as a helper virus for efficient replication and a productive life cycle. Muzyczka et al. (1992) *Curr. Topics Microbiol. Immunol.* 158:97–129. AAV as a delivery vehicle for an hUPII transcriptional regulatory polynucleotide can be constructed and introduced into cells by any means known in the art, including the methods described in U.S. Pat. No. 5,658,785.

In addition to the viral vectors describe above, numerous other viral vectors systems may also be utilized as a gene delivery vehicle. Representative examples of such gene delivery vehicles include viruses such as pox viruses, such as canary virus or vaccinia virus (Fisher-Hoch et al., *PNAS* 86:317–321, 1989; Flexner et al., *Ann N.Y. Acad. Sci.* 569:86–103, 1989; Flexner et al., *Vaccine* 8:17–21, 1990; U.S. Pat. Nos. 4,603,112, 4,769,330, 5,017,487 and 5,656,465; WO 89/01973); SV40 (Mulligan et al., *Nature* 277:108–114, 1979; influenza virus (Luytjes et al., *Cell* 59:1107–1113, 1989; McMicheal et al., *N. Eng. J. Med.* 309:13–17, 1983; and Yap et al., *Nature* 273:238–239, 1978; herpes (Kit, *Adv. Exp. Med. Biol.* 215:219–236 1989; U.S. Pat. No. 5,288,641); HIV (Poznansky, *J. Virol.* 65:532–536, 1991); measles (EP 0 440,219); Semliki Forest Virus, and coronavirus, as well as other viral systems (e.g., EP 0,440, 219; WO 92/06693; U.S. Pat. No. 5,166,057). In addition, viral carriers may be homologous, non-pathogenic (defective), replication competent virus (e.g., Overbaugh et al., *Science* 239:906–910, 1988), and nevertheless induce cellular immune responses, including CTL.

Viral vectors comprising an hUPII transcriptional regulatory polynucleotide can be targeted to a particular cell type for more efficient delivery of an hUPII transcriptional regulatory polynucleotide, for example, to a neoplastic bladder urothelial cell. For example, a viral vector can comprise, in addition to an hUPII transcriptional regulatory polynucleotide, a polynucleotide encoding one member of a specific binding pair which inserts into the viral envelope or capsid and which targets the viral particle to a cell having the complementary member of the specific binding pair on its surface. WO 95/26412. Alternatively, the surface of a viral particle can be covalently modified to target it to a particular cell. WO 92/06180; WO 92/05266.

Viral vectors can be so constructed that they contain regulatable control elements which are controlled, for example, by tetracycline. WO 97/20463.

Virus-based vectors can also be used to deliver an hUPII transcriptional regulatory polynucleotide. These include retrotransposon vectors (U.S. Pat. No. 5,354,674) and synthetic vectors (WO 94/20608; WO 96/26745).

Viral Vectors Comprising an IRES

In one aspect of the present invention, the adenovinis vectors comprise co-transcribed first and second genes under control of a urothelial cell-specific TRE, such a hUPII TRE, wherein the second gene is under translational control of an internal ribosome entry site (IRES). IRES elements were first discovered in picomavirus mRNAs (Jackson R J, Howell M T, Kaminski A (1990) *Trends Biochem Sci* 15(12): 477–83) and Jackson R J and Kaminski, A. (1995) *RNA* 1(10);985–1000). The present invention provides improved adenovirus vectors comprising co-transcribed first and second genes under transcriptional control of a heterologous, target cell-specific TRE, and wherein the second gene (i.e., coding region) is under translational control of an internal ribosome entry site (IRES). Any IRES may be used in the adenovirus vectors of the invention, as long as they exhibit requisite function in the vectors. Example of IRES which can be used in the presentin vention include those provided in Table 6and referenced in Table 7. Examples of IRES elements include the encephelomycarditis virus (EMCV) which is commercially available from Novagen (Duke at al. (1992) *J. Virol* 66(3): 1602–9) the sequence for which is depicted in Table 6 (SEQ ID NO:42). Another example of an IRES element disclosed herein is the VEGF IPES (Huez et al. (1998) *Mol Cell Biol* 18(11):6178–90). This IRES has short segment and the sequence is depicted in Table 6 (SEQ ID NO:43).

Figure 7:
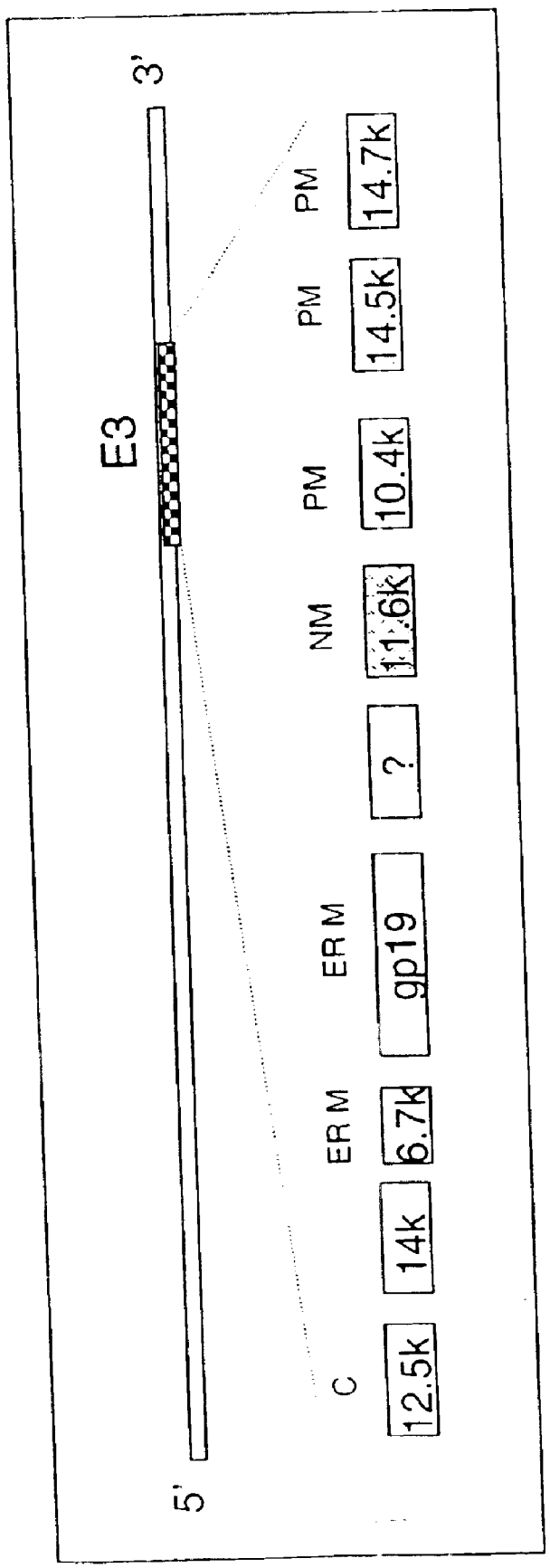
FIG. 7 shows a schematic representation of the E3 region of adenovirus.

The IRES promotes direct internal ribosome entry to the initiation codon of a downstream cistron, leading to cap-independent translation. Thus, the product of a downstream cistron can be expressed from a bicistronic (or multicistronic) mRNA, without requiring either cleavage of a polyprotein or generation of a monocistronic mRNA. Therefore, in one illustrative embodiment of the present invention, an adenovirus vector comprising E1B under translational control of an IRES allows translation of E1B from a bicistronic E1A–E1B mRNA under control of a target cell-specific TRE. FIG. 7 provides a schematic representation of adenovirus constructs of the present invention.

Internal ribosome entry sites are approximately 450 nucleotides in length and are characterized by moderate conservation of primary sequence and strong conservation of secondary structure. The most significant primary sequence feature of the IRES is a pyrimidine-rich site whose start is located approximately 25 nucleotides upstream of the 3' end of the IRES. See Jackson et al. ( 990).

Three major classes of picornavirus IRES have been identified and characterized: (1) the cardio- and aphthovirus class (for example, the encephelomycarditis virus, Jang et al. (1990) *Gene Dev* 4:1560–1572); (2) the entero-and rhinovirus class (for example, polioviruses, Borman et al. (1994) *EMBO J.* 13:314903157); and (3)the hepatitis A virus (HAV) class, Glass et al. (1993) *Virol* 193:842–852). For the first two classes, two general principles apply. First, most of the 450-nucleotide sequence of the IRES functions to maintain particular secondary and tertiary structures conducive to ribosome binding and translational initiation. Second, the ribosome entry site is an AUG triplet located at the 3' end of the IRES, approximately 25 nucleotides downstream of a conserved oligopyrimidine tract. Translation initiation can occur either at the ribosome entry site (cardioviruses) or at the next downstream AUG (entero/rhinovirus class). Initiation occurs at both sites in aphthoviruses.

HCV and pestiviruses such as bovine viral diarrhea virus (BVDV) or classical swine fever virus (CSFV) have 341 nt and 370 nt long 5'-UTR respectively. These 5'-UTR fragments form similar RNA secondary structures and can have moderately efficient IRES function (Tsukiyama-Kohara et al. (1992) *J. Virol.* 66:1476–1483; Frolov I et al., (1998) (RNA) 4:1418–1435). Table 6 depicts the 5'-UTR region from HCV genome sequence (GenBank accession D14853).

Leishmania RNA virus 1 (LRV1) is a double-stranded RNA virus. Its 128 nt long 5'-UTR has IRES activity to facilitate the cap-independent translation, Maga et al.,(1995) *Mol Cell Biol* 15:4884–4889). This fragment also forms conserved stemloop secondary structure and at least the front part is essential.

Recent studies showed that both Friend-murine leukemia virus (MLV) 5'-UTR and rat retrotransposon virus-like 30S (VL30) sequences contain IRES structure of retroviral origin (Torrent et al. (1996) *Hum Gene Ther* 7:603–612). These fragments are also functional as packing signal when used in retroviruse derived vectors. Studies of avian reticuloendotheliosis virus type A (REV-A) show that its IRES maps downstream of the packaging/dimerization (E/DLS) sequence and the minimal IRES sequence appears to be within a 129 nt fragment (452–580) of the 5' leader, immediately upstream of the gag AUG codon (Lopez-Lastra et al. (1997) *Hum Gene Ther* 8:1855–1865).

In eukaryotic cells, translation is normally initiated by the ribosome scanning from the capped mRNA 5' end, under the control of initiation factors. However, several cellular mnRNAs have been found to be with IRES structure to mediate the cap-independent translation (van der Velde, et al. (1999) *Int J Biochem Cell Biol.* 31:87–106). Examples are immunoglobulin heavy-chain binding protein (BiP) (Macejak et al. (1991) *Nature* 353:90–94), antennapedia mnRNA of Drosophilan (Oh et al. (1992) *Gene and Dev* 6:1643–1653), fibroblast growth factor-2 (FGF-2) (Vagner et al. (1995) *Mol Cell Biol* 15:35–44), platelet-derived growth factor B (PDGF-B) (Bernstein et al. (1997) *J Biol Chem* 272:9356–9362), insulin-like growth factor II (Teerink et al. (1995) *Biochim Biophys Acta* 1264:403–408), and the translation initiation factor eIF4G (Gan et al. (1996) *J Biol Chem* 271:623–626). Table 6 depicts the 5'-noncoding region for BiP and PDGF. Recently, vascular endothelial growth factor (VEGF) was also found to have IRES element (Stein et al. (1998) *Mol Cell Biol* 18:3112–3119; Huez et al. (1998) *Mol Cell Biol* 18:6178–6190).

Apart from the oligopyrimidine tract, nucleotide sequence per se does not appear to be important for IRES function. Without wishing to be bound by theory, a possible explanation for the function of an IRES is that it forms secondary and/or tertiary structures which orient particular single-stranded regions of its sequence in a three-dimensional configuration that is conducive to interaction with a mammalian ribosome (either ribosomal protein and/or ribosomal RNA components) and/or initiation factor(s) and/or RNA binding proteins which interact with ribosomes and/or initiation factors. It is also possible that the three-dimensional structure of the IRES is determined or stabilized by one or more RNA-binding proteins. Thus it is possible to devise synthetic IRES sequences having similar single-stranded regions in a similar three-dimensional configuration.

In certain cases, one or more trans-acting cellular proteins may be required for IRES function. For example, the HAV and entero/rhinovirus IRESes function inefficiently in vitro in reticulocyte lysates. Supplementation of a reticulocyte lysate with a cytoplasmic extract from HeLa, Krebs II ascites, or L-cells restores activity of entero/rhinovirus IRESes. See, for example, Brown et al. (1979) *Virology* 97:396–405; and Domer et al. (1984) *J. Virol.* 50:507–514. Activity of the HAV IRES in vitro is stimulated by liver cytoplasmic extracts. Glass et al. (1993) *Virology* 193:1047–1050. These observations indicate that cell-specific translational regulation can be achieved through the use of a cell-specific IRES. Furthermore, coordinated cell-specific transcriptional and translational regulatory elements can be included in a vector to further increase cell specificity of viral replication. For example, the combination of an AFP-TRE and a HAV-IRES can be used to direct preferential replication of a vector in hepatic cells. Thus, in one illustrative embodiment, a vector comprises an AFP-TRE regulating the transcription of a bicistronic E1A–E1B mRNA in which E1B translation is regulated by an ECMV IRES. In another illustrative embodiment, the vector comprises a probasin-TRE regulating the transcription of a bicistronic E1A–E1B mRNA in which E1B translation is regulated by an ECMV IRES. In yet another illustrative embodiment, a vector comprises a CMV-TRE regulating the transcription of a bicistronic E1A–E1B mRNA in which E1B translation is regulated by an ECMV IRES.

Examples of IRES which can be used in the present invention include those provided in Table 6 and Table 7. In order to test for an IRES sequence which may be used in the present invention, a test vector is produced having a reporter gene, such as luciferase, for example, placed under translational control of an IRES to be tested. A desired cell type is transfected with the vector containing the desired IRES-reporter gene and an assay is performed to detect the presence of the reporter gene. In one illustrative example, the test vector comprises a co-transcribed chloramphenicol transferase (CAT) and luciferase encoding gene transcriptionally driven by a CMV promoter wherein the luciferase encoding gene is translationally driven by an IRES to be tested. Host cells are transiently transfected with the test vector by means known to those of skill in the art and assayed for the presence of luciferase.

IRES may be prepared using standard recombinant and synthetic methods known in the art, and as described in the Examples. For cloning convenience, restriction sites may be engineered into the ends of the IRES fragments to be used.

Preparation of Viral Vectors Comprising an hUPII Transcriptional Regulatory Polynucleotide The basic technique of inserting genes into viruses are known to the skilled artisan and involve, for example, recombination between the viral polynucleotide sequences flanking a polynucleotide in a donor plasmid and homologous sequences present in the parental virus. Mackett et al. (1982) *Proc. Natl. Acad. Sci. USA* 79:7415–7419. For example, a unique restriction site that is naturally present or artificially inserted in the parental viral vector can be used to insert a polynucleotide flanked by the same restriction site as in the viral vector.

A DNA virus can be constructed as follows. First, the polynucleotide sequence to be inserted into the virus can be placed into a plasmid, e.g., an *E. coli* plasmid construct, into which a polynucleotide homologous to a section of the polynucleotide such as that of the virus has been inserted. Separately the polynucleotide sequence to be inserted is ligated to a promoter. The promoter-gene linkage is positioned in the plasmid construct so that the promoter-gene linkage is flanked on both ends by polynucleotide sequences homologous to a polynucleotide sequence flanking a region of viral DNA which is the desired insertion region. The resulting plasmid construct is then amplified by growth within *E. coli* bacteria and isolated. Preferably, the plasmid also contains an origin of replication such as the *E. coli* origin of replication, and a marker such as an antibiotic resistance gene for selection and propagation in *E. Coli.*

Second, the isolated plasmid containing the polynucleotide sequence to be inserted is transfected into a cell culture, e.g., chick embryo fibroblasts, along with the virus. Recombination between homologous DNA in the plasmid and the viral genome respectively results in a virus modified by the presence of the polynucleotide construct in its genome, at a site which does not affect virus viability.

As noted above, the gene is inserted into a region (insertion region), in the virus which does not affect virus viability of the resultant recombinant virus. The skilled artisan can readily identify such regions in a virus by, for example, randomly testing segments of virus DNA for regions that allow recombinant formation without seriously affecting virus viability of the recombinant. One region that can readily be used and is present in many viruses is the thymidine kinase gene.

Techniques for preparing replication-defective adenoviruses are well known in the art, as exemplified by Ghosh-Choudhury and Graham (1987) *Biochem. Biophys. Res. Comm.* 147:964–973; Ghosh-Choudhury et al. (1987) *EMBO J.* 6:1733–1739; McGrory et al. (1988) *Virol.* 163:614–617. It is also well known that various cell lines may be used to propagate recombinant adenoviruses, so long as they complement any replication defect which may be present. One example is the human 293 cell line, but any other cell line that is permissive for replication. For example, for viral constructs which, by virtue of insertion of an hUPII transcriptional regulatory polynucleotide, E1A and E1B are not expressed, a cell line which expresses E1A and E1B is employed. Further, the cells can be propagated either on plastic dishes or in suspension culture, in order to obtain virus stocks.

Preparation of replication-competent adenoviral vectors is discussed in a separate section.

Recombinant retroviruses which are constructed to carry or express an hUPII transcriptional regulatory polynucleotide can be readily constructed from a wide variety of retroviruses, including for example, B, C, and D type retroviruses as well as spumaviruses and lentiviruses (see RNA *Tumor Viruses*, Second Edition, Cold Spring Harbor Laboratory, 1985). Such retroviruses may be readily utilized in order to assemble or construct retroviral gene delivery vehicles given the disclosure provided herein, and standard recombinant techniques (e.g., Sambrook et al, *Molecular Cloning: A Laboratory Manual,* 2d ed., Cold Spring Harbor Laboratory Press, 1989; Kunkle, *PNAS* 82:488, 1985). In addition, portions of the retroviral gene delivery vehicles may be derived from different retroviruses. For example, retroviral LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

Insertion of an IRES into a vector is accomplished by methods and techniques that are known in the art and described herein supra, including but not limited to, restriction enzyme digestion, ligation, and PCR. A DNA copy of an IRES can be obtained by chemical synthesis, or by making a cDNA copy of, for example, a picornavirus IRES. See, for example, Duke et al. (1995) *J. Vvirol.* 66(3):1602–9) for a description of the EMCV IRES and Huez et al. (1998), *MoL Cell. Biol.* 18(11):6178–90) for a description of the VEGF IRES. The internal translation initiation sequence is inserted into a vector genome at a site such that it lies upstream of a 5'-distal coding region in a multicistronic MRNA. For example, in a preferred embodiment of an adenovirus vector in which production of a bicistronic E1A–E1B mRNA is under the control of a target cell-specific TRE, the E1B promoter is deleted or inactivated, and an IRES sequence is placed between E1A and E1B. In other embodiments disclosed herein, the 19-kDa region of E1B is deleted. IRES sequences of cardioviruses and certain aphthoviruses contain an AUG codon at the 3' end of the IRES that serves as both a ribosome entry site and as a translation initiation site. Accordingly, this type of IRES is introduced into a vector so as to replace the translation initiation codon of the protein whose translation it regulates. However, in an IRES of the entero/rhinovirus class, the AUG at the 3' end of the IRES is used for ribosome entry only, and translation is initiated at the next downstream AUG codon. Accordingly, if an entero/rhinovirus IRES is used in a vector for translational regulation of a downstream coding region, the AUG (or other translation initiation codon) of the downstream gene is retained in the vector construct.

A major prerequisite for the use of retroviruses is to ensure the safety of their use, particularly regarding the possibility of the spread of wild-type virus in the cell population. The development of specialized cell lines ("packaging cells") which produce only replication-defective retroviruses has increased the utility of retroviruses for gene delivery, and defective retroviruses are well characterized for gene delivery purposes. Miller et al. (1990)

Blood 76:271. Recombinant retroviruses can be constructed in which part of the retroviral coding sequence (gag, pol, env) has been replaced by an hUPII transcriptional regulatory polynucleotide, rendering the retrovirus replication defective. The replication-defective virus is then packaged into virions which can be used to infect a target cell through the use of a helper virus by standard techniques. Protocols for producing recombinant retroviruses and for infecting cells in vitro or in vivo can be found in Current Protocols in Molecular Biology, Ausubel, F. M. et al. (eds) Greene Publishing Associates (1989) and periodic updates, and other standard laboratory manuals.

Packaging cell lines suitable for use with the above-described vector constructs may be readily prepared (see WO 92/05266), and utilized to create producer cell lines (also termed vector cell lines or "VCLs") for the production of recombinant vector particles, given the disclosure provided herein.

Introduction into Host Cells and/or Target Cells of Non-viral Vehicles Comprising an hUPII Transcriptional Regulatory Polynucleotide Non-viral vehicles comprising an hUPII transcriptional regulatory polynucleotide may be introduced into host cells and/or target cells by any method known in the art, such as transfection by the calcium phosphate coprecipitation technique; electroporation; electropermeabilization; liposome-mediated transfection; ballistic transfection; biolistic processes including microparticle bombardment, jet injection, and needle and syringe injection; or by microinjection. Numerous methods of transfection are known to the skilled worker in the field. A number of these methods can be carried out both ex vivo and in vivo. Biolistic gene transfer, including jet injection, microparticle bombardment and needle and syringe injection, can be carried out by art-known methods. For a review, see Furth (1997) *Mol. Biotechnol.* 7:139–143. In vivo electropermeabilization can be performed as described. Rols et al. (1998) Nature Biotech. 16:168–1171. Successful transfection is generally recognized when any indication of the operation of this vector occurs in the host cell. Transformation is achieved using standard techniques appropriate to the particular host cells used. Naked DNA can be introduced by direct injection. Polynucleotides can also be introduced using various implantable devices such as those described in U.S. Pat. No. 5,501,662; and Koole et al. (1998) *Nature Biotech.* 16:172–176.

Introduction into Host Cells and/or Target Cells of Viral Vehicles Comprising an hUPII Transcriptional Regulatory Polynucleotide Viral delivery vehicles can be introduced into cells by infection. Alternatively, viral vehicles can be incorporated into any of the non-viral delivery vehicles described above for delivery into cells. For example, viral vectors can be mixed with cationic lipids (Hodgson and Solaiman (1996) *Nature Biotechnol.* 14:339–342); or lamellar liposomes (Wilson et al. (1977) *Proc. Natl. Acad. Sci. USA* 74:3471; Faller et al. (1984) *J. Virol.* 49:269).

For in vivo delivery, the delivery vehicle(s) can be introduced into a patient by any of a number of methods, each of which is familiar in the art. For instance, a pharmaceutical preparation of the gene delivery system can be introduced systematically, e.g. by intravenous injection, and specific transduction of the target cells occurs predominantly from specificity of transfection provided by the gene delivery vehicle, cell-type or tissue-type expression due to the transcriptional regulatory sequences controlling expression of the gene, or a combination thereof. In other embodiments initial delivery of the recombinant gene is more limited with introduction into the animal being quite localized. For example, the gene delivery vehicle can be introduced by catheter (see U.S. Pat. No. 5,328,470) or by sterotactic injection (e.g. Chen et al. (1994) *Proc. Natl. Acad. Sci. U.S.A.* 91:3054–3057). Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drugs, including proteinacious biopharmaceuticals, and can be adapted for release of viral particles through the manipulation of the polymer composition and form. A variety of biocompatible polymers (including hydrogels), including both biodegradable and non-degradable polymers, can be used to form an implant or the sustained release of an the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, Concise Encyclopedia of Medical & Dental Materials, ed. by David Williams (MIT Press: Cambridge, Mass., 1990); and the Sabel et al. U.S. Pat. No. 4,883,666. In another type of implant, a source of cells producing the recombinant virus is encapsulated in implantable hollow fibers. Such fibers can be pre-spun and subsequently loaded with the viral source (Aebischer et al. U.S. Pat. No. 4,892,538; Aebischer et al. U.S. Pat. No. 5,106,627; Hoffinan et al. (1990) Expt. Neurobiol. 110:39–44; Jaeger et al. (1990) Prog. Brain Res. 82:41–46; and Aebischer et al. (1991) J. Biomech. Eng 113: 178–183), or can be co-extruded with a polymer which acts to form a polymeric coat about the viral packaging cells (Lim U.S. Pat. No. 4,391,909; Sefton U.S. Pat. No. 4,353,888; Sugarmori et al. (1989) Trans. Am. Artif. Intern. Organs 35:791–799; Sefton et al. (1987) Biotechnol. Bioeng. 29:1135–1143; and Aebischer eta. (1991) Biomaterials 12:50–55. Again, manipulation of the polymer can be carried out to provide for optimal release of viral particles.

Host Cells and Target Cells Comprising an hUPII Transcriptional Regulatory Polynucleotide The invention further provides host cells and target cells transfected or transformed with (i.e., comprising) the above-described hUPII transcriptional regulatory sequences and/or hUPII-TRE(s), above-described expression or cloning vectors of this invention, or above-described delivery vehicles comprising hUPII transcriptional regulatory sequences and/or hUPII-TRE(s). These cells are cultured in conventional nutrient media modified as appropriate for inducing promoters, selecting transformants, or amplifying the genes encoding the desired sequences.

The cells which are suitable for use in the methods of the present invention with respect to expression, transcriptional control, or for purposes of cloning and propagating an hUPII transcriptional regulatory polynucleotide can be prokaryotic or eukaryotic.

Host systems are known in the art and need not be described in detail herein. Prokaryotic hosts include bacterial cells, for example *E. coli, B. subtilis*, and mycobacteria. Among eukaryotic hosts are yeast, insect, avian, plant, *C. elegans* (or nematode) and mammalian cells. Examples of fungi (including yeast) host cells are *S. cerevisiae, Kluyveromyces lactis* (*K. lactis*), species of *Candida* including *C. albicans* and *C. glabrata, Aspergillus nidulans, Schizosaccharomyces pombe* (*S. pombe*), *Pichia pastoris*, and *Yarowia lipolytica*. Examples of mammalian cells are COS cells, mouse L cells, LNCaP cells, Chinese hamster ovary (CHO) cells, human embroyonic kidney (HEK) cells, and African green monkey cells. *Xenopus laevis* oocytes, or other cells of amphibian origin, may also be used.

For the delivery vehicles described above, any eukaryotic cells, preferably mammalian cells can be used. Even more preferably, the cells are urothelial cells, such as bladder urothelial cells. The cells employed may be those derived from the bladder. Such cells include, but are not limited to, the cell lines SW780 (bladder cell carcinoma; available from the American Type Culture Collection under ATCC CRL-2169, UM-UC-3 (bladder cell carcinoma; available from the American Type Culture Collection under ATCC CRL-1749. Alternatively, the cells need not be derived from the bladder as long as the hUPII-TRE function is sufficiently preserved. This may be achieved, for example, by co-transfecting the cell with a gene encoding a product necessary for the function of the TRE of the urothelial cell-specific gene. For example, if an hUPII-TRE is inducible by a hormone, it may be necessary to co-transfect into the cells a construct which encodes and allows expression of a gene encoding the corresponding hormone receptor.

The host cells of this invention can be used, inter alia, as repositories of hUPII polynucleotides and/or vehicles for production of hUPII polynucleotides and/or polypeptides which are encoded by an operably linked polynucleotide.

Compositions containing cells into which have been introduced vectors comprising an hUPII-TRE operably linked to a heterologous polynucleotide are encompassed by this invention. When these compositions are to be used pharmaceutically, they are combined with a pharmaceutically acceptable excipient. Accordingly, the invention also provides compositions of these cells, including compositions comprising these cells and a pharmaceutical excipient, as well pharmaceutical compositions comprising these cells. Pharmaceutical excipients are well known in the art and need not be described in detail herein. See, for example, *Remington: The Science and Practice of Pharmacy* ($19^{th}$ edition, 1995), Gennaro, ed.

An example of a composition provided by the invention is a composition for expressing an anti-proliferation construct in a urothelial cell. The composition comprises. in addition to a pharmaceutically acceptable excipient, an hUPII-TRE a polynucleotide of claim 1 operably linked to a coding sequence for an anti-proliferation molecule, such as a toxin, an antigen, a lymphokine, a viral sequence, and/or an antisense sequence.

Methods Using the hUPII Transcriptional Regulatory Polynucleotides of the Invention The above-described hUPII transcriptional regulatory sequences can be used for a wide variety of purposes, which will vary with the desired or intended result. Accordingly, the present invention includes methods using the hUPII transcriptional regulatory sequences described above.

As described above, an hUPII transcriptional regulatory sequence can be operably linked to a heterologous polynucleotide. Such an hUPII-TRE is useful for selectively increasing transcription and/or translation of an operably linked heterologous polynucleotide in cells which allow an hUPII transcriptional regulatory sequence to function. Accordingly, the invention includes methods for increasing transcription of a polynucleotide sequence in a cell, generally involving introducing a construct comprising an hUPII transcriptional regulatory sequence operably linked to the polynucleotide into a cell in which the hUPII transcriptional regulatory sequence is functional, such as a urothelial cell. The polynucleotide sequence which is operably linked to the hUPII transcriptional regulatory sequence may be any sequence, including, but not limited to, a heterologous coding sequence such as a reporter gene, a toxin, a lymphokine.

In one embodiment, methods are provided for introducing a construct comprising an hUPII-TRE operably linked to a reporter gene into cells which allow an hUPII transcriptional regulatory sequence to function, i.e., a cell in which an hUPII transcriptional regulatory sequence, when operably linked to a promoter and a reporter gene, increases expression of the reporter gene. Examples include cells as shown in Example 2. Such cells are useful for screening compounds for therapeutic effect against bladder cancer. Methods for screening candidate compounds are described below.

In another embodiment, methods are provided for conferring selective cytotoxicity in cells in which an hUPII-TRE is functional, comprising contacting the cells with a delivery vehicle described herein, wherein the vehicle enters the cell such that transcription of the polynucleotide is operably linked to an hUPII-TRE which contributes to cytotoxicity. Preferably, the vehicle is a viral vector. Preferably, the viral vector is adenovirus. Cytotoxicity can be measured using standard assays in the art, such as dye exclusion, $^3$H-thymidine incorporation, and/or lysis.

In another embodiment, methods are provided for the selective transcription and/or expression of a heterologous polynucleotide in cells which the function of an hUPII transcriptional regulatory sequence is sufficiently preserved. By "sufficiently preserved", it is intended that transcription due to the presence of the transcriptional regulatory sequence is increased above basal levels (i.e., promoter alone; lacking enhancer) in the target cell by at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to about 500-fold, even more preferably at least about 1000-fold.

In particular, methods are provided for selective transcription and/or expression of a heterologous polynucleotide in cells which do not normally express the heterologous polynucleotide, or express the heterologous polynucleotide at undetectable levels. Expression of the heterologous polynucleotide by such cells can be detected in a variety of ways, including but not limited to, fluorescence-activated cell sorting (FACS) using one or more antibodies specific for a protein expressed on a cell surface (in situations in which the heterologous polynucleotide expresses a product which is expressed on the cell surface), enzyme-linked immunoassay (ELISA) of cell supernatants (for a secreted product of a heterologous polynucleotide), using an antibody specific for the secreted product.

Accordingly, the invention provides methods for increasing transcription of an operably linked polynucleotide sequence in a cell comprising introducing a construct comprising an hUPII transcriptional regulatory sequence operably linked to said polynucleotide into a cell in which the hUPII transcriptional regulatory sequence is functional. Such cells have been described above, as have hUPII transcriptional regulatory sequences (i.e., polynucleotide sequences having transcriptional regulatory activity).

The invention also provides (a) methods of detecting hUPII transcriptional regulatory sequences and (b) methods of amplifying hUPII transcriptional regulatory sequences. Detection methods generally entail contacting a suitable probe (described herein) with a polynucleotide in a sample under conditions that permit formation of a duplex and detecting the duplex, if any. An amplification (which may or may not be used for detection), such as PCR, generally involves using a suitable primer under conditions such that a target sequence is amplified. Such manipulations are well known in the art.

The invention also provides methods for expressing a polynucleotide coding sequence in a urothelial cell, said method comprising (a) introducing a vector comprising said coding sequence operably linked to a polynucleotide according to claim 1 into the urothelial cells; and expressing the coding sequence.

Screening Methods Utilizing an hUPII-TRE

The present invention provides methods for screening compounds which affect transcriptional regulatory function of an hUPII-TRE. Such compounds may be useful for treatment of bladder cancer. These screening methods employ an expression construct which comprises an hUPII transcriptional regulatory element (hUPII-TRE) (comprising any of the hUPII transcriptional regulatory sequences described herein) and a reporter gene under the transcriptional control of an hUPII-TRE whose expression product provides a detectable signal. The method comprises the steps of:

a) combining cells with a candidate compound in the presence of an appropriate inducing agent for a sufficient time for detectable expression of the reporter gene; and b) detecting the level of expression of the reporter gene as compared to the level of expression in the absence of the candidate compound.

Accordingly, the invention provides methods for screening for compounds which alter expression of a urothelial cell-specific gene, said method employing cells containing an expression construct, said expression construct comprising an hUPII TRE and a marker gene whose expression produce provides a detectable signal, wherein said marker gene is under the transcriptional control of the hUPII TRE, and the cell allows function of the hUPII TRE, them method comprising (a) combining the cells with a candidate compound and incubating the cells for a sufficient time for detectable expression of the marker gene and (b) detecting the level of expression of the marker gene as compared to the level of expression in the absence of the compound. An alteration of expression in the presence of the compound indicates that the compound alters urothelial cell-specific expression.

The screening methods involve introducing an expression construct comprising an hUPII-TRE operably linked to a reporter gene into cells which allow an hUPII-TRE to function. An hUPII-TRE can be operably linked to a reporter gene and inserted into a variety of vectors. Host cells are then transfected or transformed with vectors containing an hUPII-TRE linked to a reporter gene and cultured in conventional nutrient media modified as appropriate for selecting transformants, for example.

Cell-based screening assays of the present invention can be designed, e.g., by constructing cell lines in which the expression of a reporter protein, i.e., an easily assayable protein, such as β-galactosidase, chloramphenicol acetyl-transferase (CAT), green fluorescent protein (GFP) or luciferase, is dependent on the function of an hUPII-TRE. For example, a DNA construct comprising an hUPII-TRE may be operably linked to a gene encoding luciferase using methods well known in the act. The resulting DNA construct comprising the luciferase-encoding DNA is stably or transiently transfected into a host cell. The cell is exposed to a test compound and an appropriate inducing agent if necessary, such as a hormone, and, after a time sufficient to effect luciferase expression, the cells are assayed for the production of luciferase by standard enzyme assays.

Reporter genes which may be employed are known to those skilled in the art and include, but are not limited to, luciferase; aequorian (i.e., green fluorescent protein from *Aequorea Victoria*); β-galactosidase, chloramphenicol acetyl transferase; immunologically detectable protein "tags" such as human growth hormone; and the like. See, for example, Current Protocols in Molecular Biology (F. M. Ausubel et al., eds., 1987) and periodic updates. Any assay which detects a product of the reporter gene, either by directly detecting the protein encoded by the reporter gene or by detecting an enzymatic product of a reporter gene-encoded enzyme, is suitable for use in the present invention. Assays include colorimetric, fluorimetric, or luminescent assays or even, in the case of protein tags, radioimmunoassays or other immunological assays.

A recombinant polynucleotide comprising an hUPII-TRE or active fragment thereof, as well as those which may comprise other hUPII transcriptional regulatory elements described herein, may be prepared by any technique to those of skill in the art using the sequence information provided herein.

A construct may be incorporated into a suitable vector for the purposes of propagation or expression. Such vectors include prokaryotic plasmids, eukaryotic plasmids and viral vectors, and the choice of vector depends upon the design of the screening assay, the cell types involved and other factors. Expression constructs comprising an hUPII-TRE include plasmid and viral vectors, particularly adenovirus vectors, as described herein.

For preparing an expression construct comprising an hUPII-TRE operably linked to a reporter gene for use in the screening methods of the present invention, a polynucleotide comprising an hUPII-TRE operably linked to a reporter gene can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

The cells which are suitable for use in the methods of the present invention with respect to screening of compounds for possible therapeutic use in treatment of bladder cancer are any eukaryotic cells, preferably mammalian cells, which allow an hUPII-TRE to function. Preferably, the cells are urothelial cells, such as those described in the Examples.

An inducing agent can be any compound which is added to the growth environment of the cell and which, upon contact with and/or entry into the cell, results in the transcriptional activation of an hUPII-TRE. For the purposes of the present invention, an "appropriate inducing agent" is one which specifically induces the expression of an hUPII-TRE which is operably linked to a reporter gene. An example of an inducing agent used is a hormone.

Once an hUPII-TRE-reporter gene construct has been introduced into the host cell and stable cell lines are made, the cells may be cultured in a suitable growth medium, then exposed to an agent whose ability to modulate the activity of the hUPII-TRE is to be tested.

Stable cell lines comprising an expression construct which comprises an hUPII-TRE driving expression of a reporter gene can be generated for use in the screening methods, as described above. Alternatively, appropriate cells can be transiently transfected with the expression constructs, the cells cultured in a suitable growth medium, then exposed to an agent whose ability to modulate the activity of the hUPII-TRE is to be tested. Methods for transient transfection are known in the art.

The reporter gene used can encode luciferase activity, and an assay system can be chosen such that the product of the luciferase activity is luminescent. Luminescence may be determined in accordance with conventional commercial kits, e.g. enhanced luciferase assay kit (Analytical Luminescence Laboratory, Michigan). The cells may be distributed in multiwell plates which can be accommodated by a luminometer. A known number of cells is introduced into each one of the wells in an appropriate medium, the candidate compound added, and the culture maintained for at least 12 hours, more usually at least about 24, and not more than about 60 hours, particularly about 48 hours. The culture is then lysed in an appropriate buffer, using a non-ionic detergent, e.g. 1% triton X-100. The cells are then promptly assayed.

After a suitable time, cells are tested for amount of reporter gene product. A "suitable time" in this assay means an amount of time sufficient for the agent to be tested to effect a change in the levels of reporter gene product such that a difference from the control can be measured. This amount of time may depend on the stability of the reporter gene messenger RNA or protein, on how readily the agent enters the cell, on how stable the agent is once it enters the cell, and/or on other factors. In general, a suitable time must be determined empirically and this is well within the skill of one of ordinary skill in the art. A decrease or increase in the level of reporter gene product of from at least about 25% to about 40%, more preferably from at least about 40% to about 70%, and most preferably from about 70% to about 100% is indicative of an agent that modulates the activity of an hUPII-TRE.

Assay methods generally require comparison to a control sample to which no agent is added. Modulation of hUPII expression is said to be effected by a test agent if such an effect does not occur in the absence of the test agent.

In another embodiment, the above-described hUPII-TRE-reporter gene plasmid constructs may also be introduced into the host cells for transient expression of the reporter gene. In this assay system, the compound to be tested may be added before or simultaneously with introduction of the plasmid into the cells. To correct for differences in transfection efficiency, the cells can be co-transfected with a reference plasmid encoding, for example, β-galactosidase. The cells are then cultured for a time, after which the level of reporter gene product is measured and, if appropriate, the product encoded by the plasmid serving as a transfection efficiency control is also measured. The ability of the agent to modulate the activity of an hUPII-TRE is measured as a difference in the amount of reporter gene product relative to control cell culture to which no test compound was added.

In a further embodiment of the present invention, an hUPII-TRE operably linked to a reporter gene may be incorporated into a viral vector for packaging into a viral particle. The virus may be any known in the art which can infect eukaryotic cells. Preferably, adenovirus is used. An hUPII-TRE-reporter gene may be incorporated into an adenoviral vector at a variety of sites. Preferably one or more genes essential for adenovirus replication are replaced with an hUPII-TRE-reporter gene construct. For example, the regions known as E1A and E1B can be replaced with a fragment of DNA containing an hUPII-TRE operably linked to a reporter gene. The resulting adenovirus construct can be propagated by passage through a cell line that provides the E1A and E1B gene products, e.g. 293 cells, by methods known in the art. In this assay system, the adenovirus construct containing an hUPII-TRE operably linked to a reporter gene can be used to infect an appropriate cell line such as those described above. An agent whose ability to modulate the activity of an hUPII-TRE can be added either simultaneously with the adenoviral construct or after a suitable time. A "suitable time" in this assay system means an amount of time sufficient to allow entry of the viral particle into the cell, subsequent uncoating of the viral particle, and transport into the nucleus. This amount of time may be from about one to about five hours. After culturing the cells in an appropriate growth medium, the levels of reporter gene product are measured and compared to levels in recombinant host cell cultures to which no agent has been added.

Compounds can be tested singly or in combination with one another. Thus, screening assays provide a method for identifying an "agent," which can be used to modulate hUPII expression in a cell in vitro or in a patient. An "effective agent" is one that modulates hUPII expression.

As used herein, the term "modulate" means that the effective agent can increase or decrease the level of expression of a gene under transcriptional control of an hUPII-TRE or an active fragment thereof. Modulation can occur as a result of an effect at any point in signal transduction from the membrane of the cell to the nucleus. The ways that an effective agent can act to modulate the expression of hUPII include, but are not limited to 1) modifying binding of a transcription factor to an hUPII-TRE; 2) modifying the interaction between two transcription factors necessary for hUPII expression; 3) altering the ability of a transcription factor necessary for hUPII expression to enter the nucleus; 4) inhibiting the activation of a transcription factor involved in hUPII gene transcription; 5) modifying a cell-surface receptor which normally interacts with a ligand and whose binding of the ligand results in hUPII expression; 6) inhibiting the inactivation of a component of the signal transduction cascade that leads to hUPII expression; and 7) enhancing the activation of a transcription factor involved in hUPII gene transcription.

Adenoviral Vectors Comprising a Urothelial Cell-specific TRE

The present invention also provides replication-competent adenoviral vector constructs which comprise a gene, preferably an adenovirus gene, under transcriptional control of a urothelial cell-specific TRE. Preferably, the adenovirus gene contributes to cytotoxicity (whether direct and/or indirect), more preferably is one that contributes to or causes cell death, even more preferably is essential for adenoviral replication. Examples of a gene that contributes to cytotoxicity include, but are not limited to, adenovirus death protein (ADP). When the adenovirus vector(s) is selectively (i.e., preferentially) replication competent for propagation in target cells, i.e., urothelial cells, these cells will be preferentially killed upon adenoviral proliferation. Once the target cells are destroyed due to selective cytotoxic and/or cytolytic replication, the adenovirus vector replication is significantly reduced, thus lessening the probability of runaway infection and undesirable bystander effects. In vitro cultures may be retained to monitor the mixture (such as, for example, a biopsy or other appropriate biological sample) for occurrence (i.e., presence) and/or recurrence of the target cell, e.g., a neoplastic cell or other undesired cell. To further ensure cytotoxicity, one or more transgenes having a cytotoxic effect may also be present and under selective transcriptional control. In this embodiment, one may provide higher confidence that the target cells will be destroyed. Additionally, or alternatively, an adenovirus gene that contributes to cytotoxicity and/or cell death (such as ADP) may be included in the adenoviral vector, either free of, or under, selective transcriptional control.

Significantly, we have observed that such constructs are capable of selectively replicating in urothelial cells as opposed to smooth muscle cells, which adjoin urothelial cells in the bladder.

Urothelial Cell-specific TREs

Any urothelial cell-specific TRE may be used in the adenoviral vectors of the invention. Preferred urothelial cell-specific TREs include TREs derived from the uroplakins UPIa, UPIb, UPII, and UPIII, as well as urohingin. A uroplakin TRE may be from any species, depending on the intended use of the adenovirus, as well as the requisite fuinctionality is exhibited in the target or host cell.

For example, urothelial-specific TREs derived from the hUPII gene were described above. Accordingly, in some embodiments, an adenovirus vector of the invention comprises an adenovirus gene, preferably an adenoviral gene essential for replication, under transcriptional control of a urothelial cell-specific TRE which comprises the 2.2 kb sequence from the 5' flanking region of hUPII gene, as shown in FIG. 1. In other embodiments, an adenovirus vector of the invention comprises an adenovirus gene, preferably an adenoviral gene essential for replication, under transcriptional control of a urothelial cell-specific TRE which comprises a 1.8 kb sequence from the 5' flanking region of hUPII gene, as shown in nucleotides 430 to 2239 of FIG. 1. In other embodiments, the urothelial cell-specific TRE comprises a functional portion of the 2.2 kb sequence depicted in FIG. 1, such as a fragment of about 2000 bp or less, about 1500 bp or less, about 1000 bp or less, about 600 bp less, or at least 200 bp which includes the 200 bp fragment of the hUPII 5'-flanking region as described above. Other embodiments of hUPII transcriptional regulatory sequences suitable for the adenovirus vectors are described above and are included in the invention.

A 3.6 kb 5'-flanking sequence located from the mouse UPII (mUPII) gene which confers urothelial cell-specific transcription on heterologous genes is one urothelial cell-specific TRE useful in vectors of the instant invention (FIG. 2, SEQ ID NO:2). Smaller TREs (i.e., 3500 bp or less, more preferably less than about 2000 bp, 1500 bp, or 1000 bp) are preferred. Smaller TREs derived from the mUPII 3.6 kb fragment are one group of preferred urothelial cell-specific TREs. In particular, Inventors have identified an approximately 600 bp fragment from the 5' flanking DNA of the mUPII gene, which contains 540 bp of 5' untranslated region (UTR) of the mUPII gene, that confers urothelial cell-specific expression on heterologous genes.

Accordingly, in some embodiments, an adenovirus vector of the invention comprises an adenovirus gene, preferably an adenoviral gene essential for replication, under transcriptional control of a urothelial cell-specific TRE which comprises the 3.6 kb sequence from the 5' flanking region of mouse UPII gene, as shown in FIG. 2. In other embodiments, the urothelial cell-specific TRE comprises a functional portion of the 3.6 kb sequence depicted in FIG. 2, such as a fragment of about 3500 bp or less, about 2000 bp or less, about 1500 bp or less, or about 1000 bp or less which includes the 540 bp fragment of 5' UTR. The urothelial cell-specific TRE may also be a sequence which is substantially identical to the 3.6 kb mUPII 5'-flanking region or any of the described fragments thereof.

A urothelial cell-specific TRE can also comprise multimers. For example, a urothelial cell-specific TRE can comprise a tandem series of at least two, at least three, at least four, or at least five urothelial cell-specific TREs. These multimers may also contain heterologous promoter and/or enhancer sequences.

Optionally, a transcriptional terminator or transcriptional "silencer" can be placed upstream of the urothelial cell-specific TRE, thus preventing unwanted read-through transcription of the coding segment under transcriptional control of the urothelial cell-specific TRE. Also, optionally, the endogenous promoter of the coding segment to be placed under transcriptional control of the urothelial cell-specific TRE can be deleted.

A urothelial cell-specific TRE may or may not lack a silencer. The presence of a silencer (i.e., a negative regulatory element) may assist in shutting off transcription (and thus replication) in non-permissive cells (i.e., a non-urothelial cell). Thus, presence of a silencer may confer enhanced urothelial cell-specific replication by more effectively preventing adenoviral vector replication in non-target cells. Alternatively, lack of a silencer may assist in effecting replication in target cells, thus conferring enhanced urothelial cell-specific replication due to more effective replication in target cells.

It is also understood that other, heterologous, TREs may be included in the adenoviral vectors of this invention, and that these additional TREs may or may not be operably linked to the same gene(s) as the urothelial cell-specific TRE. For example a TRE (such as a cell type-specific or cell status-specific TRE) may be juxtaposed to a urothelial cell-specific TRE. "Juxtaposed" means a urothelial cell-specific TRE and a second TRE transcriptionally control the same gene. For these embodiments, the urothelial cell-specific TRE and the second TRE may be in any of a number of configurations, including, but not limited to, (a) next to each other (i.e., abutting); (b) both 5' to the gene that is transcriptionally controlled (i.e., may have intervening sequences between them); (c) one TRE 5' and the other TRE 3' to the gene.

As is readily appreciated by one skilled in the art, a urothelial cell-specific TRE is a polynucleotide sequence, and, as such, can exhibit function over a variety of sequence permutations. Methods of nucleotide substitution, addition, and deletion are known in the art, and readily available functional assays (such as the CAT or luciferase reporter gene assay) allow one of ordinary skill to determine whether a sequence variant exhibits requisite urothelial cell-specific transcription function. Hence, the invention also includes functionally-preserved variants of the nucleic acid sequences disclosed herein, which include nucleic acid substitutions, additions, and/or deletions. The variants of the sequences disclosed herein may be 80%, 85%, 90%, 95%, 98%, 99% or more identical, as measured by, for example, ALIGN Plus (Scientific and Educational Software, Pennsylvania), preferably using default parameters, which are as follows: mismatch=2; open gap=0; extend gap=2 to any of the urothelial cell-specific TRE sequences disclosed herein. Variants of urothelial cell-specific TRE sequences may also hybridize at high stringency to any of the urothelial cell-specific TRE sequences disclosed herein. While not wishing to be bound by a single theory, the inventors note that it is possible that certain modifications will result in modulated resultant expression levels, including enhanced expression levels. Achievement of modulated resultant expression levels, preferably enhanced expression levels, may be especially desirable in the case of certain, more aggressive forms of cancer, or when a more rapid and/or aggressive pattern of cell killing is warranted (due to an immunocompromised condition of the individual, for example).

As an example of how urothelial cell-specific TRE activity can be determined, a polynucleotide sequence or set of such sequences can be generated using methods known in the art, such as chemical synthesis, site-directed mutagenesis, PCR, and/or recombinant methods. The sequence(s) to be tested is inserted into a vector containing an appropriate reporter gene, including, but not limited to, chloramphenicol acetyl transferase (CAT), β-galactosidase (encoded by the lacZ gene), luciferase (encoded by the luc gene), a green fluorescent protein, alkaline phosphatase, and horse radish peroxidase. Such vectors and assays are readily available, from, inter alia, commercial sources. Plasmids thus constructed are transfected into a suitable host cell to test for expression of the reporter gene as controlled by the putative urothelial cell-specific TRE using transfection methods known in the art, such as calcium phosphate precipitation, electroporation, liposomes (lipofection) and DEAE dextran. Suitable host cells include any urothelial cell type, including but not limited to, KU-1, MYP3 (a non-tumorigenic rat urothelial cell line), 804G (rat bladder carcinoma cell line), cultured human urothelial cells (HUC), HCV-29, UM-UC-3, SW780, RT4, HL60, KG-1, and KG-1A. Non-urothelial cells, such as LNCaP, HBL-100, HLF, HLE, 3T3, Hep3B, HuH7, CADO-LC9, and HeLa are used as a control. Results are obtained by measuring the level of expression of the reporter gene using standard assays. Comparison of expression between urothelial cells and control indicates presence or absence of transcriptional activation.

Comparisons between or among various urothelial cell-specific TREs can be assessed by measuring and comparing levels of expression within a single urothelial cell line. It is understood that absolute transcriptional activity of a urothelial cell-specific TRE will depend on several factors, such as the nature of the target cell, delivery mode and form of the urothelial cell-specific TRE, and the coding sequence that is to be selectively transcriptionally activated. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the CMV immediate early promoter. This analysis can also indicate negative regulatory regions, i.e., silencers.

Alternatively a putative urothelial cell-specific TRE can be assessed for its ability to confer adenoviral replication preference for cells that allow a urothelial cell-specific TRE to function. For this assay, constructs containing an adenovirus gene essential to replication operatively linked to a putative urothelial cell-specific TRE are transfected into urothelial cells. Viral replication in those cells is compared, for example, to viral replication by wild type adenovirus in those cells and/or viral replication by the construct in non-urothelial cells. A more detailed description of this kind of assay is in Example 3.

It is understood that, to make and use the instant adenoviral vectors, it is not necessary to use urothelial cell-specific TREs having maximum activity, or having minimum size. The requisite degree of activity is determined, inter alia, by the anticipated use and desired result. For example, if an adenoviral vector of the invention is used to monitor cells for urothelial cell-specific TRE activity, it is possible that less than a maximal degree of responsiveness by a urothelial cell-specific TRE will suffice to qualitatively indicate the presence of such cells. Similarly, if used for treatment or palliation of a disease state, less-than-maximal responsiveness may be sufficient for the desired result, if, for example, the urothelial cells, such as transitional cell carcinoma cells, are not especially virulent and/or the extent of disease is relatively confined.

Various replication-competent adenovirus vectors can be made according to the present invention in which a single or multiple adenovirus gene(s) are under control of a urothelial cell-specific TRE.

For example, a urothelial cell-specific TRE can be introduced into an adenovirus vector immediately upstream of and operably linked to a gene which is a replication gene, e.g. an early gene such as E1A or E1B or a late gene such as L1, L2, L3, L4, or L5. Optionally, the endogenous adenovirus promoter for the replication gene is deleted, placing the gene under sole transcriptional control of a urothelial cell-specific TRE. Alternatively, a urothelial cell-specific TRE can be placed immediately upstream of and operably linked to an ADP (adenovirus death protein) gene.

In some embodiments, a urothelial cell-specific TRE is used with an adenovirus gene that is essential for propagation, so that replication competence is preferentially achievable in a target cell that allow a urothelial cell-specific TRE to function. Preferably, the gene is an early gene, such as E1A, E1B, E2, or E4. (E3 is not essential for viral replication.) More preferably, the early gene under urothelial cell-specific TRE control is E1A and/or E1B. More than one early gene can be placed under control of a urothelial cell-specific TRE. Example 3 provides a more detailed description of adenoviral constructs in which E1A is under transcriptional control of urothelial cell-specific TREs.

Figure 3B:
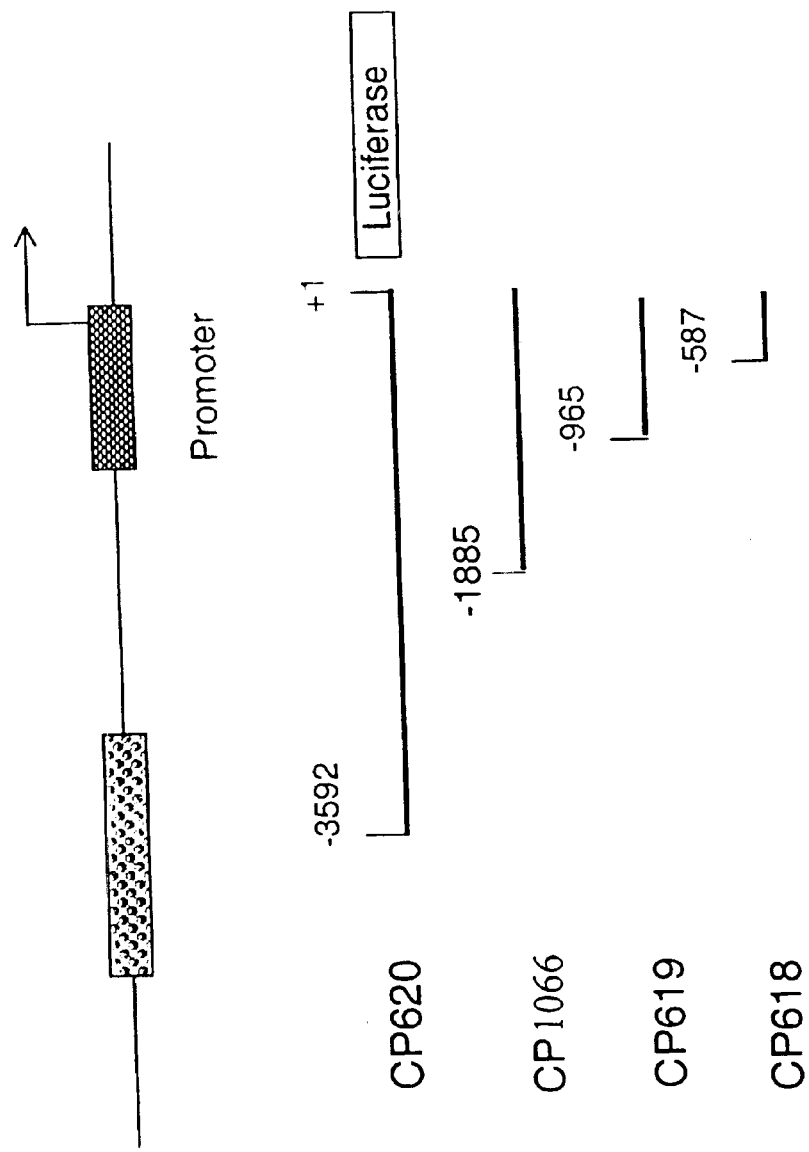
Figure 4A:
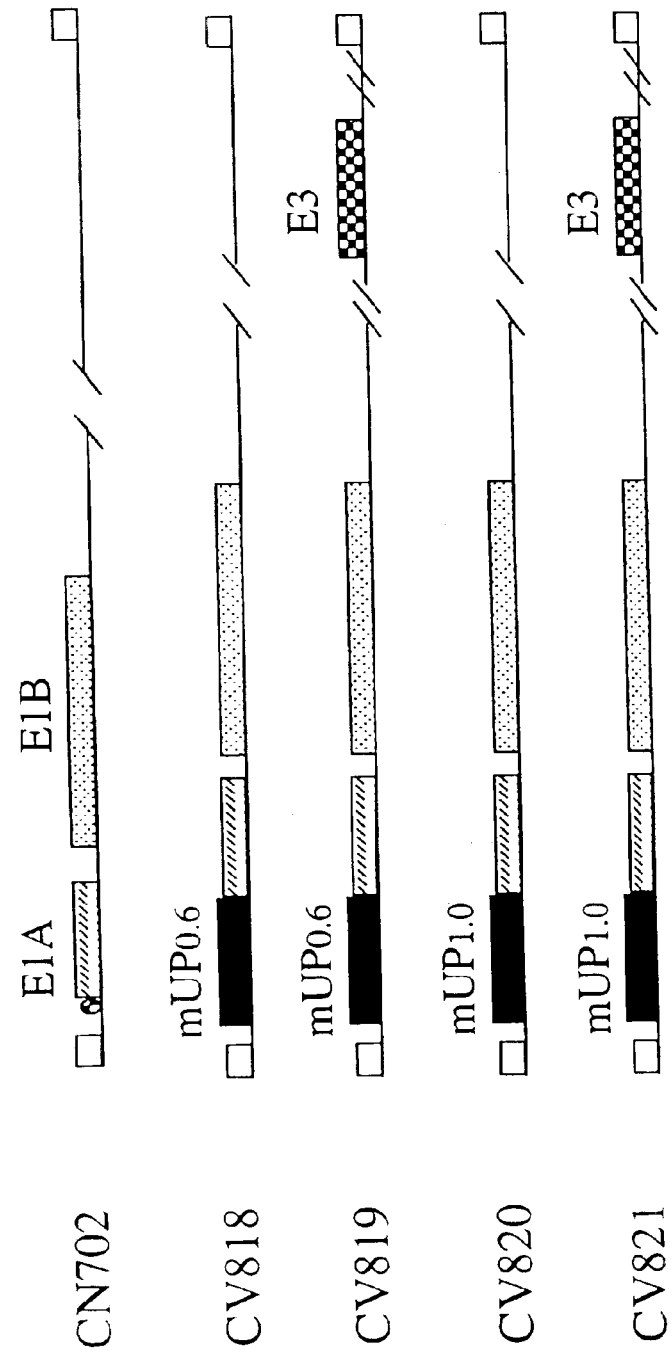
Figure 4B:
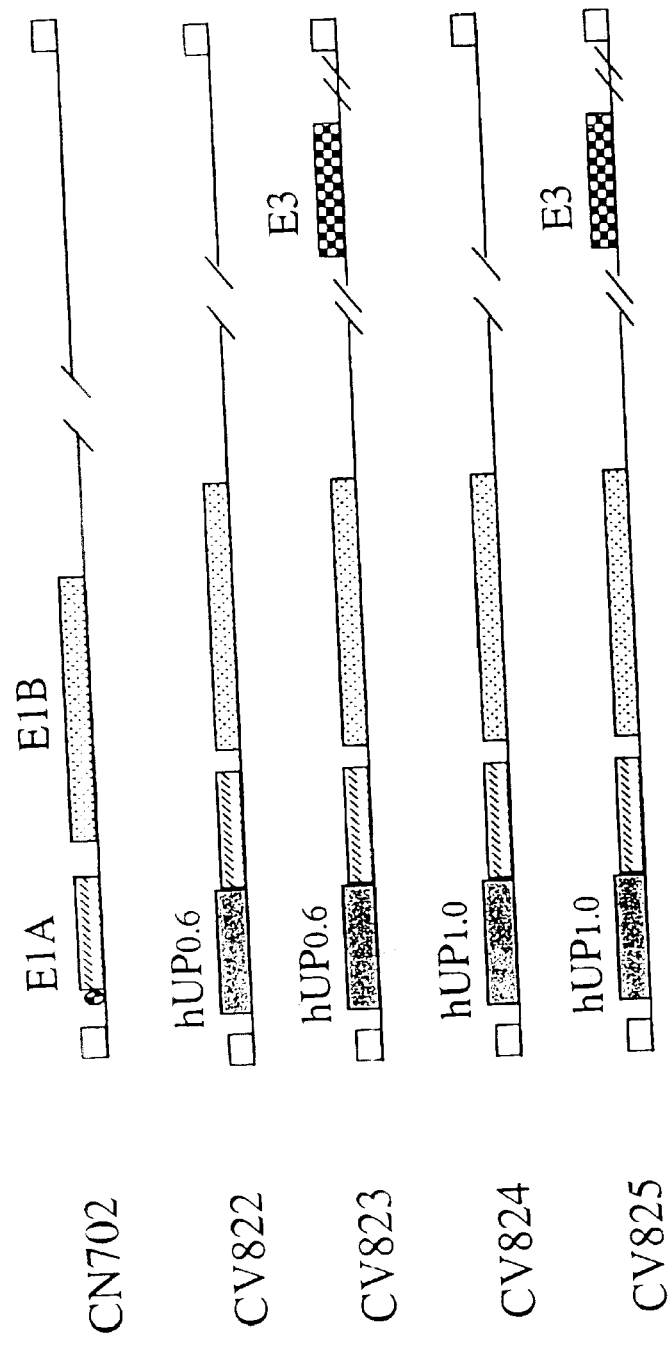
Figure 4C:
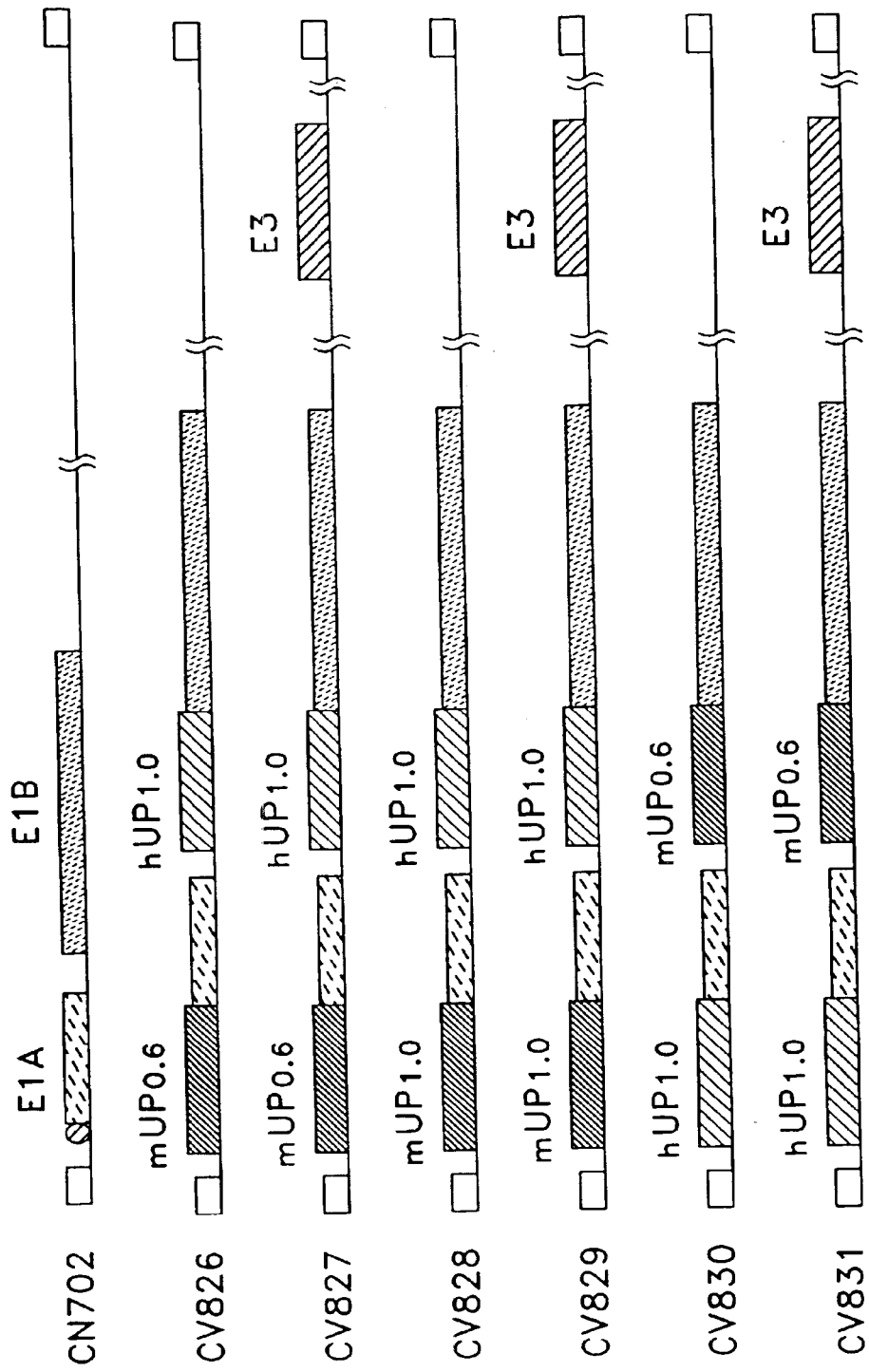
Figure 4D:
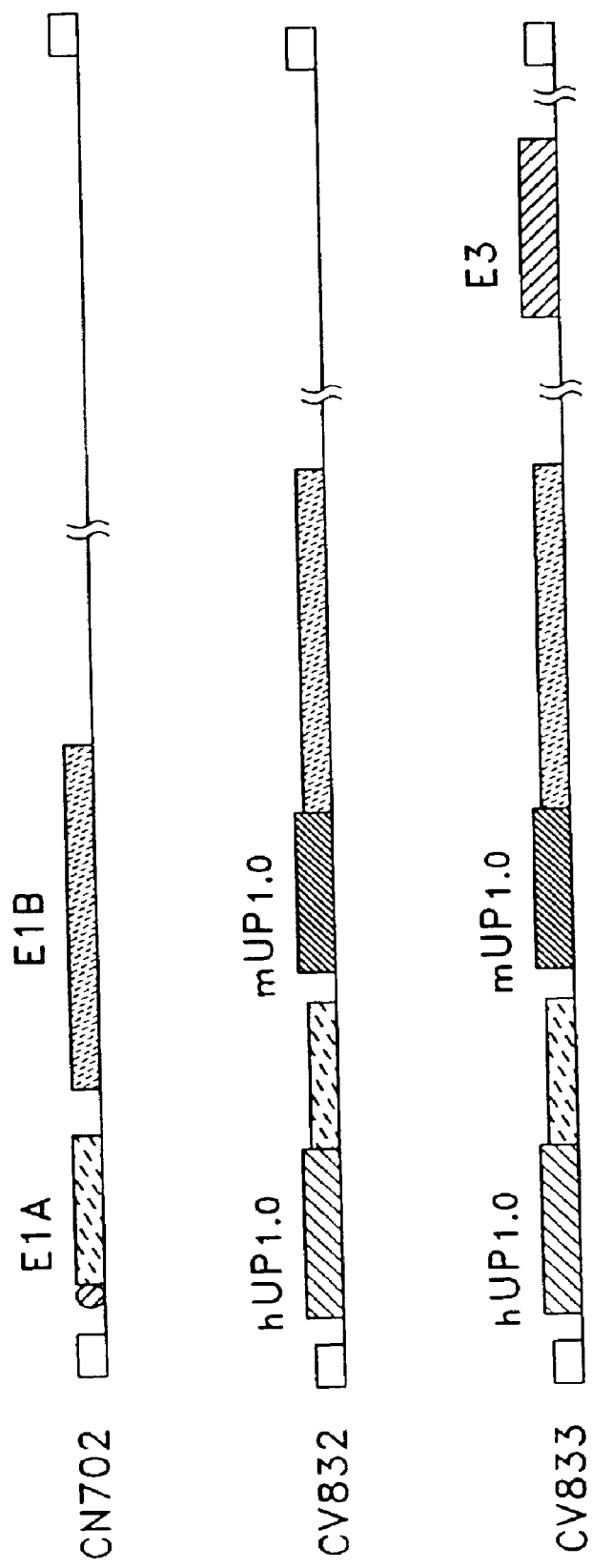
Figure 4E:
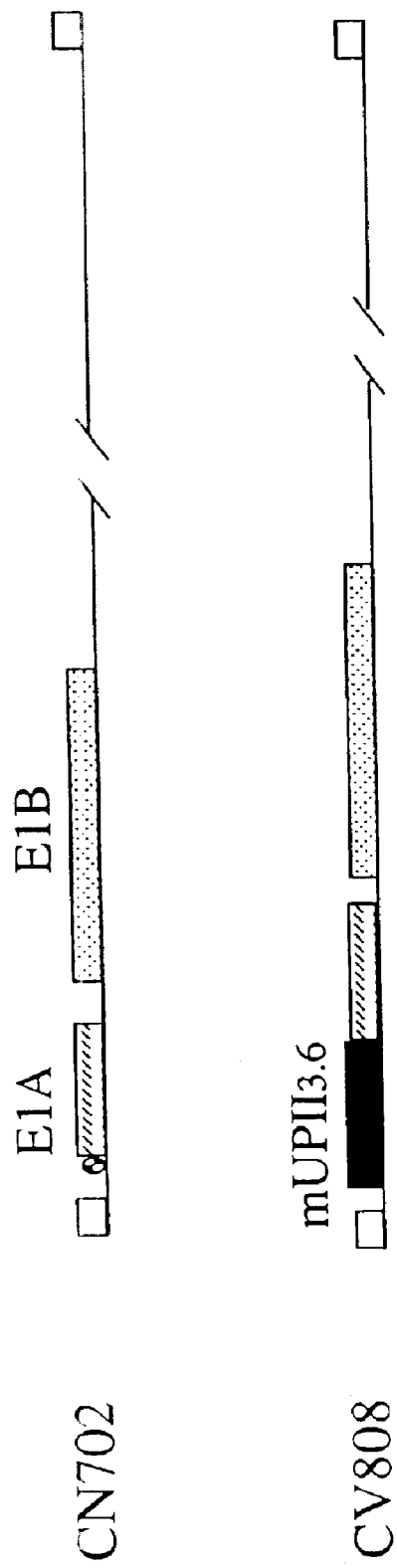
Figure 4F:
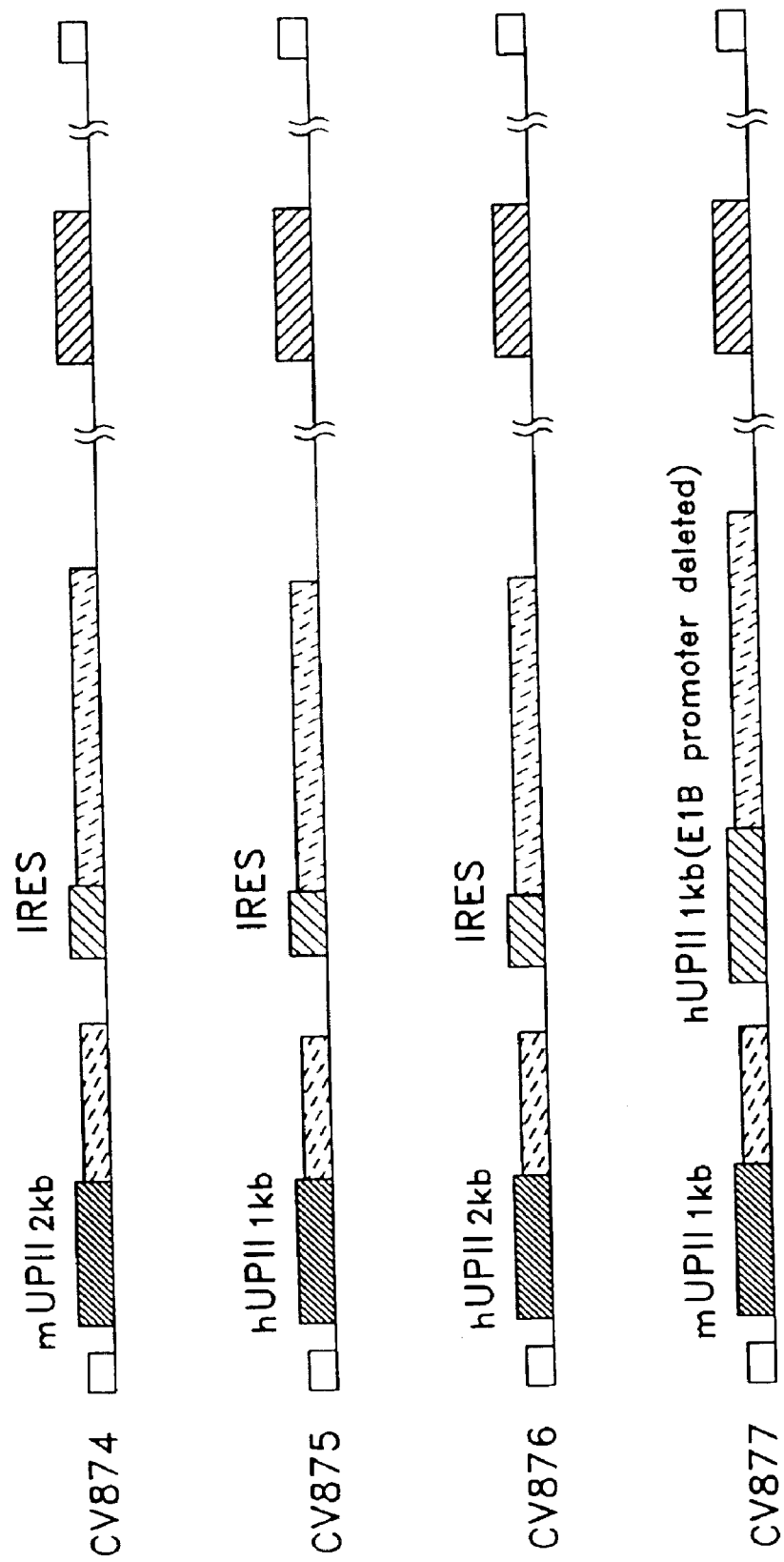

In one embodiment, an early gene such as E1A or E1B gene is under control of a urothelial cell-specific TRE. In one embodiment, E1A and E1B are under control of one or more urothelial cell-specific TREs by making the following construct. A fragment containing the coding region of E1A through the E1B promoter is excised from the Ad genome and reinserted in opposite orientation. In this configuration, the E1A and E1B promoters are next to each other, followed by E1A in opposite orientation (so that neither the E1A or E1B promoters are operatively linked to E1A), followed by E1B in opposite orientation with respect to E1A. A urothelial cell-specific TRE(s) can be inserted between E1A and E1B coding regions, (which are in opposite orientation), so that these regions are under control of the TRE(s). Appropriate promoter sequences are inserted proximal to the E1A and E1B region as shown in FIG. 3. Thus, an urothelial cell-specific TRE may drive both E1A and E1B. Such a configuration may prevent, for example, possible loop-out events that may occur if two urothelial cell-specific TREs were inserted in intact (native) Ad genome, one each 5' of the coding regions of E1A and E1B. By introducing a polycloning site between E1A and E1B, other types of TREs can be inserted, such as a carcinogen embryonic antigen TRE (CEA-TRE); a mucin TRE (MU-TRE); or other cell-specific regulatory elements, preferably those associated with a disease state, such as neoplasm. Thus, this construct may find general use for cell-specific, temporal, or other means of control of adenovirus genes E1A and E1B, thereby providing a convenient and powerful way to render adenoviral replication dependent upon a chosen transcriptional parameter.

In some embodiments, the adenovirus death protein (ADP), encoded within the E3 region, is maintained (i.e. contained) in the adenovirus vector. The ADP gene, under control of the major late promoter (MLP), appears to code for a protein (ADP) that is important in expediting host cell lysis. Tollefson et al. (1996) *J. Virol.* 70(4):2296; Tollefson et al. (1992) *J. Virol.* 66(6):3633. Thus, adenoviral vectors containing the ADP gene may render the adenoviral vector more potent, making possible more effective treatment and/ or a lower dosage requirement.

Accordingly, the invention provides an adenoviral vector that includes a polynucleotide sequence encoding an ADP. A DNA sequence encoding an ADP and the amino acid sequence of an ADP are depicted in SEQ ID NO:3 and SEQ ID NO:4 respectively (FIG. 12). Briefly, an ADP coding sequence is obtained preferably from Ad2 (since this is the strain in which ADP has been more fully characterized) using chniques known in the art, such as PCR. Preferably, the Y leader (which is an important sequence for correct expression of late genes) is also obtained and ligated to the ADP coding sequence. The ADP coding sequence (with or without the Y leader) can then be introduced into the adenoviral genome, for example, in the E3 region (where the ADP coding sequence will be driven by the MLP or the E3 promoter). The ADP coding sequence could also be inserted in other locations of the adenovirus genome, such as the E4 region. The ADP coding sequence could also be operably linked to any of the urothelial-cell specific TREs described herein.

In some embodiments, the invention provides adenoviral vectors which comprise an additional adenovirus gene under transcriptional control of a second urothelial cell-specific TRE. Examples of an additional adenovirus gene under transcriptional control is ADP (discussed above) and genes necessary for replication, such as early genes. For example, an adenoviral vector can be constructed such that a first urothelial cell-specific TRE regulates transcription of one early gene, such as E1A or E1B, and a second urothelial cell-specific TRE regulates transcription of another early gene. These multiple constructs may be more desirable in that they provide more than one source of cell specificity with respect to replication.

Various other replication-competent adenovirus vectors can be made according to the present invention in which, in addition to having an adenovirus gene under control of a urothelial cell-specific TRE, at least one additional gene is placed under control of at least one additional heterologous (non-adenovirus) TRE. This additional TRE(s) can be a cell-, tissue-, and/or cancer-specific TRE. This additional TRE(s) can be another urothelial cell-specific TRE. Optionally, the additional urothelial cell-specific TRE(s) differ from the first. In this way, for example, the possibility of homologous recombination with concomitant loss of intervening sequences can be avoided. The first and additional urothelial cell-specific TREs can, for example, differ in sequence in essential or non-essential regions. For example, the first urothelial cell-specific TRE could comprise a urothelial cell-specific enhancer and a non-urothelial cell-specific promoter; an additional urothelial cell-specific TRE could comprise a non-urothelial cell-specific enhancer and a urothelial cell-specific promoter. Alternatively, the essential portions of the promoter and/or enhancer could be identical in both, with the intervening non-essential regions different. In one embodiment, where one urothelial cell-specific TRE mediates transcription of one gene, and at least one other urothelial cell-specific TRE mediates transcription of another gene, the orientation of the genes is divergent or convergent, rather than tandem. In this way, any recombination between the urothelial cell-specific TREs is unlikely to result to deletion of the intervening sequences.

For example, a urothelial cell-specific TRE can be introduced into an adenovirus vector immediately upstream of and operably linked to an early gene such as E1A, and at least one other urothelial cell-specific TRE with a different sequence can be introduced immediately upstream of and operably linked to another early gene such as E1B. In some embodiments, the adenoviral vector contains two non-identical urothelial TREs that are derived from the same gene or from different genes. In some embodiments, a first TRE is derived from mouse uroplakin II and a second TRE is derived from human uroplakin II.

In some embodiments, an adenoviral vector of the invention comprises an adenoviral gene essential for adenoviral replication under control of a first urothelial cell-specific TRE, and a second adenoviral gene essential for adenoviral replication under control of a second urothelial cell-specific TRE. The first and the second urothelial cell-specific TREs may or may not be substantially identical to one another. By "substantially identical" is meant a requisite degree of sequence identity between the two TREs. The degree of sequence identity between these TREs is at least about 80%, preferably at least about 85%, 90%, 95%, 98%, or 100%. Sequence identity can be determined by a sequence comparison using, i.e., sequence alignment programs that are known in the art, such as those described in *Current Protocols in Molecular Biology* (F. M. Ausubel et al., eds., 1987) Supplement 30, section 7.7.18, Table 7.7.1 A preferred alignment program is ALIGN Plus (Scientific and Educational Software, Pennsylvania), preferably using default parameters. Alternatively, hybridization under stringent conditions can also indicate degree of sequence identity. Adenoviral constructs in which the first and second urothelial cell-specific TREs are substantially identical, particularly if these TREs control transcription of early genes (such as E1A and E1B), may display an instability which may be desirable in certain contexts, such as when an automatic "self-destruction" property can shut down the virus, thereby controlling the degree of propagation.

Stringent conditions for both DNA/DNA and DNA/RNA hybridization are as described by Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al. An example of stringent hybridization conditions is 68° C., 0.2×SSC other examples are provided herein.

In other embodiments, the adenoviral vector comprises an adenoviral gene essential for adenoviral replication under control of a first urothelial cell-specific TRE, and a transgene under control of a second urothelial cell-specific TRE. The first and the second urothelial cell-specific TREs may or may not be substantially identical to one another.

The size of urothelial cell-specific TREs will be determined in part by the capacity of the adenoviral vector, which in turn depends upon the contemplated form of the vector (see below). Generally a minimal size is preferred, as this provides potential room for insertion of other sequences which may be desirable, such as transgenes (discussed below) or additional regulatory sequences. However, if no additional sequences are contemplated, or if, for example, an adenoviral vector will be maintained and delivered free of any viral packaging constraints, a larger urothelial cell-specific TRE may be used as long as the resultant adenoviral vector is rendered replication-competent.

If no adenovirus sequences have been deleted, an adenoviral vector can be packaged with extra sequences totaling up to about 5% of the genome size, or approximately 1.8 kb. If non-essential sequences are removed from the adenovirus genome, then an additional 4.6 kb of insert can be tolerated (i.e., a total of about 1.8 kb plus 4.6 kb, which is about 6.4 kb). Examples of non-essential adenoviral sequences that can be deleted are E3 and E4 (as long as the E4 ORF6 is maintained). A urothelial cell-specific TRE will comprise a polynucleotide sequence of about 3.5 kb, more preferably smaller fragments which are shown to be functional in controlling transcription in a urothelial cell-specific manner.

In order to minimize non-specific replication, endogenous (i.e., adenovirus) TREs should preferably be removed. This would also provide more room for inserts in an adenoviral vector, which may be of special concern if an adenoviral vector will be packaged as a virus (see below). Even more importantly, deletion of endogenous TREs would prevent a possibility of a recombination event whereby a urothelial cell-specific TRE is deleted and the endogenous TRE assumes transcriptional control of its respective adenovirus coding sequences (thus allowing non-specific replication). In one embodiment, an adenoviral vector of the invention is constructed such that the endogenous transcription control sequences of an adenoviral gene(s) are deleted and replaced by a urothelial cell-specific TRE. However, endogenous TREs may also be maintained in the adenovirus vector(s), provided that sufficient cell-specific replication preference is preserved. These embodiments can be constructed by providing a urothelial cell-specific TRE in addition to the endogenous TREs, preferably with the urothelial cell-specific TRE intervening between the endogenous TREs and the replication gene coding segment.

Accordingly, in some embodiments, the E1A promoter is inactivated. In other embodiments, E1A enhancer I is inactivated. In some embodiments, the E1A promoter is inactivated and the E1A enhancer I is inactivated. In other embodiments, an internal ribosome entry site (IRES) is inserted upstream of E1B (with the E1B promoter present or not present), and urothelial cell-specific TRE is operably linked to E1A. In still other embodiments, an internal ribosome entry site (IRES) is inserted upstream of E1B, and urothelial cell-specific TRE is operably linked to E1A, which may or may not maintain the E1A promoter and/or enhancer I (i.e., the E1A promoter and/or enhancer I may be, but not necessarily be, deleted). In other embodiments, the 19-kDa region of E1B is deleted. For adenovirus vectors comprising a second gene under control of an IRES, it is preferred that the endogenous promoter of a gene under translational control of an IRES be deleted so that the endogenous promoter does not interfere with transcription of the second gene. It is preferred that the second gene be in frame with the IRES if the IRES contains an initiation codon. If an initiation codon, such as ATG, is present in the IRES, it is preferred that the initiation codon of the second gene is removed and that the IRES and the second gene are in frame. Alternatively, if the IRES does not contain an initiation codon or if the initiation codon is removed from the IRES, the initiation codon of the second gene is used. Such vectors are described in the Examples. IRES are discussed above and are provided in Table 6 and Table 7.

With respect to all of the adenovirus embodiments described herein, requisite urothelial cell-specific replication preference is indicated by conducting assays that compare replication of the adenovirus vector in a cell that allow a urothelial cell-specific TRE to function with replication in a non-urothelial cell. Generally, a replication differential of at least 2-fold is preferred; more preferably, at least 5-fold; more preferably, at least 10-fold; more preferably, at least 50-fold; even more preferably, at least 100-fold; still more preferably, at least 200-fold; still more preferably, at least about 400-fold to about 500-fold; even more preferably, at least 1000-fold. The acceptable differential can be determined empirically (using, for example, Northern assays or other assays known in the art or assays described in the Example section) and will depend upon the anticipated use of the adenoviral vector and/or the desired result.

Suitable target cells are any cell type that allows a urothelial cell-specific TRE to function. Especially preferred are bladder tumor (carcinoma) cells including, but not limited to, transitional cell carcinoma of the bladder, bladder carcinoma in situ cells, and any metastases of the foregoing. Proteins which are produced by urothelial carcinoma cells but not by normal urothelium include the cytokeratin CK-20. Klein et al. (1998) Cancer 82:349–354; GenBank Accession No. X73502; Swiss-Prot Accession No. P35900. Production of bladder cancer cell-specific proteins such as CK-20 can be measured using assays standard in the art, such as RIA, ELISA or Western blots (immunoassays) to determine levels of CK-20 protein production or Northern blots or PCR to determine levels of CK-20 MRNA production. Alternatively, such cells can be identified and/or characterized by their ability to transcriptionally activate a urothelial cell-specific TRE (i.e., allow a urothelial cell-specific TRE to function).

Any of the various serotypes of adenovirus can be used, such as Ad2, Ad5, Ad12, and Ad40. For purposes of illustration, the serotype Adenovirus 5 (Ad5) is exemplified herein.

The E1A gene is expressed immediately after viral infection (0–2 hours) and before any other viral genes. E1A protein acts as a trans-acting positive-acting transcriptional regulatory factor, and is required for the expression of the other early viral genes E1B , E2, E3, E4, and the promoter-proximal major late genes. Despite the nomenclature, the promoter proximal genes driven by the major late promoter are expressed during early times after Ad5 infection. Flint (1982) Biochem. Biophys. Acta 651:175–208; Flint (1986) Advances Virus Research 31:169–228; Grand (1987) Biochem. J. 241:25–38. In the absence of a functional E1A gene, viral infection does not proceed, because the gene products necessary for viral DNA replication are not produced. Nevins (1989) Adv. Virus Res. 31:35–81. The transcription start site of Ad5 E1A is at 498 and the ATG start site of the E1A protein is at nt 560 in the virus genome.

The E1B protein functions in trans and is necessary for transport of late MnRNA from the nucleus to the cytoplasm.

Defects in E1B expression result in poor expression of late viral proteins and an inability to shut off host cell protein synthesis. The promoter of E1B has been implicated as the defining element of difference in the host range of Ad40and Ad5: clinically Ad40is an enterovirus, whereas Ad5 causes acute conjunctivitis. Bailey, Mackay et al. (1993) *Virology* 193:631; Bailey et al. (1994) *Virology* 202:695–706. E1B proteins are also necessary to overcome restrictions imposed on viral replication by the host cell cycle and also to reduce the apoptotic effects of E1A. Goodrum et al. (1997) *J. Virology* 71:548–561. The E1B promoter of Ad5 consists of a single high-affinity recognition site for Sp1 and a TATA box.

Adenovirus E1B 19-kDa (19K) protein is a potent inhibitor of apoptosis and cooperates with E1A to produce oncogenic transformation of primary cells (Rao, et al., 1992, *Cell Biology*, 89:7742–7746). During productive adenovirus infection, E1A stimulates host cell DNA synthesis, thereby causing cells to aberrantly go through the cell cycle. In response to cell cycle deregulation, the host cell undergoes apoptosis. As a defense mechanism, the E1B 19-kDa protein inhibits this E1A-induced apoptosis and allows assembly of viral progeny to be completed before the cell commits suicide. E1B 19-kDa conducts anti-apoptotic function by multiple mechanisms. E1B 19-kDa inhibits the apoptosis of multiple stimuli, including E1a, p53 and TNF, for example. According to wild-type Ad5, the E1B 19-kDa region is located between nucleotide 1714 and nucleotide 2244. The E1B 19-kDa region has been described in, for example, Rao et al., *Proc. Natl. Acad. Sci. USA*, 89:7742–7746.

The E2 region of adenovirus codes for proteins related to replication of the adenoviral genome, including the 72-kDa DNA-binding protein, the 80-kDa precursor terminal protein and the viral DNA polymerase. The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1A transactivator protein, the E2 early promoter is crucial during the early phases of viral replication.

The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site.

For a detailed review of the E2 promoter architecture see Swaminathan et al., *Curr. Topics in Microbiol. and Immunol.* (1995) 199 part 3:177–194.

The E2 late promoter overlaps with the coding sequences of a gene encoded by the counterstrand and is therefore not amenable for genetic manipulation. However, the E2 early promoter overlaps only for a few base pairs with sequences coding for a 33 kDa protein on the counterstrand. Notably, the SpeI restriction site (Ad5 position 27082) is part of the stop codon for the above mentioned 33 kDa protein and conveniently separates the major E2 early transcription initiation site and TATA-binding protein site from the upstream transcription factor binding sites E2F and ATF. Therefore, insertion of a UP-TRE having SpeI ends into the SpeI site in the I-strand would disrupt the endogenous E2 early promoter of Ad5 and should allow urothelial cell-restricted expression of E2 transcripts.

The E4 gene produces a number of transcription products. The E4 region codes for two polypeptides which are responsible for stimulating the replication of viral genomic DNA and for stimulating late gene expression. The protein products of open reading frames (ORFs) 3 and 6 can both perform these fuinctions by binding the 55-kDa protein from E1B and heterodimers of E2F-1 and DP-1. The ORF 6 protein requires interaction with the E1B 55-kDa protein for activity while the ORF 3 protein does not. In the absence of functional protein from ORF 3 and ORF 6, plaques are produced with an efficiency less than $10^{-6}$ that of wild type virus. To further restrict viral replication to cells which permit a urothelial cell-specific TRE to function, E4 ORFs 1–3 can be deleted, making viral DNA replication and late gene synthesis dependent on E4 ORF 6 protein. By combining such a vector with sequences in which the E1B region is regulated by a urothelial cell-specific TRE, a virus can be obtained in which both the E1B function and E4 function are dependent on a urothelial cell-specific TRE driving E1B.

The major late genes relevant to the subject invention are L1, L2, L3, L4 and L5 which encode proteins of the Ad5 virus virion. All of these genes (typically coding for structural proteins) are probably required for adenoviral replication. The late genes are all under the control of the major late promoter (MLP), which is located in Ad5 at about +5986 to about +6048.

Transgenes Under Ranscriptional Control of a Rothelial Cell-specific TRE

Various other replication-competent adenovirus vectors can be made according to the present invention in which, in addition to having a single or multiple adenovirus gene(s) under control of a urothelial cell-specific TRE, a transgene (s) are also under control of a urothelial cell-specific TRE. Transgenes include, but are not limited to, therapeutic transgenes and reporter genes.

Reporter Genes

For example, a urothelial cell-specific TRE can be introduced into an adenovirus vector immediately upstream of and operably linked to an early gene such as E1A or E1B, and this construct may also contain at least one other urothelial cell-specific TRE driving expression of a reporter gene. The reporter gene can encode a reporter protein, including, but not limited to, chloramphenicol acetyl transferase (CAT), β-galactosidase (encoded by the lacZ gene), luciferase, alkaline phosphatase, a green fluorescent protein, and horse radish peroxidase. For detection of a putative cancer cell(s) in a biological sample, the biological sample may be treated with modified adenoviruses in which a reporter gene (e.g., luciferase) is under control of a urothelial cell-specific TRE. The urothelial cell-specific TRE will be transcriptionally active in cells that allow a urothelial cell-specific TRE to function, and luciferase will be produced. This production will allow detection of urothelial cells, including bladder cancer cells such as transitional cell carcinoma, in, for example, a human host or a biological sample. Alternatively, an adenovirus can be constructed in which a gene encoding a product conditionally required for survival (e.g., an antibiotic resistance marker) is under transcriptional control of a urothelial cell-specific TRE. When this adenovirus is introduced into a biological sample, urothelial cells will become antibiotic resistant. An antibiotic can then be introduced into the medium to kill non-urothelial (e.g., non-cancerous) cells.

Therapeutic Transgenes

Transgenes also include genes which may confer a therapeutic effect, such as enhancing cytotoxicity so as to eliminate unwanted target cells. In this way, various genetic capabilities may be introduced into target cells, particularly cancer cells. For example, in certain instances, it may be desirable to enhance the degree and/or rate of cytotoxic activity, due to, for example, the relatively refractory nature or particular aggressiveness of the cancerous target cell. This could be accomplished by coupling the target cell-specific cytotoxic activity with cell-specific expression of, for example, HSV-tk and/or cytosine deaminase (cd), which renders cells capable of metabolizing 5-fluorocytosine (5-FC) to the chemotherapeutic agent 5-fluorouracil (5-FU). Using these types of transgenes may also confer a bystander effect.

Other desirable transgenes that may be introduced via an adenovirus vector(s) include genes encoding cytotoxic proteins, such as the A chains of diphtheria toxin, ricin or abrin (Palmiter et al. (1987) Cell 50: 435; Maxwell et al. (1987) Mol. Cell. Biol. 7: 1576; Behringer et al. (1988) Genes Dev. 2: 453; Messing et al. (1992) Neuron 8: 507; Piatak et al. (1988) J. Biol. Chem. 263: 4937; Lamb et al. (1985) Eur. J. Biochem. 148: 265; Frankel et al. (1989) Mol. Cell. Biol. 9: 415), genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly; genes that encode an engineered cytoplasmic variant of a nuclease (e.g. RNase A) or protease (e.g. awsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFN-$\alpha$, -$\beta$, -$\gamma$, TNF-$\alpha$, -$\beta$, TGF-$\alpha$, -$\beta$, NGF, and the like. The positive effector genes could be used in an earlier phase, followed by cytotoxic activity due to replication.

E3-containing Urothelial Cell-specific Adenoviral Vectors

The invention provides urothelial cell-specific adenovirus vectors comprising an E3 region, or a portion of an E3 region, and an adenoviral gene under transcriptional control of a urothelial cell-specific TRE. Preferably, the vectors are replication-competent. Inclusion of the E3 region of adenovirus can enhance cytotoxicity of the urothelial cell-specific adenoviral vectors of the present invention. Adenoviral vectors containing an E3 region may maintain their high level of specificity and can be (a) significantly more cytotoxic; (b) produce higher virus yield including extracellular virus yield; (c) form larger plaques; (d) produce rapid cell death; and (e) kill tumors more efficiently in vivo than vectors lacking the E3 region.

Figure 13:
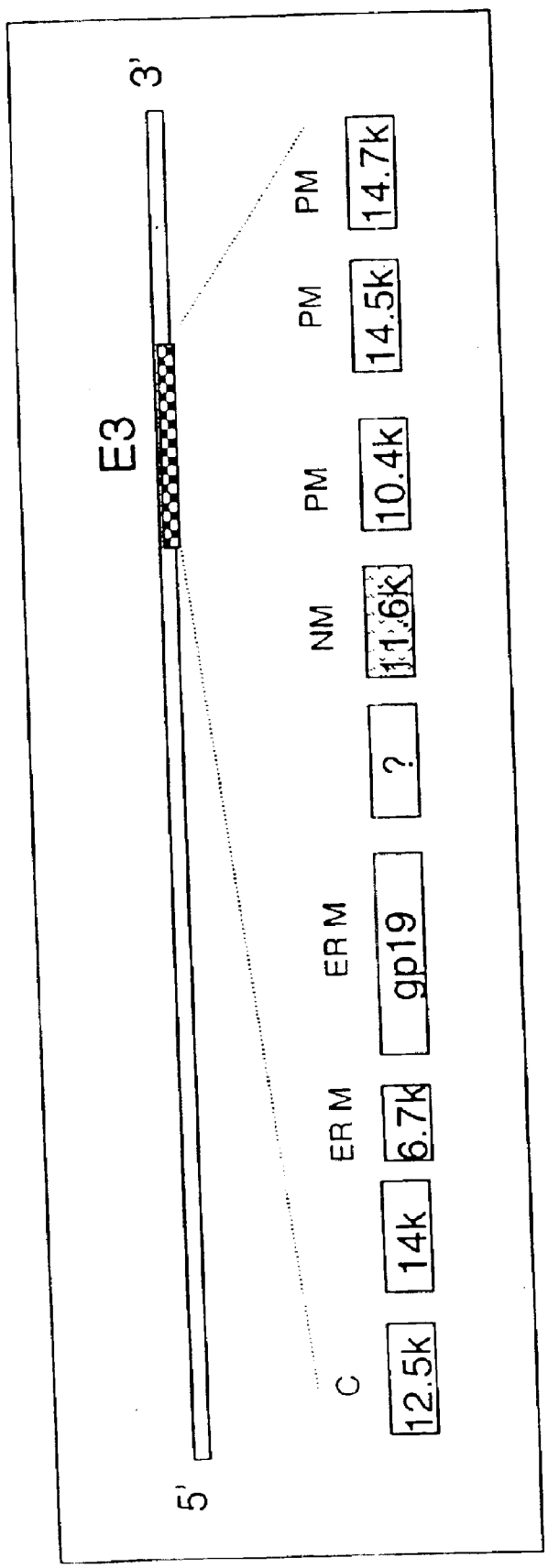
FIG. 13 depicts an E3 region.
Figure 14:
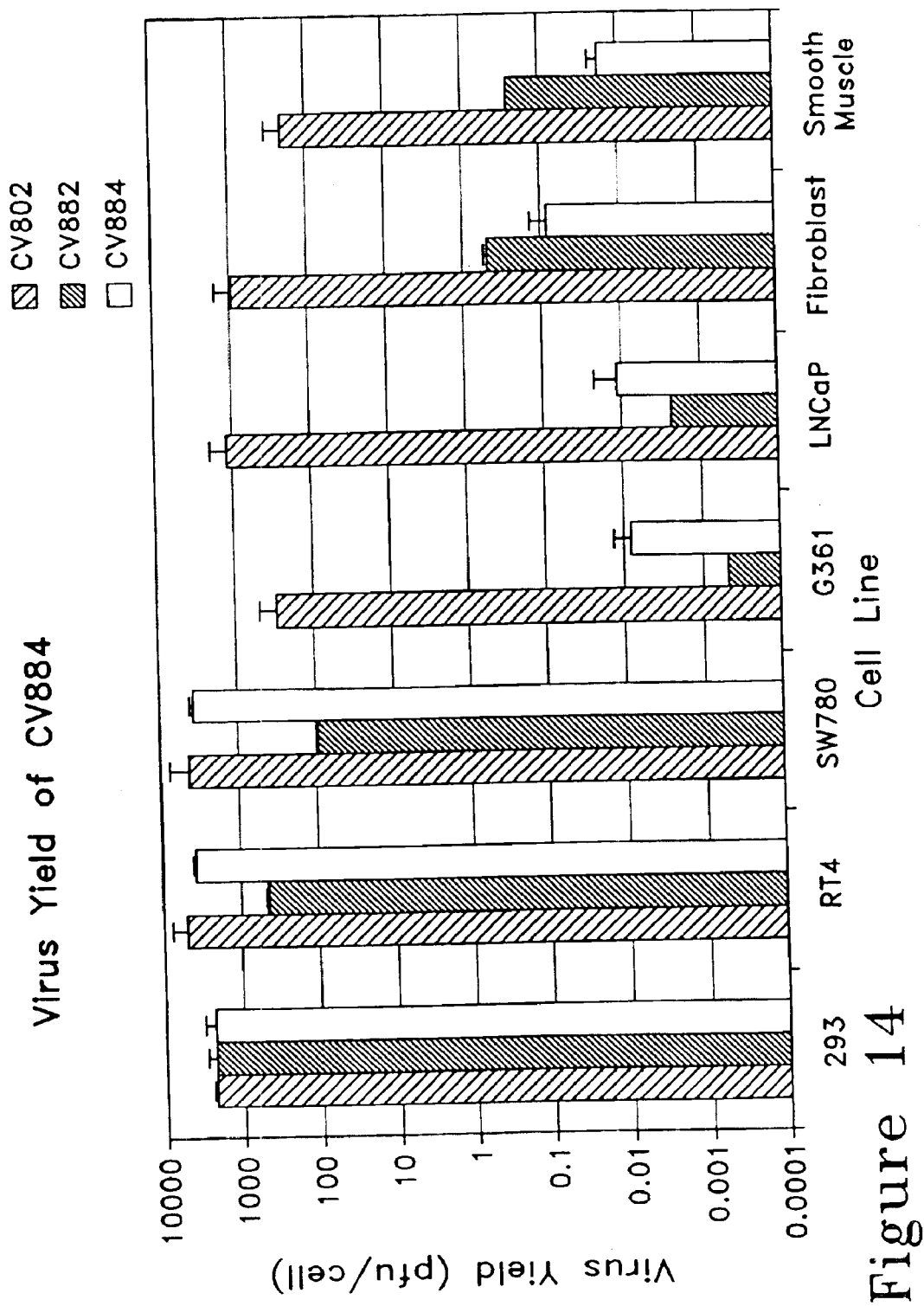
FIG. 14 shows the virus yield of CV802, CV882 and CV884 in cell lines.

The adenoviral vectors of this invention may contain the E3 region or a portion of the E3 region. It is understood that, as inclusion of E3 confers observable and measurable functionality on the adenoviral vectors, for example, increased replication and production, functionally equivalent (in which functionality is essentially maintained, preserved, or even enhanced or diminished) variants of E3 may be constructed. For example, portions of E3 may be used. As is explained in the definition of "portion" of E3, a portion may be, non-inclusively, either of the following: (a) deletion, preferably at the 3' end; (b) inclusion of one or more various open reading frames of E3. Five proteins which are encoded by the Ad-E3 region have been identified and characterized: (1) a 19-kDa glycoprotein (gp19 k) is one of the most abundant adenovirus early proteins, and is known to inhibit transport of the major histocompatibility complex class I molecules to the cell surface, thus impairing both peptide recognition and clearance of Ad-infected cells by cytotoxic T lymphocytes (CTLs); (2) E3 14.7 k protein and the E3 10.4 k/14.5 k complex of proteins inhibit the cytotoxic and inflammatory responses mediated by tumor necrosis factor (TNF); (3) E3 10.4 k/14.5 k protein complex down regulates the epidermal growth factor receptor, which may inhibit inflammation and activate quiescent infected cells for efficient virus replication; (4) E3 11.6 k protein (adenoviral death protein, ADP) from adenovirus 2 and 5 appears to promote cell death and release of virus from infected cells. The functions of three E3-encoded proteins—3.6 k, 6.7 k and 12.5 k—are unknown. A ninth protein having a molecular weight of 7.5 kDa has been postulated to exist, but has not been detected in cells infected with wild-type adenovirus. Wold et al. (1995) Curr. Topics Microbiol. Immunol. 199:237–274. The E3 region is schematically depicted in FIG. 13. These intact, portions, or variants of E3 may be readily constructed using standard knowledge and techniques in the art. Preferably, an intact E3 region is used.

In the adenovirus vectors of the present invention, E3 may or may not be under transcriptional control of native adenoviral transcriptional control element(s). The E3 promoter is located within the coding sequence for virion protein VIII, an essential protein which is highly conserved among adenovirus serotypes. In some embodiments, E3 is under transcriptional control of a heterologous TRE, including, but not limited to, a urothelial cell-specific TRE. Accordingly, in one embodiment, the invention provides an adenoviral vector, preferably replication competent, that comprises E3 region (or a portion of E3) under transcriptional control of a urothelial cell-specific TRE. In other embodiments, the E3 region is under transcriptional control of a native adenoviral TRE, and the vector further comprises an adenoviral gene essential for replication under transcriptional control of a urothelial cell-specific TRE. In other embodiments, the E3 region is under transcriptional control of a urothelial cell-specific TRE, and the vector further comprises an adenoviral gene essential for replication under transcriptional control of a urothelial cell-specific TRE.

Forms and Administration of Adenoviral Vectors

The adenoviral vectors can be used in a variety of forms, including, but not limited to, naked polynucleotide (usually DNA) constructs. Adenoviral vectors can, alternatively, comprise polynucleotide constructs that are complexed with agents to facilitate entry into cells, such as cationic liposomes or other cationic compounds such as polylysine; packaged into infectious adenovirus particles (which may render the adenoviral vector(s) more immunogenic); packaged into other particulate viral forms such as HSV or AAV; complexed with agents (such as PEG) to enhance or dampen an immune response; complexed with agents that facilitate in vivo transfection, such as DOTMA™, DOTAP™, and polyamines.

If an adenoviral vector comprising an adenovirus polynucleotide is packaged into a whole adenovirus (including the capsid), the adenovirus itself may also be selected to further enhance targeting. For example, adenovirus fibers mediate primary contact with cellular receptor(s) aiding in tropism. See, e.g., Amberg et al. (1997) Virol 227:239–244. If a particular subgenus of an adenovirus serotype displayed tropism for a target cell type and/or reduced affinity for non-target cell types, such subgenus(or subgenera) could be used to further increase cell-specificity of cytotoxicity and/or cytolysis.

The adenoviral vectors may be delivered to the target cell in a variety of ways, including, but not limited to, liposomes, general transfection methods that are well known in the art, such as calcium phosphate precipitation, electroporation, direct injection, and intravenous infusion. The means of delivery will depend in large part on the particular adenoviral vector (including its form) as well as the type and location of the target cells (i.e., whether the cells are in vitro or in vivo).

If used in packaged adenoviruses, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 μg to about 1000 μg of an adenoviral vector can be administered. The adenoviral vector(s) may be administered one or more times, depending upon the intended use and the immune response potential of the host or may be administered as multiple, simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

Host Cells, Compositions and Kits

The present invention also provides host cells comprising (i.e., transformed with) the adenoviral vectors described herein. Both prokaryotic and eukaryotic host cells can be used as long as sequences requisite for maintenance in that host, such as appropriate replication origin(s), are present. For convenience, selectable markers are also provided. Host systems are known in the art and need not be described in detail herein. Prokaryotic host cells include bacterial cells, for example, *E. coli, B. subtilis*, and mycobacteria. Among eukaryotic host cells are yeast, insect, avian, plant, *C. elegans* (or nematode) and mammalian host cells. Examples of fungi (including yeast) host cells are *S. cerevisiae, Kluyveromyces lactis* (*K. lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are cultured human urothelial cells (HUC), KU-1, MYP3 (a non-tumorigenic rat urothelial cell line), 804G (rat bladder carcinoma cell line), HCV-29, UM-UC-3, SW780, RT4, HL60, KG-1, and KG-1A. COS cells, mouse L cells, LNCaP cells, Chinese hamster ovary (CHO) cells, human embryonic kidney (HEK) cells, and African green monkey cells. *Xenopus laevis* oocytes, or other cells of amphibian origin, may also be used.

The present invention also includes compositions, including pharmaceutical compositions, containing the adenoviral vectors described herein. Such compositions are useful for administration in vivo, for example, when measuring the degree of transduction and/or effectiveness of cell killing in an individual. Compositions can comprise an adenoviral vector(s) of the invention and a suitable solvent, such as a physiologically acceptable buffer. These are well known in the art. In other embodiments, these compositions further comprise a pharmaceutically acceptable excipient. These compositions, which can comprise an effective amount of an adenoviral vector of this invention in a pharmaceutically acceptable excipient, are suitable for systemic or local administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in *Remington's Pharmaceutical Sciences,* 19th Edition, Mack Publishing (1995). Compositions also include lyophilized and/or reconstituted forms of the adenoviral vectors (including those packaged as a virus, such as adenovirus) of the invention.

The present invention also encompasses kits containing an adenoviral vector(s) of this invention. These kits can be used for diagnostic and/or monitoring purposes, preferably monitoring. Procedures using these kits can be performed by clinical laboratories, experimental laboratories, medical practitioners, or private individuals. Kits embodied by this invention allow someone to detect the presence of bladder cancer cells in a suitable biological sample, such as biopsy specimens.

The kits of the invention comprise an adenoviral vector described herein in suitable packaging. The kit may optionally provide additional components that are useful in the procedure, including, but not limited to, buffers, developing reagents, labels, reacting surfaces, means for detection, control samples, instructions, and interpretive information.

Preparation of the Adenovirus Vectors of the Invention

The adenovirus vectors of this invention can be prepared using recombinant techniques that are standard in the art. Generally, a urothelial cell-specific TRE is inserted 5' to the adenoviral gene of interest, preferably an adenoviral replication gene, more preferably one or more early replication genes (although late gene(s) can be used). A urothelial cell-specific TRE can be prepared using oligonucleotide synthesis (if the sequence is known) or recombinant methods (such as PCR and/or restriction enzymes). Convenient restriction sites, either in the natural adeno-DNA sequence or introduced by methods such as PCR or site-directed mutagenesis, provide an insertion site for a urothelial cell-specific TRE. Accordingly, convenient restriction sites for annealing (i.e., inserting) a urothelial cell-specific TRE can be engineered onto the 5' and 3' ends of a UP-TRE using standard recombinant methods, such as PCR.

Polynucleotides used for making adenoviral vectors of this invention may be obtained using standard methods in the art, such as chemical synthesis, recombinant methods and/or obtained from biological sources.

Adenoviral vectors containing all replication-essential elements, with the desired elements (e.g., E1A) under control of a urothelial cell-specific TRE, are conveniently prepared by homologous recombination or in vitro ligation of two plasmids, one providing the left-hand portion of adenovirus and the other plasmid providing the right-hand region, one or more of which contains at least one adenovirus gene under control of a urothelial cell-specific TRE. If homologous recombination is used, the two plasmids should share at least about 500 bp of sequence overlap. Each plasmid, as desired, may be independently manipulated, followed by cotransfection in a competent host, providing complementing genes as appropriate, or the appropriate transcription factors for initiation of transcription from a urothelial cell-specific TRE for propagation of the adenovirus. Plasmids are generally introduced into a suitable host cell such as 293 cells using appropriate means of transduction, such as cationic liposomes. Alternatively, in vitro ligation of the right and left-hand portions of the adenovirus genome can also be used to construct recombinant adenovirus derivative containing all the replication-essential portions of adenovirus genome. Berkner et al. (1983) *Nucleic Acid Research* 11: 6003–6020; Bridge et al. (1989) *J. Virol.* 63: 631–638.

For convenience, plasmids are available that provide the necessary portions of adenovirus. Plasmid pXC.1 (McKinnon (1982) *Gene* 19:33–42) contains the wild-type left-hand end of Ad5. pBHG10 (Bett et al. (1994); Microbix Biosystems Inc., Toronto) provides the right-hand end of Ad5, with a deletion in E3. The deletion in E3 provides room in the virus to insert a 3 kb urothelial cell-specific TRE without deleting the endogenous enhancer/promoter. The gene for E3 is located on the opposite strand from E4 (r-strand). pBHG11 provides an even larger E3 deletion (an additional 0.3 kb is deleted). Bett et al. (1994). Alternatively, the use of pBHGE3 (Microbix Biosystems, Inc.) provides the right hand end of Ad5, with a full-length of E3.

For manipulation of the early genes, the transcription start site of Ad5 E1A is at 498 and the ATG start site of the E1A coding segment is at 560 in the virus genome. This region can be used for insertion of a urothelial cell-specific TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a nucleotide sequence change resulting in a unique restriction site, one can provide for insertion of urothelial cell-specific TRE at that site. Example 3 provides a more detailed description of an adenoviral vector in which E1A is under urothelial cell-specific TRE control.

A similar strategy may also be used for insertion of a urothelial cell-specific TRE element to regulate E1B. The E1B promoter of Ad5 consists of a single high-affinity recognition site for Sp1 and a TATA box. This region extends from Ad5 nt 1636 to 1701. By insertion of a urothelial cell-specific TRE in this region, one can provide for cell-specific transcription of the E1B gene. By employing the left-hand region modified with the cell-specific response element regulating E1A, as the template for introducing a urothelial cell-specific TRE to regulate E1B, the resulting adenovirus vector will be dependent upon the cell-specific transcription factors for expression of both E1A and E1B. In some embodiments, the E1B 19-kDa region is deleted. For a deletion of the genomic region encoding the E1 B 19-kDa product in an adenovirus construct, nucleotides encoding the 19-kDa region are deleted. In Ad5, a deletion of the 261base pairs between nucleotide 1713 and nucleotide 1974 results in a deletion of the genomic region encoding the E1B 19-kDa product. Examples 1, 3 and 5 provide a more detailed description of how such constructs can be prepared.

Similarly, a urothelial cell-specific TRE can be inserted upstream of the E2 gene to make its expression cell-specific. The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., Curr. Topics in Micro. and Immunol. (1995) 199(part 3):177–194.

The E2 late promoter overlaps with the coding sequences of a gene encoded by the counterstrand and is therefore not amenable for genetic manipulation. However, the E2 early promoter overlaps only for a few base pairs with sequences coding for a 33 kD protein on the counterstrand. Notably, the SpeI restriction site (Ad5 position 27082) is part of the stop codon for the above mentioned 33 kD protein and conveniently separates the major E2 early transcription initiation site and TATA-binding protein site from the upstream transcription factor binding sites E2F and ATF. Therefore, insertion of a urothelial cell-specific TRE having SpeI ends into the SpeI site in the 1-strand would disrupt the endogenous E2 early promoter of Ad5 and should allow urothelial cell-restricted expression of E2 transcripts.

For E4, one must use the right hand portion of the adenovirus genome. The E4 transcription start site is predominantly at about nt 35605, the TATA box at about nt 35631 and the first AUG/CUG of ORFI is at about nt 35532. Virtanen et al. (1984) J. Virol. 51: 822–831. Using any of the above strategies for the other genes, a UP-TRE may be introduced upstream from the transcription start site. For the construction of full-length adenovirus with a urothelial cell-specific TRE inserted in the E4 region, the co-transfection and homologous recombination are performed in W162 cells (Weinberg et al. (1983) Proc. Natl. Acad. Sci. 80:5383–5386) which provide E4 proteins in trans to complement defects in synthesis of these proteins.

Adenoviral constructs containing an E3 region can be generated as described in Example 3, wherein homologous recombination between an E3-containing adenoviral plasmid, for example, BHGE3 (Microbix Biosystems Inc., Toronto) and a non-E3-containing adenoviral plasmid, is carried out.

Alternatively, an adenoviral vector comprising an E3 region can be introduced into cells, for example 293 cells, along with an adenoviral construct or an adenoviral plasmid construct, where they can undergo homologous recombination to yield adenovirus containing an E3 region. In this case, the E3-containing adenoviral vector and the adenoviral construct or plasmid construct contain complementary regions of adenovirus, for example, one contains the left-hand and the other contains the right-hand region, with sufficient sequence overlap as to allow homologous recombination.

Alternatively, an E3-containing adenoviral vector of the invention can be constructed using other conventional methods including standard recombinant methods (e.g., using restriction nucleases and/or PCR), chemical synthesis, or a combination of any of these. Further, deletions of portions of the E3 region can be created using standard techniques of molecular biology.

Methods of packaging adenovirus polynucleotides into adenovirus particles are known in the art and are described in the Examples.

Methods Using the Adenovirus Vectors of the Invention

The subject vectors can be used for a wide variety of purposes, which will vary with the desired or intended result. Accordingly, the present invention includes methods using the adenoviral vectors described above.

In one embodiment, methods are provided for conferring selective cytotoxicity in cells that allow a urothelial cell-specific TRE to function, preferably urothelial cells, comprising contacting such cells with an adenovirus vector described herein. Cytotoxicity can be measured using standard assays in the art, such as dye exclusion, $^3$H-thymidine incorporation, and/or lysis.

In another embodiment, methods are provided for propagating an adenovirus specific for cells which allow a urothelial cell-specific TRE to function, preferably urothelial cells, preferably bladder cancer cells. These methods entail combining an adenovirus vector with the cells, whereby said adenovirus is propagated.

Another embodiment provides methods for killing cells that allow a urothelial cell-specific TRE to function in a mixture of cells, comprising combining the mixture of cells with an adenovirus vector of the present invention. The mixture of cells is generally a mixture of normal cells and cancerous cells that allow a urothelial cell-specific TRE to function, and can be an in vivo mixture or in vitro mixture.

The invention also includes methods for detecting cells which allow a urothelial cell-specific TRE to function, such as bladder cancer cells, in a biological sample. These methods are particularly useful for monitoring the clinical and/or physiological condition of an individual (i.e., mammal), whether in an experimental or clinical setting. In one method, cells of a biological sample are contacted with an adenovirus vector, and replication of the adenoviral vector is detected. Alternatively, the sample can be contacted with an adenovirus in which a reporter gene is under control of a urothelial cell-specific TRE. When such an adenovirus is introduced into a biological sample, expression of the reporter gene indicates the presence of cells that allow a urothelial cell-specific TRE to function. Alternatively, an adenovirus can be constructed in which a gene conditionally required for cell survival is placed under control of a urothelial cell-specific TRE. This gene may encode, for example, antibiotic resistance. Later the biological sample is treated with an antibiotic. The presence of surviving cells expressing antibiotic resistance indicates the presence of cells capable of urothelial cell-specific TRE function. A suitable biological sample is one in which cells that allow a urothelial cell-specific TRE to function, such as bladder cancer cells, may be or are suspected to be present. Generally, in mammals, a suitable clinical sample is one in which cancerous cells that allow a urothelial cell-specific TRE to function, such as bladder carcinoma cells, are suspected to be present. Such cells can be obtained, for example, by needle biopsy or other surgical procedure. Cells to be contacted may be treated to promote assay conditions, such as selective enrichment, and/or solubilization. In these methods, cells that allow a urothelial cell-specific TRE to function can be detected using in vitro assays that detect adenoviral proliferation, which are standard in the art. Examples of such standard assays include, but are not limited to, burst assays (which measure virus yield) and plaque assays (which measure infectious particles per cell). Propagation can also be detected by measuring specific adenoviral DNA replication, which are also standard assays.

The invention also provides methods of modifying the genotype of a target cell, comprising contacting the target cell with an adenovirus vector described herein, wherein the adenoviral vector enters the cell.

The invention further provides methods of suppressing tumor cell growth, preferably a tumor cell that allows a urothelial cell-specific TRE to function, comprising contacting a tumor cell with an adenoviral vector of the invention such that the adenoviral vector enters the tumor cell and exhibits selective cytotoxicity for the tumor cell. For these methods, the adenoviral vector may or may not be used in conjunction with other treatment modalities for tumor suppression, such as chemotherapeutic agents (such as those listed below), radiation and/or antibodies.

The invention also provides methods of lowering the levels of a tumor cell marker in an individual, comprising administering to the individual an adenoviral vector of the present invention, wherein the adenoviral vector is selectively cytotoxic toward cells that allow a urothelial cell-specific TRE to function. Tumor cell markers include, but are not limited to, CK-20. Methods of measuring the levels of a tumor cell marker are known to those of ordinary skill in the art and include, but are not limited to, immunological assays, such as enzyme-linked immunosorbent assay (ELISA), using antibodies specific for the tumor cell marker. In general, a biological sample is obtained from the individual to be tested, and a suitable assay, such as an ELISA, is performed on the biological sample. For these methods, the adenoviral vector may or may not be used in conjunction with other treatment modalities for tumor suppression, such as chemotherapeutic agents (such as those listed below), radiation and/or antibodies.

The invention also provides methods of treatment, in which an effective amount of an adenoviral vector(s) described herein is administered to an individual. Treatment using an adenoviral vector(s) is indicated in individuals with bladder cancer as described above. Also indicated are individuals who are considered to be at risk for developing bladder cancer (including single cells), such as those who have had disease which has been resected and those who have had a family history of bladder cancer. Determination of suitability of administering adenoviral vector(s) of the invention will depend, inter alia, on assessable clinical parameters such as serological indications and histological examination of tissue biopsies. Generally, a pharmaceutical composition comprising an adenoviral vector(s) in a pharmaceutically acceptable excipient is administered. Pharmaceutical compositions are described above. For these methods, the adenoviral vector may or may not be used in conjunction with other treatment modalities for tumor suppression, such as chemotherapeutic agents (such as those listed below), radiation and/or antibodies.

The amount of adenoviral vector(s)to be administered will depend on several factors, such as route of administration, the condition of the individual, the degree of aggressiveness of the disease, the particular urothelial cell-specific TRE employed, and the particular vector construct (i.e., which adenovirus gene(s) is under urothelial cell-specific TRE control), as well as whether the adenoviral vector is used in conjunction with other treatment modalities.

If administered as a packaged adenovirus, from about $10^4$ to about $10^{14}$, preferably from about $10^4$ to about $10^{12}$, more preferably from about $10^4$ to about $10^{10}$. If administered as a polynucleotide construct (i.e., not packaged as a virus), about 0.01 µg to about 100 µg can be administered, preferably 0.1 µg to about 500 µg, more preferably about 0.5 µg to about 200 µg. More than one adenoviral vector can be administered, either simultaneously or sequentially. Administrations are typically given periodically, while monitoring any response. Administration can be given, for example, intratumorally, intravenously or intraperitoneally.

The adenoviral vectors of the invention can be used alone or in conjunction with other active agents, such as chemotherapeutics, that promote the desired objective. Examples of chemotherapeutics which are suitable for suppressing bladder tumor growth are BGC (bacillus Calmett-Guerin); mitomycin-C; cisplatin; thiotepa; doxorubicin; methotrexate; paclitaxel (TAXOL™); ifosfamide; gallium nitrate; gemcitabine; carboplatin; cyclosphasphamid; vinblastine; vincristin; fluorouracil; etoposide; bleomycin. Examples of combination therapies include (CISCA (cyclophosphamide, doxorubicin, and cisplatin); CMV (cisplatin, methotrexate, vinblastine); MVMJ. (methodtrextate, vinblastine, mitoxantrone, carboplain); CAP (cyclophosphamide, doxorubicin, cisplatin); NVAC (methotrexate, vinblastine, doxorubicin, cisplatin). Radiation may also be combined with chemotherapeutic agent(s), for example, radiation with cisplatin. Administration of the chemotherapeutic agents is generally intravesical (directly into the bladder) or intravenous.

The following examples are provided to illustrate but not limit the invention.

EXAMPLES

Example 1

Mouse and Human Uroplakin-derived Urothelial Cell-specific TRE Constructs

A 3.6 kb portion of 5'-flanking DNA a mouse UPII was amplified from mouse genomic DNA using PCR with primers 66.119.1 and 66.119.2.

66.119.1 (5'-ACCGGTCTCGAGGATCTCGGCC-CTTTC-3', SEQ ID NO:5)

66.119.2 (5'-ACCGGTACTGCGCTGGGACTGGATCC-3', SEQ ID NO:6)

The amplified fragment was purified, then "TA" cloned by ligation into pGEM-T (Promega) to created plasmid CN568. The entire insert was amplified from CN568 with primers 100.24.1 (5'-AAGCTTACCGGTACTGCGCTGGGACT-GGATCCTG-3', SEQ ID NO:7) and 100.27.1 (5'-ACCAT-GGACCGGTCTCGAGGATCTCGGCCCTCTTTC-3', SEQ ID NO:8), purified, and ligated into pGEM-T to create plasmid CP616. CP616 was digested with HindIII and SpeI, blunted and ligated into pGL3-Basic (Promega) which had been digested with HindIII and MluI and blunted, creating plasmid CP620. CP620 contains the 3.6 kb mUPII 5'-flanking DNA (nucleotides −3531 to +60) in operable linkage with the luc+ gene.

Plasmids CP619 and CP618 were created with a similar strategy. A 1.0 kb fragment (−965 to +1) of the 5' flanking DNA from the mUPII gene with primers 100.24.1 and 100.24.3 (5'-ACCATGGACCGGTACGTACCCAATCT-GTTGTCCCAG-3', SEQ ID NO:9) and a 600 bp fragment (−587 to +1) of the 5'-flanking DNA from the mUPII gene was amplified with 100.24.1 and 100.24.2 (5'-ACCATGGACCGGTCACTAGCCTTGCTGGACTGGAC-3', SEQ ID NO:10). Each fragment was purified then TA cloned into pGEM-T, creating CP615 and CP614, respectively. The 1.0 and 0.6 kb fragments were excised from CP615 and CP614 by digestion with SpeI, purified, blunted and digested with HindIII, then ligated into pGL3-Basic (Promega) which had been digested with MluI, blunted, and digested with HindIII, creating plasmids CP619 and CP618, respectively.

5' flanking DNA from human UPII was isolated from human genomic DNA using a Human GenomeWalker kit from Clontech (Palo Alto, Calif.) according to the manufacturer's instructions. Briefly, a first PCR reaction was performed using the AP1 primer supplied in the kit in combination with a hUPII-specific 3' primer, 100.84.1, which is complementary to positions +24 to +47 of the hUPII gene (5'-AAGAATCAGGATCAAGGGCAAGTC-3', SEQ ID NO:11). The product of the first PCR reaction was then amplified a second time using a nested set of primers consisting of AP2 (supplied in the kit) and 100.84.2, which is complementary to positions +3 to −22 of the hUPII gene (5'-AATGCTGGGCTGGGAGGTGGAATAG-3', SEQ ID NO:12). Five major amplification products from the second PCR reaction were TA cloned into pGEM-T. One clone, #7, were identified as containing a 2.2 kb segment of DNA from the 5'-flanking region of hUPII. The 2:2 kb segment was subcloned by amplification using primers 100.113.1 (5'-AGGGGTACCCACTATAGGGCACGCGTGGT-3', SEQ ID NO:13) and 100.113.2 (5'-ACCCAAGCTT-GGGATGCTGGGCTGGGAGGTGG-3', SEQ ID NO:14), purification, and TA cloning into pGEM-T, creating CP655. The insert was then excised by digestion with HindIII and SpeI, purified and blunted. The 2.2 (−2225 to +1) kb fragment from CP655 was cloned into pGL3-Basic which had been digested with SacII, blunted, and digested with KpnI, creating CP657. A second clone (#16) contained a 1.0 kb fragment of 5'-flanking DNA. This fragment was subcloned by amplification with primers 100.113.1 and 100.113.2, purification, and TA cloning into pGEM-T to generate CP654. The 1.0 kb insert (−965 to +1) was excised from CP654 with KpnI (blunt) then HindIII, and cloned into pGL3-Basic which had been digested with SacII, blunted, and digested with HindIII to create CP656.

Additional, smaller fragments (0.6 kb and 0.2 kb) of the 5'-flanking region from hUPII were amplified from using 100.126.3 (5'-ACGAGGGGTACCCACCGGTACCG-CATGTGCTCCCTGGCC-3', SEQ ID NO:15) plus 100.126.1 (5'-AGACCCAAGCTTGGGACCGGTA-TGCTGGGCTGGGAGGTGG-3', SEQ ID NO:16) and 100.126.2 (5'-ACGAGGGGTACCCACCGGTCCCC-CCTCCTGGCCTGAGG3', SEQ ID NO:17) plus 100.126.1, respectively, purified, and TA cloned into pGEM-T, creating CP658 and CP659, respectively. CP658 and CP659 were each digested with KpnI and HindIII to excise the 0.6 (−592 to +1) and 0.2 (−211 to +1) kb hUPII 5'-flanking fragments, which were each purified and cloned into pGL3-Basic which had also been digested with KpnI and HindIII, creating CP662 and CP663, respectively.

Two segments of 5'-flanking sequence from human UP1 a were cloned by amplifying human genomic DNA with primers 100.82.1 (5'-AGGGGTACCCCGGCCGGTCA-CACAGCAGGAGAGACAC-3', SEQ ID NO:18) plus 100.82.2:(5'-ACCCAAGCTTGGGCGGCCGCATCCTGG-GACACATGAGCAGG-3', SEQ ID NO:19) and 100.82.2 plus 100.83.1 (5'-AGGGGTACCCCGGCCGCAA-CCCTGCCTTCGAGGTTC-3', SEQ ID NO:20), and TA cloning the amplification products into pGEM-T, creating CP646 (1.0 kb fragment) and CP647 (2.0 kb fragment). CP646 and CP647 were each digested with KpnI and HindIII to excise the inserts, which were each purified and cloned into pGL3-Basic which had been KpnI/HindIII digested, creating CP648 and CP649, respectively. The characteristics of the various plasmids are summarized in Table 1 (FIG. 3).

TABLE 1

| Name | Backbone | Insert Size | Species | Gene | Comments |
|---|---|---|---|---|---|
| CP655 | pGEM-T | 2.2 kb | human | UPII | GenomeWalker product |
| CN568 | pGEM-T | 3.6 kb | mouse | UPII | |
| CP614 | pGEM-T | 0.6 kb | mouse | UPII | Plus restriction sites |
| CP615 | pGEM-T | 1.0 kb | mouse | UPII | Plus restriction sites |
| CP616 | pGEM-T | 3.6 kb | mouse | UPII | Plus restriction sites |
| CP618 | pGL3-Basic | 0.6 kb | mouse | UPII | Plus restriction sites, linked to luc+ |
| CP619 | pGL3-Basic | 1.0 kb | mouse | UPII | Plus restriction sites, linked to luc+ |
| CP620 | pGL3-Basic | 3.6 kb | mouse | UPII | Plus restriction sites, linked to luc+ |
| CP646 | pGEM-T | 1.0 kb | human | UP1a | Plus restriction sites |
| CP647 | pGEM-T | 2.0 kb | human | UP1a | Plus restriction sites |
| CP648 | pGL3-Basic | 2.0 kb | human | UP1a | Plus restriction sites, linked to luc+ |
| CP649 | pGL3-Basic | 1.0 kb | human | UP1a | Plus restriction sites, linked to luc+ |
| CP654 | pGEM-T | 1.0 kb | human | UPII | Plus restriction sites |
| CP655 | pGEM-T | 2.2 kb | human | UPII | Plus restriction sites |
| CP656 | pGL3-Basic | 1.0 kb | human | UPII | Plus restriction sites, linked to luc+ |
| CP657 | pGL3-Basic | 2.2 kb | human | UPII | Plus restriction sites, linked to luc+ |
| CP658 | pGEM-T | 0.6 kb | human | UPII | Plus restriction sites |
| CP659 | pGEM-T | 0.2 kb | human | UPII | Plus restriction sites |
| CP662 | pGL3-Basic | 0.2 kb | human | UPII | Plus restriction sites, linked to luc+ |
| CP663 | pGL3-Basic | 0.6 kb | human | UPII | Plus restriction sites, linked to luc+ |
| CP1066 | pGL3-Basic | 1.9 kb | mouse | UPII | Plus restriction sites, linked to luc+ |

Example 2

Urothelial Cell-specific TRE Reporter Assays

Uroplakin 5'-flanking DNA was tested for the ability to drive urothelial cell-specific expression in a luciferase-based reporter assay. Luciferase expression was assayed in a variety of different cell lines. The cell lines and their sources are listed in Table 2.

TABLE 2

| Name | Source |
| --- | --- |
| HBL-100 | Breast epithelium |
| HepG2 | Hepatocellular carcinoma |
| KB | Oral epidermoid carcinoma |
| LoVo | Colon carcinoma |
| MCF-7 | Breast adenocarcinoma |
| OVCAR | Ovarian adenocarcinoma |
| PA-1 | Ovary teratocarcinoma |
| RT-4 | Transitional bladder cell papilloma |
| SW1463 | Rectal adenocarcinoma |
| SW780 | Bladder cell carcinoma |
| UM-UC-3 | Bladder cell carcinoma |
| Hep 3B | Hepatoma |

Figure 5:
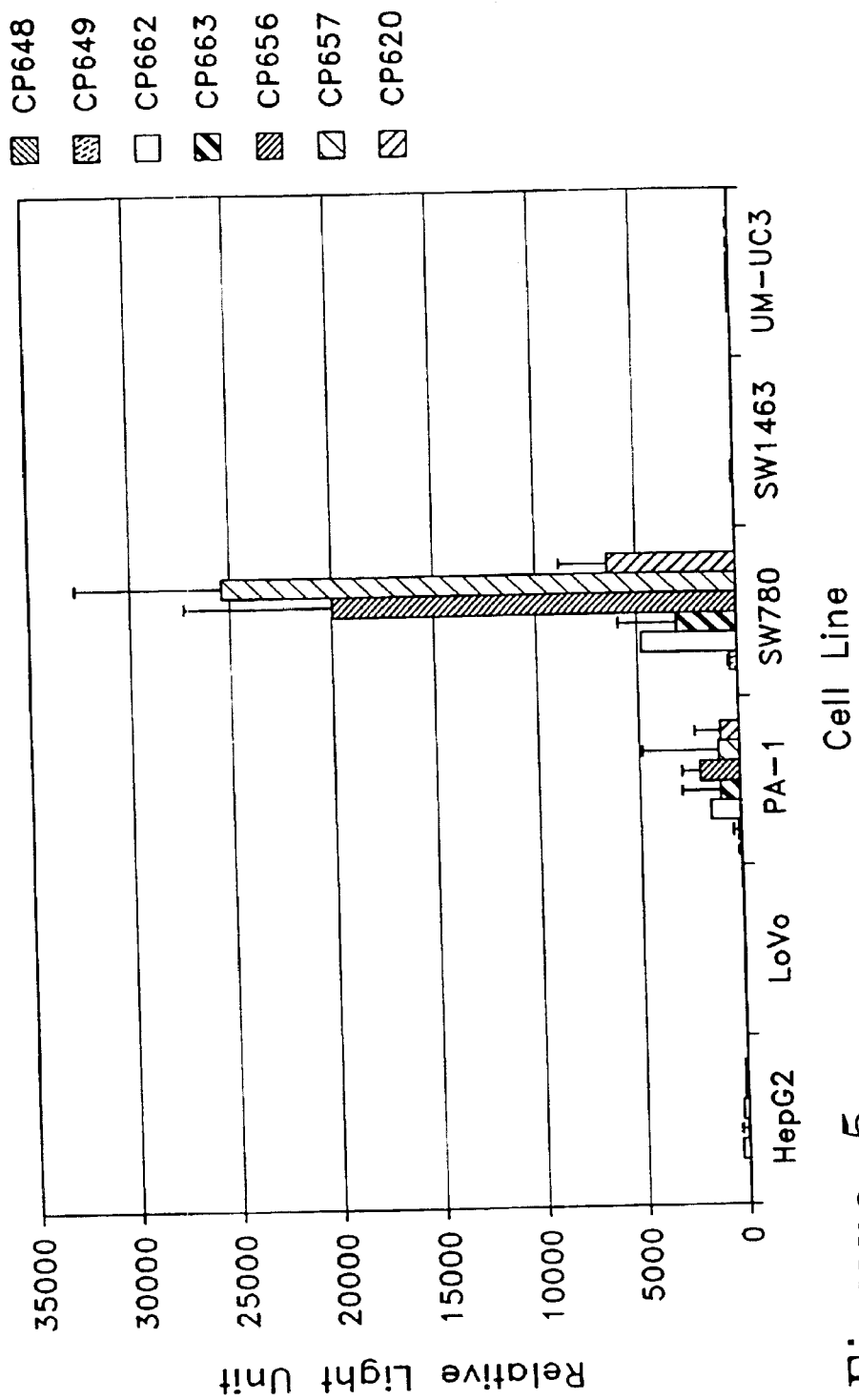
FIG. 5 is a bar graph depicting the results of an assay to assess the bladder specificity of CP648 (TRE for human uroplakin 1A with 2.0 kb flanking sequence 5' to luciferase reporter), CP649 (TRE for human uroplakin 1A with 1.0 kb flanking sequence 5' to luciferase reporter, CP662 (TRE for hUPII with 200 bp flanking sequence 5' to luciferase reporter), CP663 (TRE for human uroplakin II with 600 bp flanking sequence 5' to luciferase reporter), CP656 (TRE for human uroplakin II with 1 kb flanking sequence 5' to luciferase reporter), CP657 (TRE for human uroplakin II with 2.3 kb flanking sequence 5' to luciferase reporter), and CP620 (TRE for mouse uroplakin II with flanking sequence −3531 to +60 that is 5' to luciferase reporter) under the control of human uroplakin II promoter in different cell lines.
Figure 6:
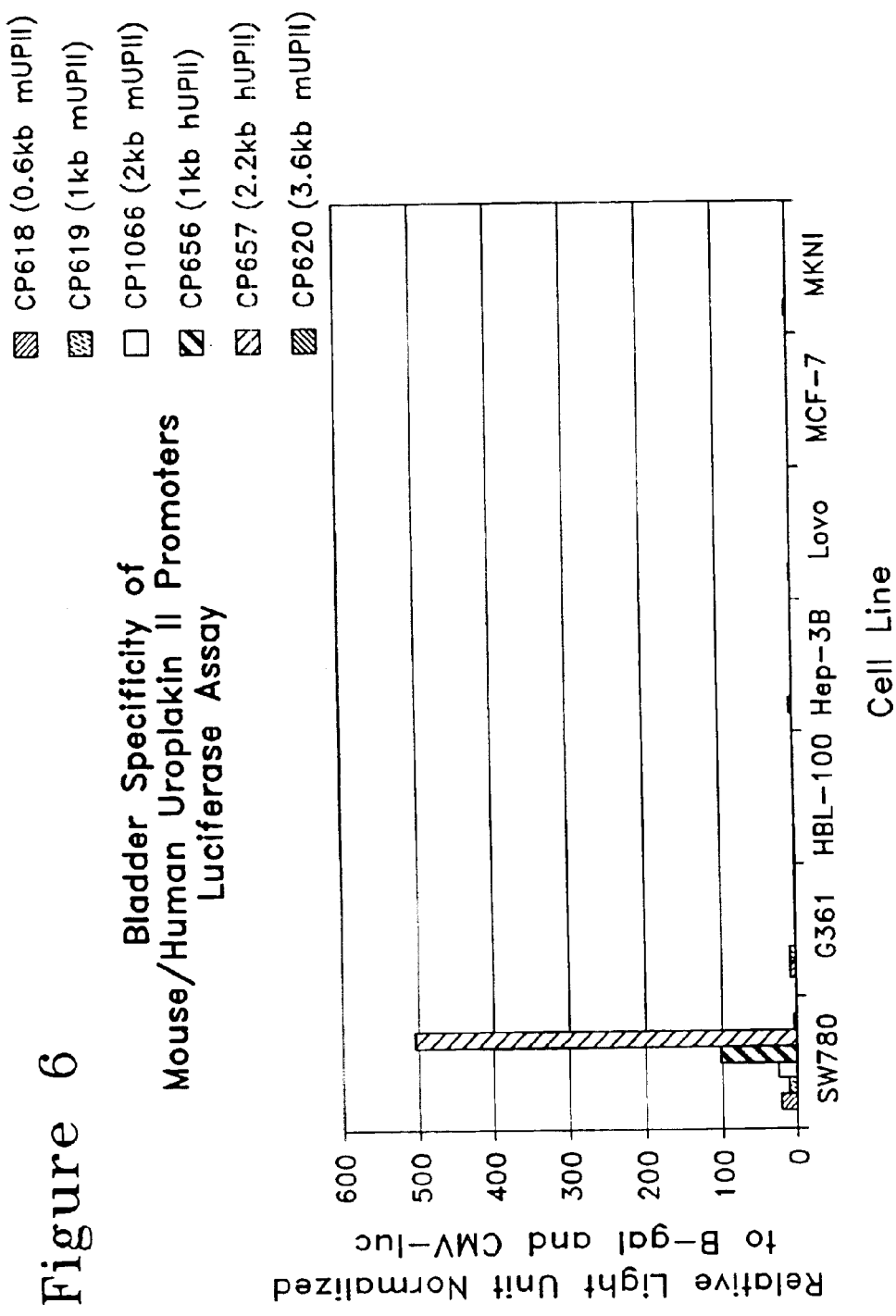
FIG. 6 is a bar graph depicting results of a luciferase assay to indicate bladder specificity of plasmids CP618 (0.6 kb mUPII, first bar); CP619 (1.0 kb mUPII, second bar); CP1010 (2 kb mUPII, third bar); CP656 (1 kb hUPII, fourth bar); CP657 (2.2 kb hUPII, fifth bar); and CP620 (3.6 mUPII, six bar) in various cell lines.

The cells were plated at $5\times10^5$ cells per 60 mm dish in complete RPMI 1640 medium and co-transfected with the various reporter constructs and pCMV-βgal (a plasmid carrying the β-galactosidase gene under the control of the CMV promoter) using a cationic lipid reagent (lipofectin). After a four hour incubation with the plasmid/lipofectin complexes, the medium was removed by aspiration and replaced with fresh RPMI 1640. The cells were incubated for a further forty eight hours at 37° C., then harvested by aspiration of the medium and lysis in 500 μl of lysate buffer (Analytical Luminescence Laboratories). A 50 μl aliquot was assayed for luciferase activity in a microtiter plate-format luminometer (Dynatech Laboratories, Model ML3000). Luciferase activities were normalized to β-gal activity, which was measured using a kit from Tropix (GALACTO-LIGHT™). The results are shown in FIGS. 5–6.

Constructs CP648 and CP649 showed no preferential expression in SW780 cells. However, CP618, CP620, CP662, CP663, CP656 and CP657 showed significant preferential expression in SW780 cells, indicating the presence of at least one urothelial cell-specific TRE in each of these constructs. CP618 and CP620 showed preferential expression in SW780 cells, while CP619 showed little expression in these cells.

Analysis of the data suggests that a minimal urothelial cell-specific promoter is contained within 600 bp of the transcriptional start site of the mUPII gene, but that the hUPII gene urothelial cell-specific promoter extends somewhat further upstream. The data also suggest a negative regulatory element is located between −600 and−1000 bp. The presence of the silencer in the mUPII 5'-flanking DNA and the high expression of CP620 further suggest the presence of a urothelial cell-specific enhancer located more than 1.0 kb from the transcriptional start site.

Example 3

Adenovirus Vectors with Urothelial Cell-specific TREs

A number of plasmid constructs were generated as intermediates for adenovirus type 5 (Ad 5) vector construct. The plasmid constructs were based on plasmid CP321 (Yu et al., 1999, *Cancer Res.* 59:4200–4203), which contains a prostate-specific enhancer inserted at a PinAI site upstream of the E1A gene and at a EagI site upstream of the E1B gene. Constructs were created by inserting various UPII-derived 5'-flanking DNA sequences into the PinAI and EagI sites and removing the prostate-specific enhancer. Characteristics of the plasmids, all of which lacked the E1A promoter and which contained the E1A enhancer, are summarized in Table 3.

TABLE 3

| Name | E1A TRE | E1B TRE |
| --- | --- | --- |
| CP656 | 1.0 kb hUPII | E1B endogenous promoter |
| CP657 | 2.4 kb hUPII | E1B endogenous promoter |
| CP569 | 3.6 mUPII | E1B endogenous promoter |
| CP622 | 0.6 kb mUPII | E1B endogenous promoter |
| CP623 | 1.0 kb mUPII | E1B endogenous promoter |
| CP662 | 0.2 kb hUPII | E1B endogenous promoter |
| CP663 | 0.6 kb hUPII | E1B endogenous promoter |
| CP664 | 0.6 kb hUPII | E1B endogenous promoter |
| CP665 | 1.0 kb hUPII | E1B endogenous promoter |
| CP666 | 0.6 kb mUPII | 0.6 kb mUPII |
| CP667 | 0.6 kb mUPII | 1.0 kb hUPII |
| CP668 | 1.0 kb mUPII | 0.6 kb mUPII |
| CP669 | 1.0 kb mUPII | 1.0 kb hUPII |
| CP670 | 0.6 kb hUPII | 0.6 kb mUPII |
| CP671 | 0.6 kb hUPII | 1.0 kb mUPII |
| CP672 | 1.0 kb hUPII | 0.6 kb mUPII |
| CP673 | 1.0 kb hUPII | 1.0 kb mUPII |
| CP1086 | 1.9 kb mUPII | Replaced by IRES |
| CP1087 | 1.0 kb hUPII | Replaced by IRES |
| CP1088 | 2.2 kb hUPII | Replaced by IRES |
| CP1089 | 1.0 kb mUPII | 1.0 kb hUPII |

Infectious recombinant adenoviral vectors was produced by co-transfecting 293 cells with the UPII 5'-flanking DNA/ E1 constructs and an Ad 5 backbone vector (pBHG10 or pBHGE3, Microbix, Inc.) as described in Yu et al. (id.). The characteristics of the viral vectors, all of which lack the E1A promoter and retain the E1A enhancer are summarized in Table 4.

TABLE 4

| Name | Vector | Ad 5 Vector | E1A TRE | E1B TRE | E3 |
| --- | --- | --- | --- | --- | --- |
| CV808 | CP569 | pBHG10 | 3.6 kb mUPII | E1B endogenous promoter | deleted |
| CV818 | CP622 | pBHG10 | 0.6 kb mUPII | E1B endogenous promoter | deleted |
| CV819 | CP622 | pBHGE3 | 0.6 kb mUPII | E1B endogenous promoter | intact |
| CV820 | CP623 | pBHG10 | 1.0 kb mUPII | E1B endogenous promoter | deleted |
| CV821 | CP623 | pBHGE3 | 1.0 kb mUPII | E1B endogenous promoter | intact |
| CV822 | CP664 | pBHG10 | 0.6 kb hUPII | E1B endogenous promoter | deleted |
| CV823 | CP664 | pBHGE3 | 0.6 kb mUPII | E1B endogenous promoter | intact |
| CV824 | CP665 | pBHG10 | 1.0 kb hUPII | E1B endogenous promoter | deleted |
| CV825 | CP665 | pBHGE3 | 1.0 kb hUPII | E1B endogenous promoter | intact |
| CV826 | CP667 | pBHG10 | 0.6 kb mUPII | 1.0 kb hUPII | deleted |
| CV827 | CP667 | pBHGE3 | 0.6 kb mUPII | 1.0 kb hUPII | intact |
| CV828 | CP669 | pBHG10 | 1.0 kb mUPII | 1.0 kb hUPII | deleted |
| CV829 | CP669 | pBHGE3 | 1.0 kb hUPII | 1.0 kb mUPII | intact |
| CV830 | CP672 | pBHG10 | 1.0 kb hUPII | 0.6 kb mUPII | deleted |

TABLE 4-continued

| Name | Vector | Ad 5 Vector | E1A TRE | E1B TRE | E3 |
|---|---|---|---|---|---|
| CV831 | CP672 | pBHGE3 | 1.0 kb hUPII | 0.6 kb mUPII | intact |
| CV832 | CP673 | pBHG10 | 1.0 kb hUPII | 1.0 kb mUPII | deleted |
| CV833 | CP673 | pBHGE3 | 1.0 kb hUPII | 1.0 kb mUPII | intact |

Figure 8:
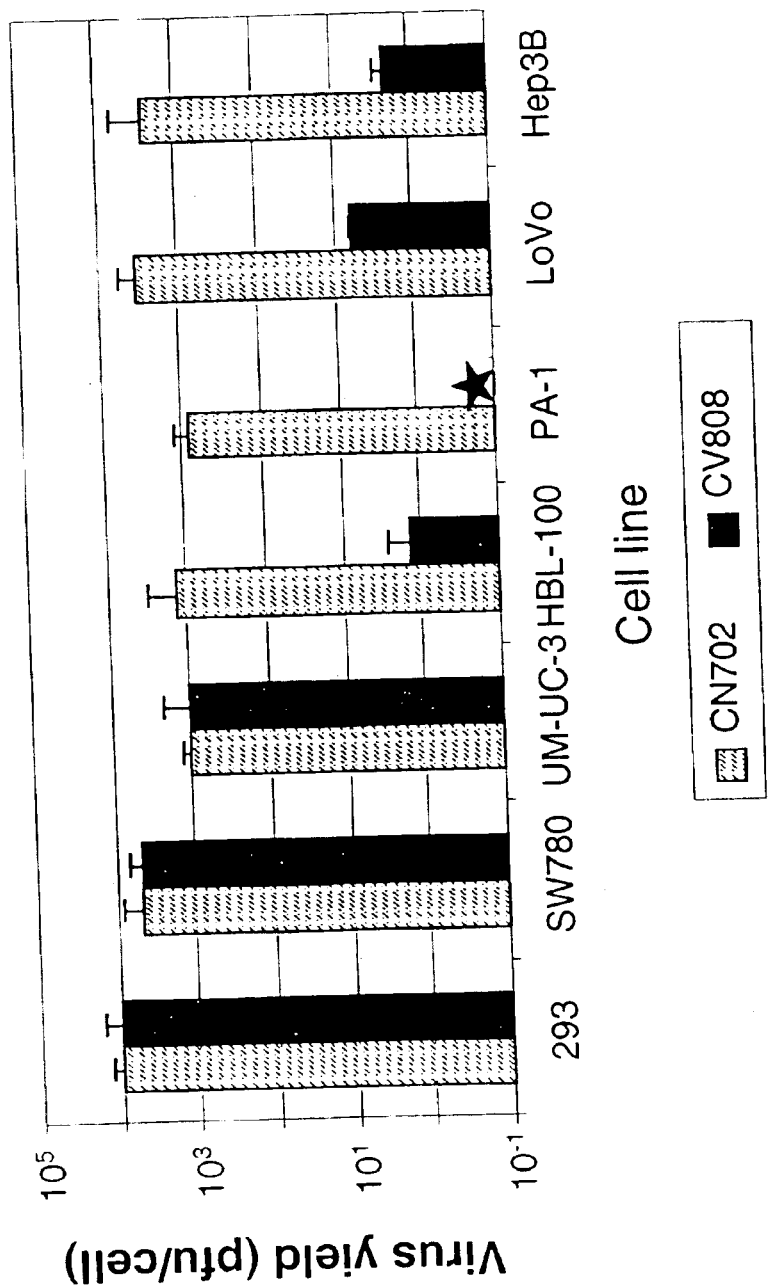
FIG. 8 is a bar graph depicting the results of a viral replication assay for viral constructs CV702 (E3-deleted adenovirus; hatched bar) and CV808 (E3-deleted adenovirus with E1A and E1B with endogenous promoter under the control of a mUPII; solid bar) in various cell lines. The star over PA-1 indicates no replication was observed.
Figure 9:
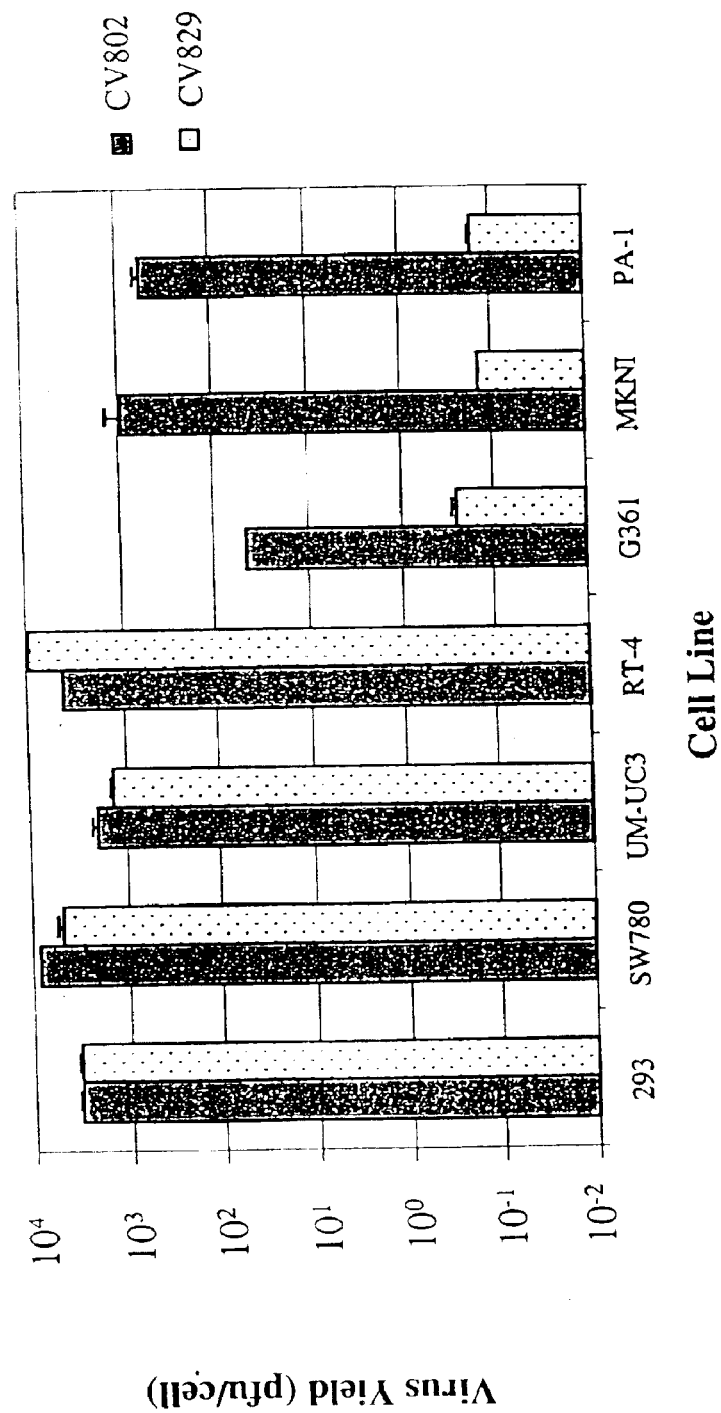
FIG. 9 is a bar graph depicting the results of a viral replication assay for viral constructs CV802 (first bar) and CV829 (second bar).

Replication specificity as indicated by virus yield assays. CV808 and CN702 (an Ad 5 variant containing a wild type E1 region and an E3 deletion identical to the E3 deletion in CV808) were tested against a panel of cell lines for viral replication (indicative of lethality) and specificity. Cell lines 293 (the producer line), SW780, UM-UC-3, HBL-100, PA-1, LoVo and Hep3B were plated at $0.5 \times 10^6$ per well in 6 well tissue culture plates, incubated for 24 hours at 37° C., then infected with CV808 or CN702 at a multiplicity of infection (MOI) of 2 plaque forming units per cell (PFU/cell) for 4 hours at 37° C. At the end of the infection period, the medium was replaced and the cells were incubated at 37° C. for a further 72 hours before harvesting for a viral yield assay as described in Yu et al. (1999) Cancer Res. 59:1498–1504. Another experiment compared CV802 and CV829. The results are shown in FIGS. 8 and 9.

CV808 and CN702 replicate equally well in bladder transitional cell carcinoma cells (SW780 and UM-UC-3), but burst size for CV808, as compared to CN702, was substantially reduced (i.e., 100 to 1000 fold) in non-bladder cell lines. The data show that CV808 preferentially replicates in bladder cells (i.e., is significantly attenuated in non-bladder tumor cells). The burst size was significantly reduced by more than 100 to 1000-fold in non-bladder carcinoma cells including LoVo, Hep3B, HBL-100 and PA-1. Further, CV829 preferentially replicates in urothelial cell lines SW780, UM-UC3, and RT-4, compared to non-urothelial cell lines G361, MKNI, and PA-1.

Figure 10:
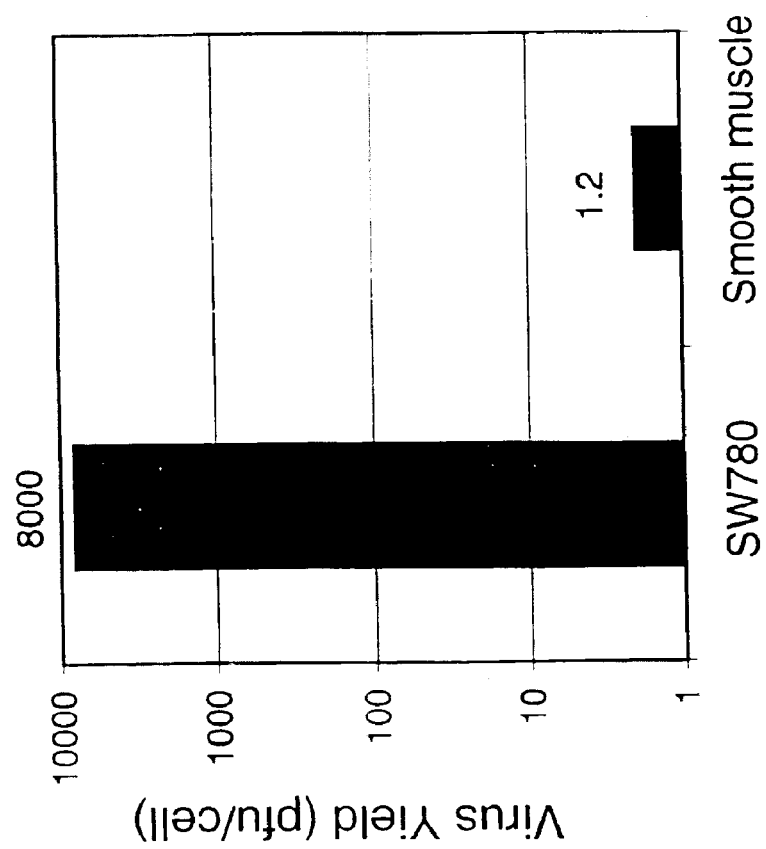
FIG. 10 is a bar graph depicting the results of a viral replication assay for viral construct CV829 in SW780 and smooth muscle cells.

Preferential replication of CV829 in SW780 cells versus smooth muscle cells. A virus yield experiment was performed as described above to compare replication of CV829 in SW780 (urothelial cells) versus bladder smooth muscle cells (Clonetics Corp.; BioWhittaker, Inc.). The results are shown in FIG. 10. CV829 (containing a compared to SW780 cells. Further, this result was confirmed in a CPE (cytotoxicity assay), which showed that CV829 lysed bladder smooth muscle cells significantly less than degree of lysis of SW780.

This is a significant result which indicates that adenovirus containing uroplakin TREs would confine replication to the target cells of interest in the bladder, namely urothelial cells, while displaying very low levels of replication in adjacent smooth muscle cells.

Example 4

Uroplakin Adenoviral Constructs Containing an IRES

A number of E3-containing viral constructs were prepared which contained uroplakin II sequences (mouse and/or human) as well as an EMCV internal ribosome entry site (IRES). The viral constructs are summarized in Table 5. All of these vectors lacked an E1A promoter and retained the E1A enhancer.

The 519 base pair EMCV IRES segment was PCR amplified from Novagen's pCITE vector by primers A/B:

primer A: 5'-GACGTCGACTAATTCCGGTT-ATTTTCCA (SEQ ID NO:21)

primer B 5'-GACGTCGACATCGTGTTTTTCAAAG-GAA (SEQ ID NO:22) (GTCGAC is a SalI site).

The EMCV IRES element was ligated to PCR blunt vector (Invitrogen pCR® blunt vector).

CP1066

The 1.9 kb-(−1885 to +1) fragment of mouse UPII from CP620 was digested with AflIII (blunted) and HindIII and inserted into pGL3-Basic from CP620 which had been digested with XhoI (blunted) and HindIII to generate CP1066.

CP1086

The 1.9 kb mouse UPII insert was digested with PinAI and ligated with CP269 (CMV driving E1A and IRES driving E1B with the deletions of E1A/E1B endogenous promoter) which was similarly cut by PinAI.

CP1087

The 1 kb (−1128 to +1) human UPII was digested with PinAI from CP665 and inserted into CP629 which had been cut by PinAI and purified (to elute CMV).

CP1088

The 2.2 kb (−2225 to +1) human UPII was amplified from CP657 with primer 127.2.1 (5'-AGGACCGGTCAC-TATAGGGCACGCGTGGT-3' (SEQ ID NO:23)) PLUS 127.2.2 (5'-AGGACCGGTGGGATGCTGGGCTGG-GAGGTGG-3' (SEQ ID NO:24)) and digested with PinAI and ligated with CP629 cut with PinAI.

CP627 is an Ad5 plasmid with an internal ribosome entry site (IRES) from encephelomycarditis virus (EMCV) at the junction of E1A and E1B. First, CP306 (Yu et al., 1999) was amplified with primer pairs 96.74.3/96.74.6 and 96.74.4/96.74.5.

The two PCR products were mixed and amplified with primer pairs 96.74.3 and 96.74.5. The resultant PCR product contains a 100 bp deletion in E1A-E1B intergenic region and a new SalI site at the junction. EMCV IRES fragment was amplified from pCITE-3a(+) (Novagen) using primers 96.74.1 and 96.74.2. The SalI fragment containing IRES was placed into SalI site to generate CP627 with the bicistronic E1A-IRES-E1B cassette. CP629 is a plasmid with CMV promoter amplified from pCMVbeta (Clontech) with primer 99.120.1 and 99.120.2 and cloned into PinAI site of CP627.

CP657 is a plasmid with 2.2 kb 5' flanking region of human UPII gene in pGL3-Basic (Promega). The 2.2 kb hUPII was amplified by PCR from GenomeWalker product with primer 100.113.1 and 100.113.2 and TA-cloned into pGEM-T to generate CP655.

The 2.2 kb insert digested from SacII (blunt-ended) and KpnI was cloned into pGL3-Basic at HindIII (blunted) and KpnI to create CP657.

CP1089

The 1 kb (−965 to +1) mouse UPII was digested by PinAI from CP263 and inserted into CN422 (PSE driving E1A and GKE driving E1B with the deletions of E1A/E1B endogenous promoter) cut by PinAI and purified and further digested with EagI and ligated with 1 kb (−1128 to +1) human UPII cut from CP669 with EagI.

CP1129

The 1.8 kb hUPII fragment with PinAI site was amplified from CP657 with primer 127.50.1 and 127.2.2 and cloned into PinAI site of CP629.

CP1131

CP686 was constructed by replacing the CMV promoter in CP629 with an AFP fragment from CP219. A 1.4 kb DNA fragment was released from CP686 by digesting it with BssHII, filling with Klenow, then digesting with BglII. This DNA fragment was then cloned into a similarly cut CP686 to generate CP1199. In CP1199, most of the E1B 19-KDa region was deleted. The 1.8 kb hUPII fragment with PinAI site was amplified from CP657 by PCR with primer 127.50.1 and 127.2.2 and inserted into similarly digested CP1199 to create CP1131.

The plasmids above were all co-transfected with pBHGE3 to generate CV874 (from CP1086), CV875 (from CP1087), CV876 (from 1088) and CV877 (from CP1089), CV882 (from CP1129) and CV884 (from CP1131). CP1088, CP1129 and CP1131 were cotransfected with pBHGE3 for construction of CV876, CV892 and CV884, respectively by lipofectAMINE (Gibco/BRL) for 11–14 days. pBHGE3 was purchased from Microbix, Inc., and was described previously. The cells were lysed by three freeze-thaw cycles and plaqued on 293 cells for a week. The single plaques were picked and amplified by infection in 293 cells for 3–5 days. The viral DNAs were isolated from the lysates and the constructs were confirmed by PCR with primer 31.166.1/ 51.176 for CV876 and primer 127.50.1/51.176 for CV882 and CV884 at E1 region and primer 32.32.1/2 for all three viruses at E3 region.

TABLE 5

| Name | Ad 5 Vector | Vector | E1A TRE | E1B TRE | E3 |
|---|---|---|---|---|---|
| CV874 | CP1086 | pBHGE3 | 1.9 kb mUPII | IRES | intact |
| CV875 | CP1087 | pBHGE3 | 1.0 kb hUPII | IRES | intact |
| CV876 | CP1088 | pBHGB3 | 2.2 kb hUPII | IRES | intact |
| CV877 | CP1089 | pBHGE3 | 1.0 kb mUPII | 1.0 kb hUPII (E1B promoter deleted) | intact |
| CV882 | CP1129 | pBHGE3 | 1.8 kb hUPII | IRES | intact |
| CV884 | CP1131 | pBHGE3 | 1.8 kb hUPii | IRES (E1B 19-kDa deleted) | intact |

Viruses are tested and characterized as described above.

| | | |
|---|---|---|
| 96.74.1 | GACGTCGACATCGTGTTTTTCAAAGGAA | (SEQ ID NO:22) |
| 96.74.2 | GACGTCGACTAATTCCGGTTATTTTCCA | (SEQ ID NO:21) |
| 96.74.3 | CCTGAGACGCCCGACATCACCTGTG | (SEQ ID NO:25) |
| 96.74.4 | TGCTGAATGGTCGACATGGAGGCTTGGGAG | (SEQ ID NO:26) |
| 96.74.5 | CACAACCGCTCTCCACAGATGCATG | (SEQ ID NO:27) |
| 96.74.6 | GTCGACCATTCAGCAAACAAAGGCGTTAAC | (SEQ ID NO:28) |
| 100.113.1 | AGGGGTACCCACTATAGGGCACGCGTGGT | (SEQ ID NO:13) |
| 100.113.2 | ACCCAAGCTTGGGATGCTGGGCTGGGAGGTGG | (SEQ ID NO:14) |
| 127.2.2 | AGGACCGGTGGATGCTGGGCTGGGAGGTGG | (SEQ ID NO:24) |
| 127.50.1 | AGGACCGGTCAGGCTTCACCCCAGACCCAC | (SEQ ID NO:29) |
| 31.166.1 | TGCGCCGGTGTACACAGGAAGTGA | (SEQ ID NO:30) |
| 32.32.1 | GAGTTTGTGCCATCGGTCTAC | (SEQ ID NO:31) |
| 32.32.2 | AATCAATCCTTAGTCCTCCTG | (SEQ ID NO:32) |
| 51.176 | GCAGAAAAATCTTCCAAACACTCCC | (SEQ ID NO:33) |
| 99.120.1 | ACGTACACCGGTCGTTACATAACTTAC | (SEQ ID NO:34) |
| 99.120.2 | CTAGCAACCGGTCGGTTCACTAAACG | (SEQ ID NO:35) |

Example 5

In vitro and In vivo Assays of Anti-tumor Activity

An especially useful objective in the development of urothelial cell-specific adenoviral vectors is to treat patients with bladder cancer. An initial indicator of the feasibility is to test the vector(s) for cytotoxic activity against cell lines and tumor xenografts grown subcutaneously in Balb/c nu/nu mice.

In vitro Characterization of CV876

Virus yield Assay for CV876

$5 \times 10^5$ 293, RT-4, SW780, PA-1, G361, MKNI, HBL-100, Fibroblast (from lung) and Smooth muscle cells (from bladder) were plated into each well of six-well plates. Twenty-four hours later, medium was aspirated and replaced with 1 ml of serum-free RPMI 1640 containing CV802 (wt.Ad5 with E3) or CV876 at a MOI of 2 pfu/cell. After a 4-h incubation at 37° C., cells were washed with prewarmed PBS, and 2 ml of complete RPMI 1640 were added to each well. After an additional 72 h at 37° C., the cells were scraped into medium and lysed by three freeze-thaw cycles. The lysates were tested for virus production by triplicate plaque assay for 8–10 days under semisolid agarose on 293 cells.

Unlike wt. Ad5, CV802 which grows well in all of the cells tested, CV876 replicates much better in permissive cells (293, RT-4 and SW780) than in non-permissive cells (PA-1, G361, MKN1, HBL-100 and primary cells) by about 100–10000 fold. Noticeably, the replication in SW780 for CV876 is about 100 fold less than CV802, which indicates the limitation of this virus in efficacy.

Growth Curve Experiment for CV876

$5 \times 10^5$ RT-4, PA-1, Smooth muscle and Fibroblast cells were plated into each well of six-well plates. Twenty-four hours later, medium was aspirated and replaced with 1 ml of serum-free RPMI 1640 containing CV802 (wt.Ad5 with 133) or CV876 at a MOI of 2 pfu/cell. After a 4-h incubation at 37° C., cells were washed with prewarmed PBS, and 2 ml of complete RPMI 1640 were added to each well. At different time points of 0, 12, 24, 36, 48, 72, 96 and 120 h, the cells were scraped into medium and lysed by three freeze-thaw cycles. The lysates were tested for virus production by triplicate plaque assay for 8–10 days under semisolid agarose on 293 cells.

Very similar as in virus yield assay, CV876 replicates well only in RT-4 but not in primary cells and PA-1 over a 120 h period of time. However, CV876 does show a delay of replication in RT-4 compared to CV802.

Cytopathic Effect Assay for CV876

$5 \times 10^5$ 293, RT-4, SW780, PA-1, MKN1 and LNCap were plated into each well of six-well plates. Twenty-four hours later, medium was aspirated and replaced with 1 ml of serum-free RPMI 1640 containing CV802 (wt.Ad5 with E3) or CV876 at increasing MOI from 0.001 to 10 (the data shown was at MOI 1). After a 4-h incubation at 37° C., medium was replaced with 3 ml of complete RPMI 1640 and incubated at 37° C. for 6–8 days when cytopathic effect was observed for CV802 at MOI 0.01.

CV802 shows efficacy in all the cells tested while CV876 only kills the permissive cells (293, RT-4 and SW780) but not the non-permissive cells (PA-1, MKN-1 and LNCap).

MTT Assay for CV876

$2 \times 10^4$ 293, RT-4, SW780, MKN1, PA-1, HBL-100, Smooth muscle cells (from bladder) and Fibroblast (from lung) were plated into each well of 96-well plates. Twenty-four hours later, the cells were infected with CV802 and CV876 at increasing MOI from 0.001 to 10 in complete RPMI 1640. A rapid colorimetric assay for cell growth and survival was run at different time point of day 1, 3, 5, 7 and 10. The medium was replaced by 50 ul of MTT at 1 mg/ml solution, which is converted to an insoluble purple formazan by dehydrogenase enzymes present in active mitochondria of live cells. After 3–4 h incubation at 37° C., the solution was replaced by isopropanol and the plates were incubated at 30° C. for 1 h and read at 560 nm test wavelength and 690 nm reference wavelength.

Similar as the results in CPE assay, CV876 shows efficacy only in permissive cells but not in non-permissive cells. Again, in RT-4 and SW780, CV876 kills the cells much slower than CV802.

In vitro Characterization of CV882

Virus Yield Assay for CV882

$5 \times 10^5$ 293, RT-4, SW780, G361, LNCap, HBL-100, MKN1, PA-1, Fibroblast and Smooth muscle cells were plated into each well of six-well plates. Twenty-four hours later, medium was aspirated and replaced with 1 ml of serum-free RPMI 1640 containing CV802 (wt.Ad5 with E3) or CV882 at a MOI of 2 pfu/cell. After a 4-h incubation at 37° C., cells were washed with prewarmed PBS, and 2 ml of complete RPMI 1640 were added to each well. After an additional 72 h at 37° C., the cells were scraped into medium and lysed by three freeze-thaw cycles. The lysates were tested for virus production by triplicate plaque assay for 8–10 days under semisolid agarose on 293 cells.

The replication of CV882 in permissive cells (293, RT-4 and SW780) is comparable to CV802 (the difference is less than 100 fold) while it shows over 1000–1000000 fold difference in non-permissive cells (G361, LNCap, HBL-100, MKN1, PA-1 and primary cells).

Growth Curve Experiment for CV882

$5 \times 10^5$ RT-4, PA-1, and Fibroblast cells were plated into each well of six-well plates. Twenty-four hours later, medium was aspirated and replaced with 1 ml of serum-free RPMI 1640 containing CV802 (wt.Ad5 with E3) or CV882 at a MOI of 2 pfu/cell. After a 4 h incubation at 37° C., cells were washed with prewarmed PBS, and 2 ml of complete RPMI 1640 were added to each well. At different time points of 0, 12, 24, 36, 48, 72, 96 and 120 h, the cells were scraped into medium and lysed by three freeze-thaw cycles. The lysates were tested for virus production by triplicate plaque assay for 8–10 days under semisolid agarose on 293 cells.

Very similar as in virus yield assay, CV882 replicates well only in RT-4 but not in primary cells and PA-1 over a 120 h period of time. Additionally, CV882 shows better replication in RT-4 compared to CV876.

Cytopathic Effect Assay for CV882

$5 \times 10^5$ 293, RT-4, SW780, HBL-100, G361, PA-1 and Fibroblast cells were plated into each well of six-well plates. Twenty-four hours later, medium was aspirated and replaced with 1 ml of serum-free RPNI 1640 containing CV802 (wt.Ad5 with E3) or CV882 at increasing MOI from 0.001 to 10 (the data shown was at MOI 1). After a 4 h incubation at 37° C., medium was replaced with 3 ml of complete RPMI 1640 and incubated at 37° C. for 6–8 days when cytopathic effect was observed for CV802 at MOI 0.01.

CV802 shows efficacy in all the cells tested while CV882 only kills the permissive cells (293, RT-4 and SW780) but not the non-permissive cells (HBL-100, G361, PA-1 and Fibroblast cells).

MTT Assay for CV882

$2 \times 10^4$ RT-4, SW780, PA-1, HBL-100, U118 and Fibroblast were plated into each well of 96-well plates. Twenty-four hours later, the cells were infected with CV802 and CV882 at increasing MOI from 0.001 to 10 in complete RPMI 1640. A rapid colorimetric assay for cell growth and survival was run at different time points of day 1, 3, 5, 7 and 10. The medium was replaced by 50 ul of MTT at 1 mg/ml solution, which is converted to an insoluble purple formazan by dehydrogenase enzymes present in active mitochondria of live cells. After 3–4 h incubation at 37° C., the solution was replaced by isopropanol and the plates were incubated at 30° C. for 1 h and read at 560 nm test wavelength and 690 nm reference wavelength.

Similar as the results in CPE assay, CV882 shows efficacy only in permissive cells but not in non-permissive cells.

In Vitro Characterization of CV884

Virus Yield Assay for CV884

$5 \times 10^5$ 293, RT-4, SW780, G361, LNCap, HBL-100, MKN1, PA-1, Fibroblast and Smooth muscle cells were plated into each well of six-well plates. Twenty-four hours later, medium was aspirated and replaced with 1 ml of serum-free RPMI 1640 containing CV802 (wt.Ad5 with E3) or CV984 at a MOI of 2 pfu/cell. After a 4-h incubation at 37° C., cells were washed with prewarmed PBS, and 2 ml of complete RPMI 1640 were added to each well. After an additional 72 h at 37° C., the cells were scraped into medium and lysed by three freeze-thaw cycles. The lysates were tested for virus production by triplicate plaque assay for 8–10 days under semisolid agarose on 293 cells.

The replication of CV884 is very similar as CV802 in permissive cells (293, RT-4 and SW780) but shows over 1000 fold difference with CV802 in non-permissive cells (G361, LNCap, HBL-100, MKN1, PA-1 and primary cells). CV884 shows better efficacy than CV876 and CV882 without losing much specificity.

Growth Curve Experiment for CV884

$5 \times 10^5$ RT-4, PA-1, Smooth muscle and Fibroblast cells were plated into each well of six-well plates. Twenty-four hours later, medium was aspirated and replaced with 1 ml of serum-free RPMI 1640 containing CV802 (wt.Ad5 with E3) or CV884 at a MOI of 2 pfu/cell. After a 4-h incubation at 37° C., cells were washed with prewarmed PBS, and 2 ml of complete RPMI 1640 were added to each well. At different time points of 0, 12, 24, 36, 48, 72, 96 and 120 h, the cells were scraped into medium and lysed by three freeze-thaw cycles. The lysates were tested for virus production by triplicate plaque assay for 8–10 days under semisolid agarose on 293 cells.

Very similar as in virus yield assay, CV884 replicates very well only in RT-4 (similar as CV802) but not in primary cells and PA-1. Again, the replication of CV884 is better than CV882 and CV876.

Cytopathic Effect Assay for CV884

$5 \times 10^5$ 293, RT-4, SW780, G361, PA-1 and Fibroblast cells were plated into each well of six-well plates. Twenty-four hours later, medium was aspirated and replaced with 1 ml of serum-free RPMI 1640 containing CV802 (wt.Ad5 with E3) or CV884 at increasing MOI from 0.001 to 10 (the data shown was at MOI 1). After a 4-h incubation at 37° C., medium was replaced with 3 ml of complete RPMI 1640 and incubated at 37° C. for 6–8 days when cytopathic effect was observed for CV802 at MOI 0.01.

CV802 shows efficacy in all the cells tested while CV884 only kills the permissive cells (293, RT-4 and SW780) but not the non-permissive cells (G361, PA-I and Fibroblast cells).

MTT Assay for CV884

$2 \times 10^4$ 293, RT-4, SW780, U118, Fibroblast and Smooth muscle cells were plated into each well of 96-well plates. Twenty-four hours later, the cells were infected with CV802 and CV884 at increasing MOI from 0.001 to 10 in complete RPMI 1640. A rapid calorimetric assay for cell growth and survival was run at different time points of day 1, 3, 5, 7 and 10. The medium was replaced by 50 ul of MTT at 1 mg/ml solution which is converted to an insoluble purple formazan by dehydrogenase enzymes present in active mitochondria of live cells. After 3–4 h incubation at 37° C., the solution was replaced by isopropanol and the plates were incubated at 30° C. for 1 h and read at 560 nm test wavelength and 690 nm reference wavelength.

Similar as the results in CPE assay, CV884 shows strong efficacy (similar as wt. Ad5) only in permissive cells but not in non-permissive cells.

In vivo Activity of CV808

Mice were given subcutaneous (SC) injections of $1 \times 10^6$ sW780 cells. When tumors grew to about 500 mm³, CV808 was introduced into the mice ($5 \times 10^7$ PFU of virus in 0.1 ml PBS and 10% glycerol) intratumorally. Control mice received vehicle alone. Tumor sizes were measured weekly.

Figure 11:
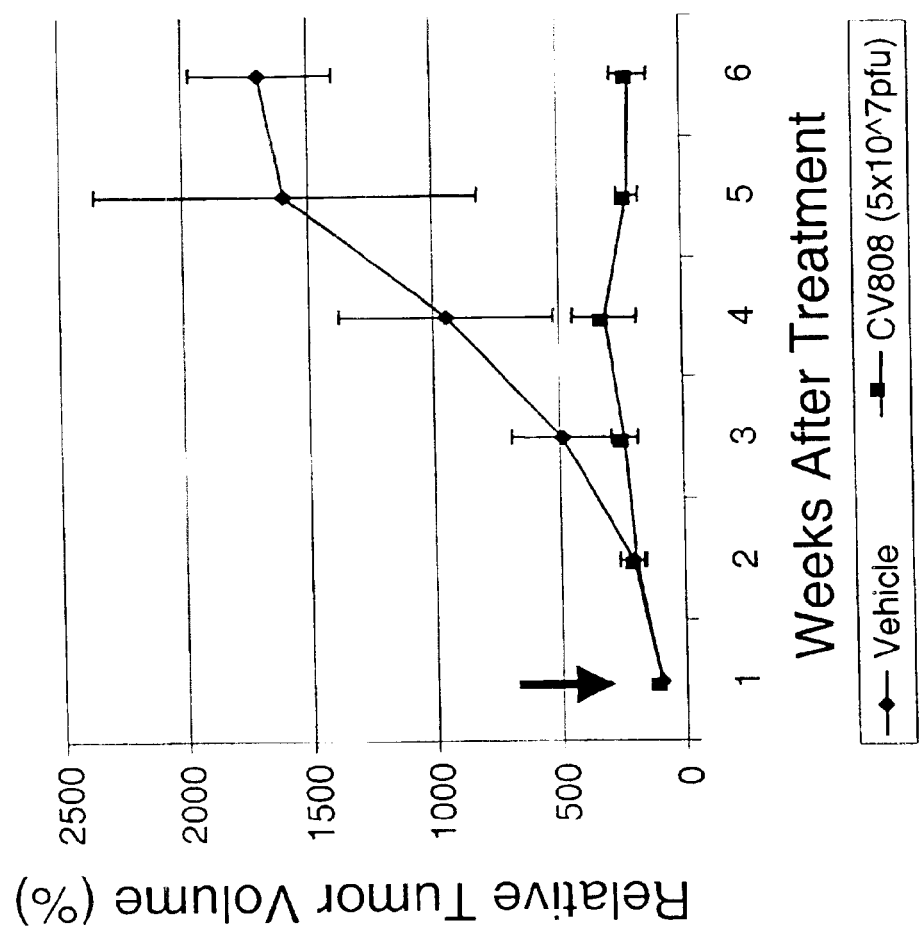
FIG. 11 is a graph depicting change in tumor volume of bladder xenografts in nude mice treated with CV808 (solid boxes) versus vehicle alone (no virus; solid diamonds).

The results are shown in FIG. 11. The data indicate that CV808 was effective at suppressing tumor growth.

While it is highly possible that a therapeutic based on the viruses described here would be given intralesionally (i.e., direct injection), it would also be desirable to determine if intravenous (IV) administration of adenovirus vector can affect tumor growth. If so, then it is conceivable that the virus could be used to treat metastatic tumor deposits inaccessible to direct injection. For this experiment, groups of mice bearing bladder epithelial tumors are inoculated with $10^8$ to $10^{10}$ PFU of an adenoviral vector by tail vein injection, or with buffer used to carry the virus as a negative control. The effect of IV injection of the adenoviral vector on tumor size is compared to vehicle treatment.

Example 6

Adenoviral Vectors with Adenovirus Death Protein (ADP) Under the Control of a Urothelial-cell Specific TRE An adenovirus in which the ADP gene is under control of a urothelial cell-specific TRE can be constructed as described below. ADP is encoded within the E3 region and naturally under control of the major late promoter (MLP). The gene appears to code for a protein (ADP) that is important in expediting host cell lysis. Tollefson et al. (1996) *J. Virol.* 70(4):2296; Tollefson et al. (1992) *J. Virol.* 66(6):3633. Thus, adenoviral vectors containing the ADP gene may render the adenoviral vector more potent, making possible more effective treatment and/or a lower dosage requirement.

The ADP coding sequence from Ad2 can introduced into Ad5 in the E3 region (which is often deleted in the constructs; see Example 1), as follows.

An ADP cassette is constructed using overlap PCR. The Y leader, an important sequence for correct expression of some late genes, is PCR amplified using primers:

5' GCCTTAATTAAAAGCAAACCTCACCTCCG . . . Ad2 28287bp (37.124.1) (SEQ ID NO:36); and 5' GTGGAACAAAAGGTGATTAAAAAATCCCAG . . . Ad2 28622bp (37.146.1) (SEQ ID NO:37).

The ADP coding region is PCR amplified using primers

5' CACCTTTTGTTCCACCGCTCTGCTTATTAC . . . Ad2 29195bp (37.124.3) (SEQ ID NO:38) and 5' GGCTTAATTAACTGTGAAAGGTGGGAGC . . . Ad2 29872bp (37.124.4) (SEQ ID NO:39).

The two fragments were annealed and the overlap product was PCR amplified using primers 37.124.1 and 37.124.4. The ends of the product were polished with Klenow fragment and ligated to BamHI cut pGEM-72(+) (Promega, Madison, Wis.) to produce CN241. The ADP cassette was excised by digesting CN241 with PacI restriction endonuclease and ligated with two vectors, CN247 and CN248, generating plasmids CN252 and CN270, respectively.

CN247 contains a unique Pacd site in the E3 region and was constructed as follows. A plasmid containing the full length Ad5 genome, TG3602 (Transgene, France), was digested with BamHI and relegated to yield CN221. The backbone of this plasmid (outside of the Ad5 sequence) contained a Pacd site that needed to be removed to enable further manipulations. This was effected by digesting CN221 with Pacd and polishing the ends with T4 DNA polymerase, resulting in CN246. CN246 was digested with AscI and AvrII (to remove intact E3 region). This fragment was replaced by a similarly cut fragment derived from BHG11. The resulting plasmid, CN247, lacks the E3 region and has a PacI site suitable for insertion of the ADP cassette fragment (described above). Ligation of CN247 with the ADP cassette generated CN252.

CN248 (a construct that would allow introduction of an ADP cassette into a Ad that also contains a deletion/substitution in the E4 region) was made, as follows. The E4 region was deleted by digesting CN108, a construct that contains right hand end Ad5 sequence from the unique EcoRI site in the E3 region, with AvrII and AflIII. The only E4 ORF necessary for viral replication, ORF 6, was reintroduced by PCR amplifying the ORF with primers, 33.81.1 (Ad5 33096):
GCAGCTCACTTAAGTTCATGTCG (SEQ ID NO:40)
33.81.2(Ad5 34084):
TCAGCCTAGGAAATATGACTACGTCCG (SEQ ID NO:41)

The resulting plasmid is CN203. CN203 was digested with EcoRI and ligated to CN209, a shuttle plasmid, to generate CN208. In the final cloning step, CN208 was digested with AscI and AvrII and ligated to similarly cut E4 deletion/substitution with the ADP cassette.

Thus, both CN252 and CN270 are adenoviral derivatives containing the ADP and lacking the E3 gene. In addition, CN270 lacks some sequence in the E4 region as previously described. Full-length adenoviral vectors are obtained via in vitro ligation of (1) appropriately prepared viral DNA digested with BamHI and (2) CN252 or CN257 also digested with BamHI. The ligation product is used to transfect 293 cells. Plaque assays are performed as described above.

CN252 and CN270 can also be modified by insertion of a UP-TRE fragment to place the ADP gene under control of UP-TRE.

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

TABLE 6

IRES SEQUENCES

A 519 base pair IRES obtainable from encephelomycarditis virus (EMCV) (SEQ ID NO:42).

```
  1 GACGTCGACTAATTCCGGTTATTTTCCACCATATTGCCGTCTTTTGGCAA
       SalI
 51 TGTGAGGGCCCGGAAACCTGGCCCTGTCTTCTTGACGAGCATTCCTAGGG

101 GTCTTTCCCCTCTCGCCAAAGGAATGCAAGGTCTGTTGAATGTCGTGAAG

151 GAAGCAGTTCCTCTGGAAGCTTCTTGAAGACAAACAACGTCTGTAGCGAC

201 CCTTTGCAGGCAGCGGAACCCCCCACCTGGCGACAGGTGCCTCTGCGGCC

251 AAAAGCCACGTGTATAAGATACACCTGCAAAGGCGGCACAACCCCAGTGC

301 CACGTTGTGAGTTGGATAGTTGTGGAAAGAGTCAAATGGCTCTCCTCAAG

351 CGTATTCAACAAGGGGCTGAAGGATGCCCAGAAGGTACCCCATTGTATGG

401 GATCTGATCTGGGGCCTCGGTGCACATGCTTTACATGTGTTTAGTCGAGG

451 TTAAAAAACGTCTAGGCCCCCCGAACCACGGGGACGTGGTTTTCCTTTGA
           SalI

501 AAAACACGATGTCGACGTC
```

An IRES obtainable from vascular endothelial growth factor (VEGF) (SEQ ID NO:43).

```
  1 ACGTAGTCGACAGCGCAGAGGCTTGGGGCAGCCGAGCGGCAGCCAGGCCC
          SalI

51 CGGCCCGGGCCTCGGTTCCAGAAGGGAGAGGAGCCCGCCAAGGCGCGCAA

101 GAGAGCGGGCTGCCTCGCAGTCCGAGCCGGAGAGGGAGCGCGAGCCGCGC

151 CGGCCCCGGACGGCCTCCGAAACCATGGTCGACACGTA
                                SalI
```

A 5'UTR region of HCV (SEQ ID NO:44).

```
  1 GCCAGCCCCTGATGGGGCGACACTCCGCCATGAATCACTCCCCTGTGAGGAACTACTG

61 TCTTCACGCAGAAAGCGTCTAGCCATGGCGTTAGTATGAGTGTCGTGCAGCCTCCAGGAC

121 CCCCCCTCCCGGGAGAGCCATAGTGGTCTGCGGAACCGGTGAGTACACCGGAATTGCCAG

181 GACGACCGGGTCCTTTCTTGGATTAACCCGCTCAATGCCTGGAGATTTGGGCGTGCCCCC
```

TABLE 6-continued

IRES SEQUENCES

```
241 GCAAGACTGCTAGCCGAGTAGTGTTGGGTCGCGAAAGGCCTTGTGGTACTGCCTGATAGG

301 GTGCTTGCGAGTGCCCCGGGAGGTCTCGTAGACCGTGCACC (341)
```

A 5'UTR region of BiP (SEQ ID NO:45)

```
  1 CCCGGGGTCACTCCTGCTGGACCTACTCCGACCCCCTAGGCCGGGAGTGAAGGCGGGACT

61 TGTGCGGTTACCAGCGGAAATGCCTCGGGGTCAGAAGTCGCAGGAGAGATAGACAGCTGC

121 TGAACCAATGGGACCAGCGGATGGGGCGGATGTTATCTACCATTGGTGAACGTTAGAAAC

181 GAATAGCAGCCAATGAATCAGCTGGGGGGCGGAGCAGTGACGTTTATTGCGGAGGGGGC

241 CGCTTCGAATCGGCGGCGGCCAGCTTGGTGGCCTGGGCCAATGAACGGCCTCCAACGAGC

301 AGGGCCTTCACCAATCGGCGGCCTCCACGACGGGGCTGGGGGAGGGTATATAAGCCGAGT

361 AGGCGACGGTGAGGTCGACGCCGGCCAAGACAGCACAGACAGATTGACCTATTGGGGTGT

421 TTCGCGAGTGTGAGAGGGAAGCGCCGCGGCCTGTATTTCTAGACCTGCCCTTCGCCTGGT

481 TCGTGGCGCCTTGTGACCCCGGGCCCTGCCGCCTGCAAGTCGAAATTGCGCTGTGCTCC

541 TGTGCTACGGCCTGTGGCTGGACTGCCTGCTGCTGCCCAACTGGCTGGCAAGATG (595)
```

A 5'UTR of PDGF (SEQ ID NO:46).

```
  1 GTTTGCACCTCTCCCTGCCCGGGTGCTCGAGCTGCCGTTGCAAAGCCAACTTTGGAAAAA

61 GTTTTTTGGGGGAGACTTGGGCCTTGAGGTGCCCAGCTCCGCGCTTTCCGATTTTGGGGG

121 CTTTCCAGAAAATGTTGCAAAAAAGCTAAGCCGGCGGGCAGAGGAAAACGCCTGTAGCCG

181 GCGAGTGAAGACGAACCATCGACTGCCGTGTTCCTTTTCCTCTTGGAGGTTGGAGTCCCC

241 TGGGCGCCCCCACACCCCTAGACGCCTCGGCTGGTTCGCGACGCAGCCCCCGGCCGTGG

301 ATGCTGCACTCGGGCTCGGGATCCGCCCAGGTAGCCGGCCTCGGACCCAGGTCCTGCGCC

361 CAGGTCCTCCCCTGCCCCCAGCGACGGAGCCGGGGCCGGGGCGGCGGCGCCGGGGGCA

421 TGCGGGTGAGCCGCGGCTGCAGAGGCCTGAGCGCCTGATCGCCGCGGACCTGAGCCGAGC

481 CCACCCCCCTCCCCAGCCCCCCACCCTGGCCGCGGGGCGGCGCGCTCGATCTACGCGTC

541 CGGGGCCCCGCGGGGCCGGGCCCGGAGTCGGCATG (575)
```

TABLE 7

LITERATURE REFERENCES FOR IRES

| IRES Host | Example | Reference |
|---|---|---|
| Picornavirus | HAV | Glass et al., 1993. Virol 193:842–852 |
| | EMCV | Jang & Winimer, 1990. Gene Dev 4:1560–1572 |
| | Poliovirus | Borman et al., 1994. EMBO J 13:3149–3157 |
| HCV and pestivirus | HCV | Tsukiyama-Kohara et al., 1992. J Virol 66:1476–1483 |
| | BVDV | Frolov I et al., 1998. RINA. 4:1418–1435 |
| Leishmania virus | LRV-1 | Maga et al., 1995. Mol Cell Biol 15:4884–4889 |
| Retroviruses | MoMLV VL3O (Harvey murine sarcoma virus) | Torrent et al., 1996. Hum Gene Ther 7:603–612 |
| | REV | Lopez-Lastra et al., 1997. Hum Gene Ther 8:1855–1865 |
| Eukaryotic mRNA | BiP | Macejak & Sarnow, 1991. Nature 353:90–94 |
| | antennapedia mRNA | Oh et al., 1992. Gene & Dev 6:1643–1653 |
| | FGF-2 | Vagner et al., 1995. Mol Cell Biol 15:35–44 |
| | PDGF-B | Bernstein et al., 1997. J Biol Chem 272:9356–9362 |
| | IGFII | Teerink et al., 1995. Biochim Biophys Acta 1264:403–408 |
| | eIF4G | Gan & Rhoads, 1996. J Biol Chem 271:623–626 Stein et al., 1998. Mol Cell Biol 18:3112–3119; |
| | VEGF | Huez et al., 1998. Mol Cell Biol 18:6178–6190 |

What is claimed is:

1. An isolated human uroplakin II (UPII) transcriptional regulatory element (TRE) comprising nucleotides 2028 to 2239 of SEQ ID NO:1, wherein said TRE exhibits urothelial cell-specific activity.

2. The UPII TRE of claim 1, comprising nucleotides 1647 to 2239 of SEQ ID NO:1.

3. The UPII TRE of claim 1, comprising nucleotides 1223 to 2239 of SEQ ID NO:1.

4. The UPII TRE of claim 1, comprising nucleotides 1 to 2239 of SEQ ID NO:1.

5. The UPII TRE of claim 1 comprising nucleotides 430 to 2239 of SEQ ID NO:1.

6. An adenovirus vector comprising an adenoviral gene essential for replication under transcriptional control of a uroplakin II (UPII) transcriptional response element (TRE) comprising a nucleotide sequence selected from the group consisting of nucleotides 2028 to 2239 of SEQ ID NO:1; nucleotides 1647 to 2239 of SEQ ID NO:1; nucleotides 1223 to 2239 of SEQ ID NO:1; nucleotides 1 to 2239 of SEQ ID NO:1; nucleotides 430 to 2239 of SEQ ID NO:1; nucleotides 2023–2239 of SEQ ID NO:1; nucleotides 3005 to 3592 of SEQ ID NO:2; and 2627 to 3592 of SEQ ID NO:2.

7. An adenovirus vector according to claim 6, wherein the adenoviral gene essential for replication is an adenoviral early gene.

8. An adenovirus vector according to claim 7, wherein the adenoviral early gene is E1A.

9. An adenovirus vector according to claim 7, wherein the adenoviral early gene is E1B.

10. The adenovirus vector of claim 9, wherein E1B has a deletion of the 19-kDa region.

11. An adenovirus vector according to claim 6, wherein the adenoviral gene essential for replication is an adenoviral late gene.

12. An adenovirus vector according to claim 6, wherein the uroplakin gene TRE is obtained from a mouse uroplakin II gene.

13. An adenovirus vector according to claim 12, wherein the TRE comprises nucleotides 3005–3592 of SEQ ID NO:2.

14. An adenovirus vector according to claim 6, wherein said TRE comprises nucleotides 2627–3592 of SEQ ID NO:2.

15. An adenovirus vector according to claim 6, wherein the uroplakin II TRE is obtained from a human uroplakin II gene.

16. An adenovirus vector according to claim 6, wherein said TRE comprises nucleotides 1–2239 of SEQ ID NO:1.

17. An adenovirus vector according to claim 6, wherein said TRE comprises nucleotides 2023–2239 of SEQ ID NO:1.

18. An adenovirus vector according to claim 6, wherein said TRE comprises nucleotides 430–2239 of SEQ ID NO:1.

19. An adenovirus vector comprising (a) an adenovirus gene essential for replication under transcriptional control of a uroplakin II transcriptional regulatory element (TRE) comprising a nucleotide sequence selected from the group consisting of nucleotides 2028 to 2239 of SEQ ID NO:1; nucleotides 1647 to 2239 of SEQ ID NO:1; nucleotides 1223 to 2239 of SEQ ID NO:1; nucleotides 1 to 2239 of SEQ ID NO:1; nucleotides 430 to 2239 of SEQ ID NO:1; nucleotides 2023–2239 of SEQ ID NO:1; nucleotides 3005 to 3592 of SEQ ID NO:2; and 2627 to 3592 of SEQ ID NO:2; and (b) an E3 region.

20. The adenovirus vector according to claim 19, wherein the uroplakin II TRE is obtained from a mouse uroplakin II gene.

21. The adenovirus vector according to claim 19, wherein the uroplakin II TRE is from a human uroplakin II gene.

22. An in vitro host cell comprising the adenoviral vector of claim 6.

23. An in vitro host cell comprising the adenoviral vector of claim 19.

24. The adenovirus vector of claim 6, further comprising a polynucleotide encoding adenoviral death protein (ADP).

25. The adenovirus vector of claim 19, further comprising a polynucleotide encoding adenoviral death protein (ADP).

26. The adenovirus vector of claim 6, further comprising a GM-CSF gene.

27. The adenovirus vector of claim 19, further comprising a GM-CSF gene.

* * * * *

SEQUENCE LISTING

<160> NUMBER OF SEQ ID NOS: 46

<210> SEQ ID NO 1
<211> LENGTH: 2240
<212> TYPE: DNA
<213> ORGANISM: Artificial Sequence
<220> FEATURE:
<223> OTHER INFORMATION: Human uroplakin II 5' flanking region

<400> SEQUENCE: 1

```
tcgataggta cccactatag ggcacgcgtg gtcgacggcc cgggctggtc tggcaacttc    60
aagtgtgggc ctttcagacc ggcatcatca gtgttacggg gaagtcacta ggaatgcaga   120
attgattgag cacggtggct cacacctgta atcccaacac tctgggaggc caaggcaggt   180
ggatcacttg tggtcaggag tttgagacca gcctggccaa catggtgaaa cctcatctct   240
actaaaaata caaaaattag ctgggaatgg tggcacatgc ctataatccc agttactcag   300
gaggctgagg caggagaatc atttgaacct gggaggcaga ggttgcagtg agccgagatc   360
acgccactgc actccagcct gggtgacaca gcgagactct gtctcaaaaa aaaaaaaatg   420
cagaatttca ggcttcaccc cagacccact gcatgactgc atgagaagct gcatcttaac   480
aagatccctg gtaattcata cgcatattaa atttggagat gcactggcgt aagaccctcc   540
tactctctgc ttaggcccat gagttcttcc tttactgtca ttctccactc accccaaact   600
ttgagcctac ccttcccacc ttggcggtaa ggacacaacc tccctcacat tcctaccagg   660
accctaagct tccctgggac tgaggaagat agaatagttc gtggagcaaa cagatataca   720
gcaacagtct ctgtacagct ctcaggcttc tggaagttct acagcctctc ccgacaaagt   780
attccacttt ccacaagtaa ctctatgtgt ctgagtctca gtttccactt ttctctctct   840
ctctctctct caactttctg agacagagtt tcacttagtc gcccaggctg gagtgcaggg   900
gcacaatctc ggctcactgc aacctccacc tcctgggttc aagtgtttct cctgtctcag   960
cctcccgagt agctgggatt acaggcacac caccgcgt tagttttttgt atttttggta  1020
gagatggtgt ttcgccatat tggccaggct gatctcgaac tcctgacctc aggtgatccg  1080
cccacctcgg cctcccaaag tgctgggatt acaggcatga gccaccacgc ccggctgatc  1140
tcttttctat tttaatagag atcaaactct ctgtgttgcc taggctggtc ttgaactcct  1200
ggcctcgagt gatcctccca ccttggcctc ccaaagtgtt gagattacag gcatgagcca  1260
ctgtgcctgg cctcagttct actacaaaag gaagccagta ccagctacca cccagggtgg  1320
ctgtagggct acaatggagc acacagaacc cctacccagg gcccggaaga agccccgact  1380
cctctcccct ccctctgccc agaactcctc cgcttctttc tgatgtagcc cagggccgga  1440
ggaggcagtc agggaagttc tgtctctttt tcatgttatc ttacgaggtc tcttttctcc  1500
attctcagtc caacaaatgg ttgctgccca aggctgactg tgcccacccc caaccctgc  1560
tggccagggt caatgtctgt ctctctggtc tctccagaag tcttccatgg ccaccttcgt  1620
ccccacccctc cagaggaatc tgaaaccgca tgtgctccct ggcccccaca gcccctgcct  1680
ctcccagagc agcagtacct aagcctcagt gcactccaag aattgaaacc ctcagtctgc  1740
tgcccctccc caccagaatg tttctctccc attcttaccc actcaaggcc ctttcagtag  1800
ccccttggag tattctcttc ctacatatca gggcaacttc caaactcatc acccttctga  1860
ggggtggggg aaagaccccc accacatcgg gggagcagtc ctccaaggac tggccagtct  1920
ccagatgccc gtgcacacag gaacactgcc ttatgcacgg gagtcccaga agaagggggtg  1980
```

-continued

```
atttctttcc ccaccttagt tacaccatca agacccagcc agggcatccc ccctcctggc      2040
ctgagggcca gctccccatc ctgaaaaacc tgtctgctct ccccacccct ttgaggctat      2100
agggcccaag gggcaggttg gactggattc ccctccagcc cctcccgccc ccaggacaaa      2160
atcagccacc ccaggggcag ggcctcactt gcctcaggaa ccccagcctg ccagcaccta      2220
ttccacctcc cagcccagca                                                  2240

<210> SEQ ID NO 2
<211> LENGTH: 3592
<212> TYPE: DNA
<213> ORGANISM: Artificial Sequence
<220> FEATURE:
<223> OTHER INFORMATION: Mouse uroplakin II 5' flanking region

<400> SEQUENCE: 2
ctcgaggatc tcggccctct ttctgcatcc ttgtcctaaa tcattttcat atcttgctag        60
acctcagttt gagagaaacg aaccttctca ttttcaagtt gaaaaaaaaa agaggttcaa       120
agtggctcac tcaaagttac aagccaacac tcaccactac gagtacaatg ccaccatta       180 gtgctggcat gccccaggag acaggcatgc atattattct agatgactgg gaggcagagg      240
ggtggcctag tgaggtcaga ctgtggacag atcaggcaga tgtgggttct gatcccaatt      300
cctcaggccg cagaactact gtggttcaag aagggacaa aaggactgca gtccggaaca      360
ggaggtccat ttgagagctg actgagcaga agaggaaagt gaagaacttc tggggcaaga      420
gcttacccta ctttacagct ttgttgtctt ctttactcca ggggcgtccc tggtactcag      480
taaatgtctg ttggcttgag gaacatatgt gtaaggagga aggagaggga acttgaggga      540
gttaagactc aagaatcaat caaggagagg acagcagaga agacagggtt tgggagagag      600
actccagaca ttggccctgg ttcccttctt ggccactgtg aaaccctcca gaggaactga      660
gtgctgtggc tttaaatgat ctcagcactg tcagtgaagc gctctgctca aagagttatc      720
ctcttgctcc tgtgccgggg cctccccctc ctctcagctc ccaaacccctt ctcagccact     780 gtgatggcat aattagatgc gagagctcag accgtcaggt ctgctccagg aaccacccat      840
tttccccaac cccagagaaa ggtcctagtg gaaaagtggg ggccactgaa gggctgatgg      900
ggttctgtcc tttcccccat gctgggtgga cttaaagtct gcgatgtgtg tagggggtag     960
aagacaacag aacctggggg ctccggctgg gagcaggagg aactctcacc agacgatctc     1020
caaatttact gtgcaatgga cgatcaggaa actggttcag atgtagcttc tgatacagtg     1080
ggtctgaggt aaaacccgaa acttaatttc tttcaaaaat ttaaagttgc atttattatt     1140
ttatatgtgt gcccatatgt gtgccacagt gtctatgtgg aggtcagagg gcaagttgtg     1200
ggcattggct ctctcctttc ataatgtggc ttctggggac caaaatgtca ggcatggtgg     1260
caagagcttt tacctgttga gccatctcat ggtttcgtaa aacttcctat gacgcttaca     1320
ggtaacgcag agacacagac tcacatttgg agttagcaga tgctgtattg gtgtaaacac     1380
tcatacacag acacacacac atactcatac acacacacac acacttatca catgcacaca     1440
catactcgta tacacacaga cacacacaca tgcactctca cattcacata ttcatacaca     1500
tccacacaca cactcatcca cacacacaga cacacatact catccacaca cacacacaca     1560
catactcata cacacacaca gacacacata ctcatacaca cacacagaca cacacatata     1620
atcatacata cacagacaca ctcatacatg tgcacacaca cactcatcca cacacacaca     1680
ctcatacaca cacacactca tacacacaca cactcataca cacacacacg aggttttct      1740
```

| | |
|---|---|
| caggctgcct ttgggtggag actggaactg atttctgttt ttcagctcct tggcttttg | 1800 |
| tcccttaga tgagatctcc tcctcactt acacacagaa agatcacaca cgagggagaa | 1860 |
| ctggcggtgc ggaagagggc tacacggtag ggtgtcaggg tcaggagatc ttcctggcaa | 1920 |
| gtctcaaacc tccacatagc acagtgttta cgtgaggatt taggaggaat caggaagagg | 1980 |
| attggtttac tgcagagcag accatatagg tccactccta agccccattt gaaattagaa | 2040 |
| gtgagacagt gtgggataaa aagagcagat ctctggtcac atttttaaag ggatatgagg | 2100 |
| gtcctgtgcc tttaagcctt cccatctccc tccaatcccc cctcaccttc cccaccctaa | 2160 |
| ccctccccag gtttctggag gagcagagtt gcgtcttctc cctgccctgc cgagctgctc | 2220 |
| actggctgct ctagaggctg tgctttgcgg tctccatgga aaccattagt tgctaagcaa | 2280 |
| ctggagcatc atctgtgctg agctcaggtc ctatcgagtt cacctagctg agacacccac | 2340 |
| gcccctgcag ccactttgca gtgacaagcc tgagtctcag gttctgcatc tataaaaacg | 2400 |
| agtagccttt caggagggca tgcagagccc cctggccagc gtctagagga gaggtgactg | 2460 |
| agtggggcca tgtcactcgt ccatggctgg agaacctcca tcagtctccc agttagcctg | 2520 |
| gggcaggaga gaaccagagg agctgtggct gctgattgga tgatttacgt acccaatctg | 2580 |
| ttgtcccagg catcgaaccc cagagcgacc tgcacacatg ccaccgctgc cccgccctcc | 2640 |
| acctcctctg ctcctggtta caggattgtt ttgtcttgaa gggttttgtt gttgctactt | 2700 |
| tttgctttgt ttttctttt ttaacataag gtttctctgt gtagccctag ctgtcctgga | 2760 |
| actcactctg tagaccaggc tggcctcaaa ctcagaaatc caccttcctc ccaagtgctg | 2820 |
| ggattaaagg cattcgcacc atcgcccagc ccccggtctt gtttcctaag gtttccctgc | 2880 |
| tttactcgct acccgttgca caaccgcttg ctgtccaagt ctgtttgtat ctactccacc | 2940 |
| gcccactagc cttgctggac tggacctacg tttacctgga agccttcact aacttccctt | 3000 |
| gtctccacct tctggagaaa tctgaaggct cacactgata ccctccgctt ctcccagagt | 3060 |
| cgcagtttct taggcctcag ttaaatacca gaattggatc tcaggctctg ctatccccac | 3120 |
| cctacctaac caaccccctc ctctcccatc cttactagcc aaagccctt caacccttgg | 3180 |
| ggcttttcct acacctacac accagggcaa ttttagaact catggctctc ctagaaaacg | 3240 |
| cctacctcct tggagactga ccctctacag tccaggaggc agacactcag acagaggaac | 3300 |
| tctgtccttc agtcgcggga gttccagaaa gagccatact cccctgcaga gctaactaag | 3360 |
| ctgccaggac ccagccagag catccccctt tagccgaggg ccagctcccc agaatgaaaa | 3420 |
| acctgtctgg ggcccctccc tgaggctaca gtcgccaagg ggcaagttgg actggattcc | 3480 |
| cagcagcccc tcccactccg agacaaaatc agctaccctg gggcaggcct cattggcccc | 3540 |
| aggaaacccc agcctgtcag cacctgttcc aggatccagt cccagcgcag ta | 3592 |

<210> SEQ ID NO 3
<211> LENGTH: 307
<212> TYPE: DNA
<213> ORGANISM: Artificial Sequence
<220> FEATURE:
<223> OTHER INFORMATION: Nucleotide sequence for ADP

<400> SEQUENCE: 3

| | |
|---|---|
| gatgaccggc tcaaccatcg cgcccacaac ggactatcgc aacaccactg ctaccggact | 60 |
| aacatctgcc ctaaatttac cccaagttca tgcctttgtc aatgactggg cgagcttgga | 120 |
| catgtggtgg ttttccatag cgcttatgtt tgtttgcctt attattatgt ggcttatttg | 180 |
| ttgcctaaag cgcagacgcg ccagacccc catctatagg cctatcattg tgctcaaccc | 240 |

```
acacaatgaa aaaattcata gattggacgg tctgaaacca tgttctcttc ttttacagta    300
tgattaa                                                              307
```

<210> SEQ ID NO 4
<211> LENGTH: 101
<212> TYPE: PRT
<213> ORGANISM: Artificial Sequence
<220> FEATURE:
<223> OTHER INFORMATION: Amino acid sequence for ADP

<400> SEQUENCE: 4

```
Met Thr Gly Ser Thr Ile Ala Pro Thr Thr Asp Tyr Arg Asn Thr Thr
 1               5                  10                  15

Ala Thr Gly Leu Thr Ser Ala Leu Asn Leu Pro Gln Val His Ala Phe
            20                  25                  30

Val Asn Asp Trp Ala Ser Leu Asp Met Trp Trp Phe Ser Ile Ala Leu
        35                  40                  45

Met Phe Val Cys Leu Ile Ile Met Trp Leu Ile Cys Cys Leu Lys Arg
    50                  55                  60

Arg Arg Ala Arg Pro Pro Ile Tyr Arg Pro Ile Val Leu Asn Pro
65                  70                  75                  80

His Asn Glu Lys Ile His Arg Leu Asp Gly Leu Lys Pro Cys Ser Leu
                85                  90                  95

Leu Leu Gln Tyr Asp
            100
```

<210> SEQ ID NO 5
<211> LENGTH: 29
<212> TYPE: DNA
<213> ORGANISM: Artificial Sequence
<220> FEATURE:
<223> OTHER INFORMATION: PCR Primer 66.119.1

<400> SEQUENCE: 5

```
accggtctcg aggatctcgg ccctctttc                                       29
```

<210> SEQ ID NO 6
<211> LENGTH: 26
<212> TYPE: DNA
<213> ORGANISM: Artificial Sequence
<220> FEATURE:
<223> OTHER INFORMATION: PCR Primer 66.119.2

<400> SEQUENCE: 6

```
accggtactg cgctgggact ggatcc                                          26
```

<210> SEQ ID NO 7
<211> LENGTH: 34
<212> TYPE: DNA
<213> ORGANISM: Artificial Sequence
<220> FEATURE:
<223> OTHER INFORMATION: PCR Primer 100.24.1

<400> SEQUENCE: 7

```
aagcttaccg gtactgcgct gggactggat cctg                                 34
```

<210> SEQ ID NO 8
<211> LENGTH: 36
<212> TYPE: DNA
<213> ORGANISM: Artificial Sequence
<220> FEATURE:
<223> OTHER INFORMATION: PCR Primer 100.27.1

```
<400> SEQUENCE: 8
accatggacc ggtctcgagg atctcggccc tctttc                                36

<210> SEQ ID NO 9
<211> LENGTH: 36
<212> TYPE: DNA
<213> ORGANISM: Artificial Sequence
<220> FEATURE:
<223> OTHER INFORMATION: PCR Primer 100.24.3

<400> SEQUENCE: 9
accatggacc ggtacgtacc caatctgttg tcccag                                36

<210> SEQ ID NO 10
<211> LENGTH: 35
<212> TYPE: DNA
<213> ORGANISM: Artificial Sequence
<220> FEATURE:
<223> OTHER INFORMATION: PCR Primer 100.24.2

<400> SEQUENCE: 10
accatggacc ggtcactagc cttgctggac tggac                                 35

<210> SEQ ID NO 11
<211> LENGTH: 24
<212> TYPE: DNA
<213> ORGANISM: Artificial Sequence
<220> FEATURE:
<223> OTHER INFORMATION: PCR Primer 100.84.1

<400> SEQUENCE: 11
aagaatcagg atcaagggca agtc                                             24

<210> SEQ ID NO 12
<211> LENGTH: 25
<212> TYPE: DNA
<213> ORGANISM: Artificial Sequence
<220> FEATURE:
<223> OTHER INFORMATION: PCR Primer 100.84.2

<400> SEQUENCE: 12
aatgctgggc tgggaggtgg aatag                                            25

<210> SEQ ID NO 13
<211> LENGTH: 29
<212> TYPE: DNA
<213> ORGANISM: Artificial Sequence
<220> FEATURE:
<223> OTHER INFORMATION: PCR Primer 100.113.1

<400> SEQUENCE: 13
aggggtaccc actatagggc acgcgtggt                                        29

<210> SEQ ID NO 14
<211> LENGTH: 32
<212> TYPE: DNA
<213> ORGANISM: Artificial Sequence
<220> FEATURE:
<223> OTHER INFORMATION: PCR Primer 100.113.2

<400> SEQUENCE: 14
acccaagctt gggatgctgg gctgggaggt gg                                    32

<210> SEQ ID NO 15
```

```
<211> LENGTH: 39
<212> TYPE: DNA
<213> ORGANISM: Artificial Sequence
<220> FEATURE:
<223> OTHER INFORMATION: PCR Primer 100.126.3

<400> SEQUENCE: 15
acgaggggta cccaccggta ccgcatgtgc tccctggcc                            39

<210> SEQ ID NO 16
<211> LENGTH: 40
<212> TYPE: DNA
<213> ORGANISM: Artificial Sequence
<220> FEATURE:
<223> OTHER INFORMATION: PCR Primer 100.126.1

<400> SEQUENCE: 16
agacccaagc ttgggaccgg tatgctgggc tgggaggtgg                           40

<210> SEQ ID NO 17
<211> LENGTH: 38
<212> TYPE: DNA
<213> ORGANISM: Artificial Sequence
<220> FEATURE:
<223> OTHER INFORMATION: PCR Primer 100.126.2

<400> SEQUENCE: 17
acgaggggta cccaccggtc cccctcctg gcctgagg                              38

<210> SEQ ID NO 18
<211> LENGTH: 37
<212> TYPE: DNA
<213> ORGANISM: Artificial Sequence
<220> FEATURE:
<223> OTHER INFORMATION: PCR Primer 100.82.1

<400> SEQUENCE: 18
aggggtaccc cggccggtca cacagcagga gagacac                              37

<210> SEQ ID NO 19
<211> LENGTH: 41
<212> TYPE: DNA
<213> ORGANISM: Artificial Sequence
<220> FEATURE:
<223> OTHER INFORMATION: PCR Primer 100.82.2

<400> SEQUENCE: 19
acccaagctt gggcggccgc atcctgggac acatgagcag g                         41

<210> SEQ ID NO 20
<211> LENGTH: 36
<212> TYPE: DNA
<213> ORGANISM: Artificial Sequence
<220> FEATURE:
<223> OTHER INFORMATION: PCR Primer 100.83.1

<400> SEQUENCE: 20
aggggtaccc cggccgcaac cctgccttcg aggttc                               36

<210> SEQ ID NO 21
<211> LENGTH: 28
<212> TYPE: DNA
<213> ORGANISM: Artificial Sequence
<220> FEATURE:
<223> OTHER INFORMATION: PCR Primer 96.74.2

<400> SEQUENCE: 21
```

```
gacgtcgact aattccggtt attttcca                                28

<210> SEQ ID NO 22
<211> LENGTH: 28
<212> TYPE: DNA
<213> ORGANISM: Artificial Sequence
<220> FEATURE:
<223> OTHER INFORMATION: PCR Primer 96.74.1

<400> SEQUENCE: 22
gacgtcgaca tcgtgttttt caaaggaa                                28

<210> SEQ ID NO 23
<211> LENGTH: 29
<212> TYPE: DNA
<213> ORGANISM: Artificial Sequence
<220> FEATURE:
<223> OTHER INFORMATION: PCR Primer 127.2.1

<400> SEQUENCE: 23
aggaccggtc actatagggc acgcgtggt                               29

<210> SEQ ID NO 24
<211> LENGTH: 31
<212> TYPE: DNA
<213> ORGANISM: Artificial Sequence
<220> FEATURE:
<223> OTHER INFORMATION: PCR Primer 127.2.2

<400> SEQUENCE: 24
aggaccggtg ggatgctggg ctgggaggtg g                            31

<210> SEQ ID NO 25
<211> LENGTH: 25
<212> TYPE: DNA
<213> ORGANISM: Artificial Sequence
<220> FEATURE:
<223> OTHER INFORMATION: PCR Primer 96.74.3

<400> SEQUENCE: 25
cctgagacgc ccgacatcac ctgtg                                   25

<210> SEQ ID NO 26
<211> LENGTH: 30
<212> TYPE: DNA
<213> ORGANISM: Artificial Sequence
<220> FEATURE:
<223> OTHER INFORMATION: PCR Primer 96.74.4

<400> SEQUENCE: 26
tgctgaatgg tcgacatgga ggcttgggag                              30

<210> SEQ ID NO 27
<211> LENGTH: 25
<212> TYPE: DNA
<213> ORGANISM: Artificial Sequence
<220> FEATURE:
<223> OTHER INFORMATION: PCR Primer 96.74.5

<400> SEQUENCE: 27
cacaaccgct ctccacagat gcatg                                   25

<210> SEQ ID NO 28
<211> LENGTH: 30
<212> TYPE: DNA
```

-continued

<213> ORGANISM: Artificial Sequence
<220> FEATURE:
<223> OTHER INFORMATION: PCR Primer 96.74.6

<400> SEQUENCE: 28
gtcgaccatt cagcaaacaa aggcgttaac                              30

<210> SEQ ID NO 29
<211> LENGTH: 30
<212> TYPE: DNA
<213> ORGANISM: Artificial Sequence
<220> FEATURE:
<223> OTHER INFORMATION: PCR Primer 127.50.1

<400> SEQUENCE: 29
aggaccggtc aggcttcacc ccagacccac                              30

<210> SEQ ID NO 30
<211> LENGTH: 24
<212> TYPE: DNA
<213> ORGANISM: Artificial Sequence
<220> FEATURE:
<223> OTHER INFORMATION: PCR Primer 31.166.1

<400> SEQUENCE: 30
tgcgccggtg tacacaggaa gtga                                    24

<210> SEQ ID NO 31
<211> LENGTH: 21
<212> TYPE: DNA
<213> ORGANISM: Artificial Sequence
<220> FEATURE:
<223> OTHER INFORMATION: PCR Primer 32.32.1

<400> SEQUENCE: 31
gagtttgtgc catcggtcta c                                       21

<210> SEQ ID NO 32
<211> LENGTH: 21
<212> TYPE: DNA
<213> ORGANISM: Artificial Sequence
<220> FEATURE:
<223> OTHER INFORMATION: PCR Primer 32.32.2

<400> SEQUENCE: 32
aatcaatcct tagtcctcct g                                       21

<210> SEQ ID NO 33
<211> LENGTH: 25
<212> TYPE: DNA
<213> ORGANISM: Artificial Sequence
<220> FEATURE:
<223> OTHER INFORMATION: PCR Primer 51.176

<400> SEQUENCE: 33
gcagaaaaat cttccaaaca ctccc                                   25

<210> SEQ ID NO 34
<211> LENGTH: 27
<212> TYPE: DNA
<213> ORGANISM: Artificial Sequence
<220> FEATURE:
<223> OTHER INFORMATION: PCR Primer 99.120.1

<400> SEQUENCE: 34
acgtacaccg gtcgttacat aacttac                                 27

```
<210> SEQ ID NO 35
<211> LENGTH: 26
<212> TYPE: DNA
<213> ORGANISM: Artificial Sequence
<220> FEATURE:
<223> OTHER INFORMATION: PCR Primer 99.120.2

<400> SEQUENCE: 35
ctagcaaccg gtcggttcac taaacg                                    26

<210> SEQ ID NO 36
<211> LENGTH: 29
<212> TYPE: DNA
<213> ORGANISM: Artificial Sequence
<220> FEATURE:
<223> OTHER INFORMATION: PCR Primer 37.124.1

<400> SEQUENCE: 36
gccttaatta aaagcaaacc tcacctccg                                 29

<210> SEQ ID NO 37
<211> LENGTH: 30
<212> TYPE: DNA
<213> ORGANISM: Artificial Sequence
<220> FEATURE:
<223> OTHER INFORMATION: PCR Primer 37.146.1

<400> SEQUENCE: 37
gtggaacaaa aggtgattaa aaaatcccag                                30

<210> SEQ ID NO 38
<211> LENGTH: 30
<212> TYPE: DNA
<213> ORGANISM: Artificial Sequence
<220> FEATURE:
<223> OTHER INFORMATION: PCR Primer 37.124.3

<400> SEQUENCE: 38 cacctttgt tccaccgctc tgcttattac                                 30

<210> SEQ ID NO 39
<211> LENGTH: 28
<212> TYPE: DNA
<213> ORGANISM: Artificial Sequence
<220> FEATURE:
<223> OTHER INFORMATION: PCR Primer 37.124.4

<400> SEQUENCE: 39
ggcttaatta actgtgaaag gtgggagc                                  28

<210> SEQ ID NO 40
<211> LENGTH: 23
<212> TYPE: DNA
<213> ORGANISM: Artificial Sequence
<220> FEATURE:
<223> OTHER INFORMATION: PCR Primer 33.81.1

<400> SEQUENCE: 40
gcagctcact taagttcatg tcg                                       23

<210> SEQ ID NO 41
<211> LENGTH: 27
<212> TYPE: DNA
<213> ORGANISM: Artificial Sequence
<220> FEATURE:
```

-continued

<223> OTHER INFORMATION: PCR Primer 33.81.2

<400> SEQUENCE: 41
tcagcctagg aaatatgact acgtccg                                              27

<210> SEQ ID NO 42
<211> LENGTH: 519
<212> TYPE: DNA
<213> ORGANISM: Artificial Sequence
<220> FEATURE:
<223> OTHER INFORMATION: IRES from EMCV

<400> SEQUENCE: 42
gacgtcgact aattccggtt attttccacc atattgccgt cttttggcaa tgtgagggcc          60
cggaaacctg gccctgtctt cttgacgagc attcctaggg gtctttcccc tctcgccaaa        120
ggaatgcaag gtctgttgaa tgtcgtgaag gaagcagttc ctctggaagc ttcttgaaga        180
caaacaacgt ctgtagcgac cctttgcagg cagcggaacc ccccacctgg cgacaggtgc        240
ctctgcggcc aaaagccacg tgtataagat acacctgcaa aggcggcaca accccagtgc        300
cacgttgtga gttggatagt tgtggaaaga gtcaaatggc tctcctcaag cgtattcaac        360
aaggggctga aggatgccca aaggtaccc cattgtatgg gatctgatct ggggcctcgg        420
tgcacatgct ttacatgtgt ttagtcgagg ttaaaaaacg tctaggcccc ccgaaccacg        480
gggacgtggt tttcctttga aaaacacgat gtcgacgtc                              519

<210> SEQ ID NO 43
<211> LENGTH: 188
<212> TYPE: DNA
<213> ORGANISM: Artificial Sequence
<220> FEATURE:
<223> OTHER INFORMATION: IRES from VEGF

<400> SEQUENCE: 43
acgtagtcga cagcgcagag gcttggggca gccgagcggc agccaggccc cggcccgggc          60
ctcggttcca gaagggagag gagcccgcca aggcgcgcaa gagagcgggc tgcctcgcag        120
tccgagccgg agagggagcg cgagccgcgc cggccccgga cggcctccga aaccatggtc        180
gacacgta                                                                188

<210> SEQ ID NO 44
<211> LENGTH: 341
<212> TYPE: DNA
<213> ORGANISM: Artificial Sequence
<220> FEATURE:
<223> OTHER INFORMATION: 5' UTR region of HCV

<400> SEQUENCE: 44 gccagcccc tgatgggggc gacactccgc catgaatcac tcccctgtga ggaactactg           60
tcttcacgca gaaagcgtct agccatggcg ttagtatgag tgtcgtgcag cctccaggac        120
cccccctccc gggagagcca tagtggtctg cggaaccggt gagtacaccg gaattgccag        180
gacgaccggg tcctttcttg gattaaaccg ctcaatgcct ggagatttgg gcgtgccccc        240
gcaagactgc tagccgagta gtgttgggtc gcgaaaggcc ttgtggtact gcctgatagg        300
gtgcttgcga gtgccccggg aggtctcgta gaccgtgcac c                            341

<210> SEQ ID NO 45
<211> LENGTH: 595
<212> TYPE: DNA
<213> ORGANISM: Artificial Sequence -continued

```
<220> FEATURE:
<223> OTHER INFORMATION: 5' UTR region of BiP

<400> SEQUENCE: 45 cccgggtca ctcctgctgg acctactccg accccctagg ccgggagtga aggcgggact      60
tgtgcggtta ccagcggaaa tgcctcgggg tcagaagtcg caggagagat agacagctgc    120
tgaaccaatg ggaccagcgg atggggcgga tgttatctac cattggtgaa cgttagaaac    180
gaatagcagc caatgaatca gctgggggg cggagcagtg acgtttattg cggaggggc     240 cgcttcgaat cggcggcggc cagcttggtg gcctgggcca atgaacggcc tccaacgagc    300
agggccttca ccaatcggcg gcctccacga cggggctggg ggagggtata taagccgagt    360
aggcgacggt gaggtcgacg ccggccaaga cagcacagac agattgacct attggggtgt    420
ttcgcgagtg tgagagggaa gcgccgcggc ctgtatttct agacctgccc ttcgcctggt    480
tcgtggcgcc ttgtgacccc gggcccctgc cgcctgcaag tcgaaattgc gctgtgctcc    540
tgtgctacgg cctgtggctg gactgcctgc tgctgcccaa ctggctggca agatg         595

<210> SEQ ID NO 46
<211> LENGTH: 575
<212> TYPE: DNA
<213> ORGANISM: Artificial Sequence
<220> FEATURE:
<223> OTHER INFORMATION: 5' UTR region of PDGF

<400> SEQUENCE: 46
gtttgcacct ctccctgccc gggtgctcga gctgccgttg caaagccaac tttggaaaaa     60
gttttttggg ggagacttgg gccttgaggt gcccagctcc gcgctttccg attttggggg   120
ctttccagaa aatgttgcaa aaaagctaag ccggcgggca gaggaaaacg cctgtagccg    180
gcgagtgaag acgaaccatc gactgccgtg ttccttttcc tcttggaggt tggagtcccc    240
tgggcgcccc cacaccccta gacgcctcgg ctggttcgcg acgcagcccc ccggccgtgg    300
atgctgcact cgggctcggg atccgcccag gtagccggcc tcggacccag gtcctgcgcc    360
caggtcctcc cctgccccc agcgacggag ccggggccgg gggcggcggc gccggggca     420 tgcgggtgag ccgcggctgc agaggcctga gcgcctgatc gccgcggacc tgagccgagc    480
ccacccccct ccccagcccc ccaccctggc cgcgggggcg gcgcgctcga tctacgcgtc    540
cggggccccg cggggccggg cccggagtcg gcatg                               575
```